(12) United States Patent
Popitz et al.

(10) Patent No.: US 10,898,015 B2
(45) Date of Patent: Jan. 26, 2021

(54) METHOD, SYSTEM, AND APPARATUS FOR FACILITATING POSITIONING A PERSON IN LATERAL SNIFF POSITION

(71) Applicant: Popitz, LLC, Wellesley, MA (US)

(72) Inventors: Michael D. Popitz, Marion, MA (US); Andrew T. Fligor, Weston, MA (US); Jesse S. Drake, Westborough, MA (US); Howard P. Miller, Concord, MA (US); Justin McCarthy, Boxborough, MA (US); Jonathan G. Sloane, Dover, MA (US)

(73) Assignee: Popitz, LLC, Wellesley, MA (US)

( * ) Notice: Subject to any disclaimer, the term of this patent is extended or adjusted under 35 U.S.C. 154(b) by 0 days.

(21) Appl. No.: 16/689,083

(22) Filed: Nov. 20, 2019

(65) Prior Publication Data

US 2020/0155395 A1    May 21, 2020

Related U.S. Application Data

(60) Provisional application No. 62/861,859, filed on Jun. 14, 2019, provisional application No. 62/836,558, (Continued)

(51) Int. Cl.
*A47G 9/10* (2006.01)
*A61G 7/07* (2006.01)

(52) U.S. Cl.
CPC .......... *A47G 9/1081* (2013.01); *A47G 9/109* (2013.01); *A61G 7/07* (2013.01); *A61G 7/072* (2013.01);
(Continued)

(58) Field of Classification Search
CPC .. A47G 9/109; A47G 2009/1018; A61G 7/07; A61G 7/072; A61G 2000/322
(Continued)

(56) References Cited

U.S. PATENT DOCUMENTS 2,700,779 A * 2/1955 Tolkowsky .............. A47G 9/10
                                                              5/632
4,118,813 A * 10/1978 Armstrong .............. A47G 9/10
                                                              5/636
(Continued)

FOREIGN PATENT DOCUMENTS

EP      1488766 A1    12/2004
EP      2201921 A2     6/2010
(Continued)

OTHER PUBLICATIONS

U.S. Appl. No. 16/689,081, filed Nov. 20, 2019, Michael D. Popitz, et al.

(Continued)

*Primary Examiner* — Peter M. Cuomo
*Assistant Examiner* — Myles A Throop
(74) *Attorney, Agent, or Firm* — Nelson Mullins Riley & Scarborough LLP; Thomas J. Engellenner; Reza Mollaaghababa

(57) ABSTRACT

In one aspect, an apparatus for supporting the head and neck of a user for airway management is disclosed, which comprises a top surface including at least one head-receiving portion configured and dimensioned for receiving and supporting a user's head, and at least one recess neck opening for supporting a user's neck when the user's head is received in the head-receiving portion. The apparatus further includes at least one chin support protruding above the top surface and configured for facilitating placing the user in a sniff position when the user's head is received in the head-receiving portion. The chin support can include a top surface segment and a lateral surface segment, where at least a portion of the lateral surface segment of the chin support extends from the top surface segment thereof to the at least one recess neck opening.

20 Claims, 38 Drawing Sheets

Related U.S. Application Data filed on Apr. 19, 2019, provisional application No. 62/824,203, filed on Mar. 26, 2019, provisional application No. 62/772,492, filed on Nov. 28, 2018, provisional application No. 62/769,869, filed on Nov. 20, 2018.

(52) U.S. Cl.
CPC ............... *A47G 2009/1018* (2013.01); *A61G 2200/322* (2013.01); *A61G 2200/327* (2013.01)

(58) Field of Classification Search
USPC ...................................................... 5/636–637
See application file for complete search history.

(56) References Cited

U.S. PATENT DOCUMENTS

| | | | |
|---|---|---|---|
| 4,424,599 A * | 1/1984 | Hannouche | A47G 9/1081 5/632 |
| 4,494,261 A * | 1/1985 | Morrow | A47G 9/109 5/636 |
| 4,550,458 A * | 11/1985 | Fiore | A47C 7/383 297/393 |
| 4,850,067 A | 7/1989 | Latorre | |
| 4,918,774 A | 4/1990 | Popitz | |
| 5,018,231 A * | 5/1991 | Wang | A47G 9/10 5/636 |
| 5,048,136 A * | 9/1991 | Popitz | A47C 21/046 128/870 |
| 5,457,832 A * | 10/1995 | Tatum | A61F 5/01 5/636 |
| 5,848,448 A * | 12/1998 | Boyd | A47G 9/10 5/636 |
| 6,003,177 A | 12/1999 | Ferris | |
| 6,006,380 A | 12/1999 | Sramek | |
| 6,401,279 B1 | 6/2002 | Vaughn | |
| 6,408,468 B1 * | 6/2002 | Comfort | A47G 9/10 5/498 |
| 6,446,288 B1 * | 9/2002 | Pi | A47G 9/10 5/636 |
| 6,671,907 B1 | 1/2004 | Zuberi | |
| 6,751,818 B2 * | 6/2004 | Troop | A61G 7/072 5/630 |
| 6,935,340 B2 | 8/2005 | Saied | |
| 7,020,919 B2 | 4/2006 | Inaba | |
| 7,077,141 B2 | 7/2006 | Troop | |
| 7,089,615 B1 | 8/2006 | Parimuha | |
| 7,100,227 B2 | 9/2006 | Frisbee | |
| 7,127,758 B2 | 10/2006 | Gabbay | |
| 7,127,759 B2 | 10/2006 | Koops | |
| 7,213,280 B2 | 5/2007 | Lavin et al. | |
| 7,350,250 B2 | 4/2008 | Froelich | |
| 7,383,599 B2 | 6/2008 | Gabbay | |
| 7,406,732 B2 | 8/2008 | Ramaiah | |
| 7,467,431 B2 | 12/2008 | Weedling et al. | |
| 7,546,651 B2 | 6/2009 | Groteke et al. | |
| 7,594,288 B1 | 9/2009 | Holliday et al. | |
| 7,676,870 B2 | 3/2010 | Chen | |
| 7,681,262 B2 | 3/2010 | Weedling et al. | |
| 7,716,763 B2 | 5/2010 | Nissen et al. | |
| 7,908,591 B1 | 3/2011 | Nell et al. | |
| 7,908,691 B2 * | 3/2011 | Small | A47C 20/027 5/630 |
| 7,926,134 B2 | 4/2011 | Carlos | |
| 8,001,636 B2 | 8/2011 | Nissen et al. | |
| 8,065,766 B1 | 11/2011 | Fierro | |
| 8,069,515 B1 * | 12/2011 | Tingey | A47G 9/10 5/632 |
| 8,118,030 B1 | 2/2012 | Bugeja | |
| 8,161,588 B1 * | 4/2012 | Anson | A47G 9/109 5/630 |
| 8,176,586 B2 | 5/2012 | Berke et al. | |
| 8,176,921 B2 | 5/2012 | Bazargani | |
| 8,234,732 B2 | 8/2012 | Bacon | |
| 8,291,534 B2 | 10/2012 | Karlson | |
| 8,316,489 B1 | 11/2012 | Leal | |
| 8,429,775 B2 | 4/2013 | North | |
| 8,459,264 B2 | 6/2013 | Tweardy | |
| 8,512,370 B2 | 8/2013 | Sorensen | |
| 8,566,985 B2 | 10/2013 | Kim | |
| 8,650,684 B1 | 2/2014 | Mackinnon | |
| 8,671,481 B2 | 3/2014 | Franklin | |
| 8,677,531 B2 | 3/2014 | Popitz | |
| 8,769,744 B1 | 7/2014 | Brown | |
| 8,806,685 B2 | 8/2014 | Karlson | |
| 8,813,282 B2 | 8/2014 | Roban | |
| 8,973,190 B2 | 3/2015 | Oh et al. | |
| 8,997,285 B2 | 4/2015 | Moore | |
| 9,220,345 B2 * | 12/2015 | Davis | A47C 7/62 |
| 9,241,586 B1 | 1/2016 | Brown | |
| 9,265,681 B1 | 2/2016 | Bell | |
| 9,289,082 B1 * | 3/2016 | White | A47G 9/10 |
| 9,357,864 B2 | 6/2016 | Campagna | |
| 9,510,986 B2 | 12/2016 | Nesley | |
| 9,572,739 B1 | 2/2017 | Bell | |
| 9,707,152 B2 | 7/2017 | Lurie et al. | |
| 9,750,661 B2 | 9/2017 | Lurie et al. | |
| 9,801,782 B2 | 10/2017 | Lurie et al. | |
| 9,808,370 B1 | 11/2017 | Reser et al. | |
| 2002/0059680 A1 | 5/2002 | Mahoney et al. | |
| 2004/0010288 A1 | 1/2004 | Ghaly | |
| 2004/0139549 A1 | 7/2004 | Mohrekesh et al. | |
| 2005/0081866 A1 | 4/2005 | Saied | |
| 2006/0260055 A1 | 11/2006 | Frisbee | |
| 2007/0006382 A1 * | 1/2007 | Guez | A47G 9/10 5/638 |
| 2007/0011812 A1 * | 1/2007 | Drucker | A61F 5/56 5/636 |
| 2007/0144538 A1 | 6/2007 | Tweardy | |
| 2007/0181122 A1 | 8/2007 | Mulier | |
| 2007/0294829 A1 | 12/2007 | Callahan et al. | |
| 2008/0086818 A1 | 4/2008 | Sramek et al. | |
| 2008/0092908 A1 | 4/2008 | Costa | |
| 2008/0134437 A1 * | 6/2008 | Small | A47C 20/027 5/632 |
| 2008/0222813 A1 | 9/2008 | Aikman | |
| 2008/0282473 A1 | 11/2008 | Ramaiah | |
| 2009/0038077 A1 | 2/2009 | Han et al. | |
| 2009/0241967 A1 | 10/2009 | Orencel | |
| 2010/0229875 A1 | 9/2010 | Davis | |
| 2011/0056502 A1 | 3/2011 | Davis et al. | |
| 2011/0094033 A1 | 4/2011 | Lee | |
| 2011/0271964 A1 * | 11/2011 | Zhang | A47G 9/10 128/845 |
| 2012/0060846 A1 | 3/2012 | Leoniak et al. | |
| 2012/0073057 A1 | 3/2012 | Sramek | |
| 2012/0079660 A1 | 4/2012 | Chen | |
| 2013/0091632 A1 | 4/2013 | Roban | |
| 2013/0245395 A1 | 9/2013 | Bidarian Moniri | |
| 2014/0096777 A1 | 4/2014 | Derner | |
| 2014/0208515 A1 * | 7/2014 | Sramek | A47G 9/109 5/640 |
| 2014/0296747 A1 | 10/2014 | Herrnsdorf | |
| 2015/0128348 A1 | 5/2015 | Gottlieb | |
| 2015/0208812 A1 | 7/2015 | Fenton | |
| 2015/0265075 A1 * | 9/2015 | Liu | A61F 5/56 5/640 |
| 2016/0106238 A1 | 4/2016 | Vargas | |
| 2016/0151222 A1 * | 6/2016 | Pedro | A61G 13/121 128/845 |
| 2016/0354265 A1 | 12/2016 | Usoltseff | |
| 2017/0027344 A1 | 2/2017 | Herrnsdorf et al. | |
| 2017/0239076 A1 | 8/2017 | Stanton | |
| 2017/0245656 A1 | 8/2017 | Ribble et al. | |
| 2017/0246066 A1 | 8/2017 | Reilly et al. | |
| 2017/0258627 A1 | 9/2017 | Cuzzetto | |
| 2017/0326017 A1 | 11/2017 | Marinkovic | |
| 2018/0064573 A1 | 3/2018 | Mello et al. | |
| 2018/0078061 A1 | 3/2018 | Randall | |
| 2018/0220818 A1 | 8/2018 | Doughty | |

(56) References Cited

U.S. PATENT DOCUMENTS

2018/0256387 A1   9/2018   Anderson
2019/0069698 A1*  3/2019   Lin .................... A47G 9/1081

FOREIGN PATENT DOCUMENTS

| WO | 2001032112 A1 | 5/2001 | |
|---|---|---|---|
| WO | 2005018512 A1 | 3/2005 | |
| WO | 2008146429 A1 | 12/2008 | |
| WO | 2009063299 A2 | 5/2009 | |
| WO | 2010019237 A2 | 2/2010 | |
| WO | 2010052532 A1 | 5/2010 | |
| WO | 2010071899 A1 | 6/2010 | |
| WO | 2010082758 A2 | 7/2010 | |
| WO | 2014011123 A1 | 1/2014 | |
| WO | 2014021518 A1 | 2/2014 | |
| WO | 2014181020 A1 | 11/2014 | |
| WO | WO-2015119403 A1 * | 8/2015 | ............. A47G 9/109 |
| WO | 2015161146 A1 | 10/2015 | |
| WO | 2016034923 A1 | 3/2016 | |
| WO | 2016075464 A1 | 5/2016 | |
| WO | 2017166826 A1 | 10/2017 | |
| WO | 2018232549 A1 | 12/2018 | |

OTHER PUBLICATIONS

U.S. Appl. No. 16/689,088, filed Nov. 20, 2019, Michael D. Popitz, et al.
U.S. Appl. No. 29/713,974, filed Nov. 20, 2019, Michael D. Popitz, et al.
U.S. Appl. No. 29/713,975, filed Nov. 20, 2019, Michael D. Popitz, et al.
International Invitation to Pay Additional fees, PCT/US2019/062307, dated Jan. 17, 2020, 12 pages.
International Invitation to Pay Additional fees, PCT/US2019/062309, dated Jan. 17, 2020, 12 pages.
International Invitation to Pay Additional fees, PCT/US2019/062310, dated Jan. 21, 2020, 12 pages.
International Search Report and Written Opinion, PCT/US2019/062309, dated Mar. 11, 2020, 18 pages.

* cited by examiner

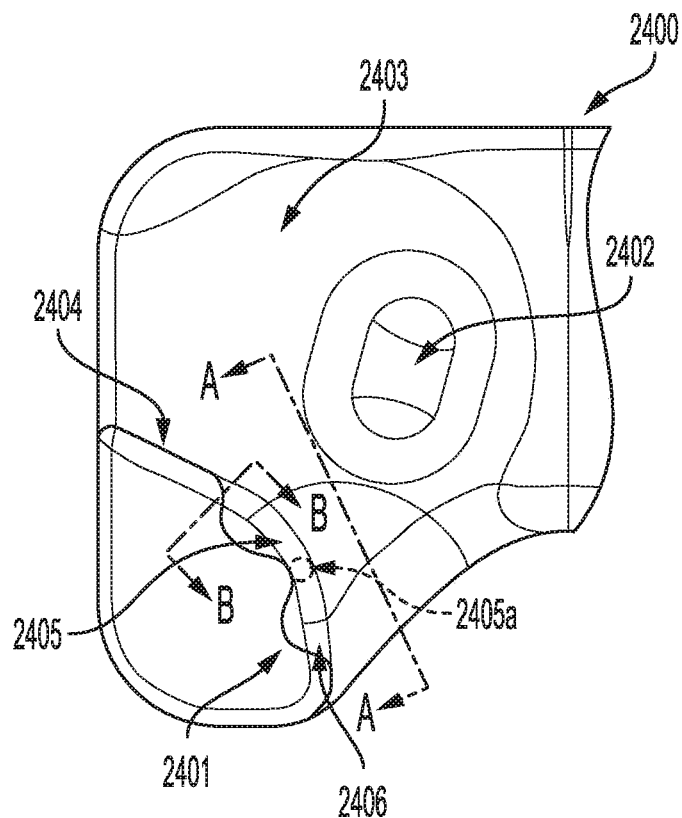
FIG. 10A
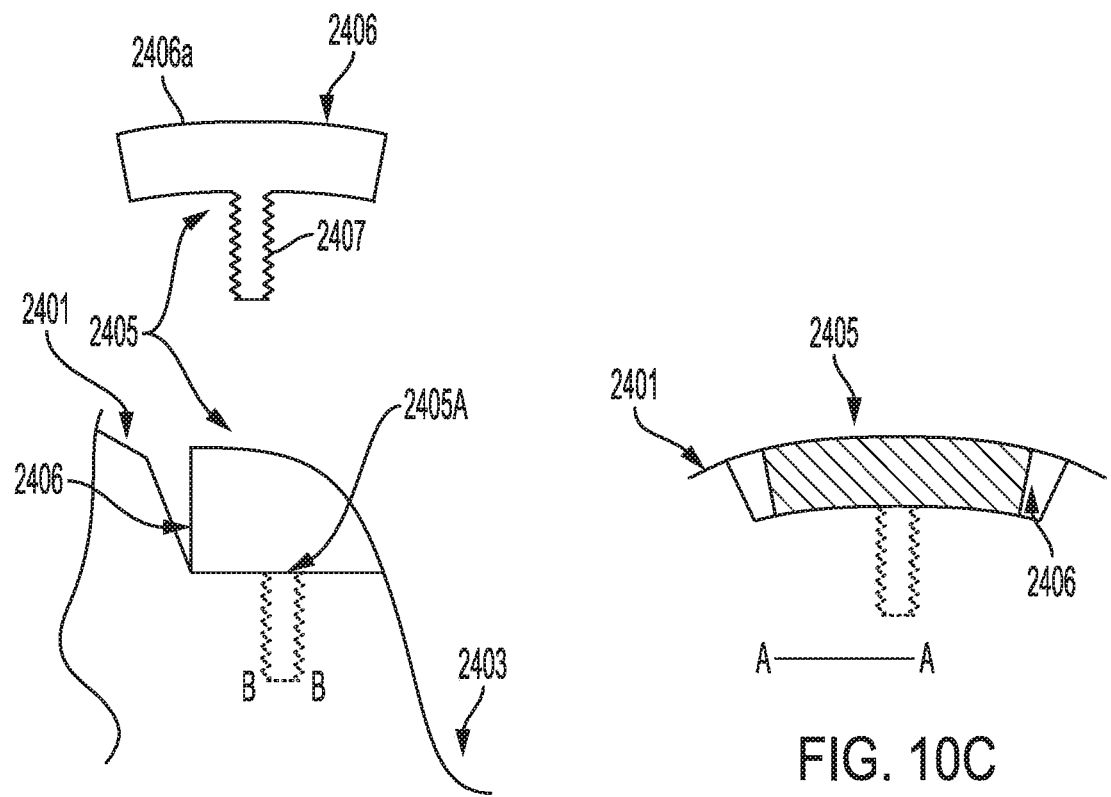
FIG. 10B
FIG. 10C

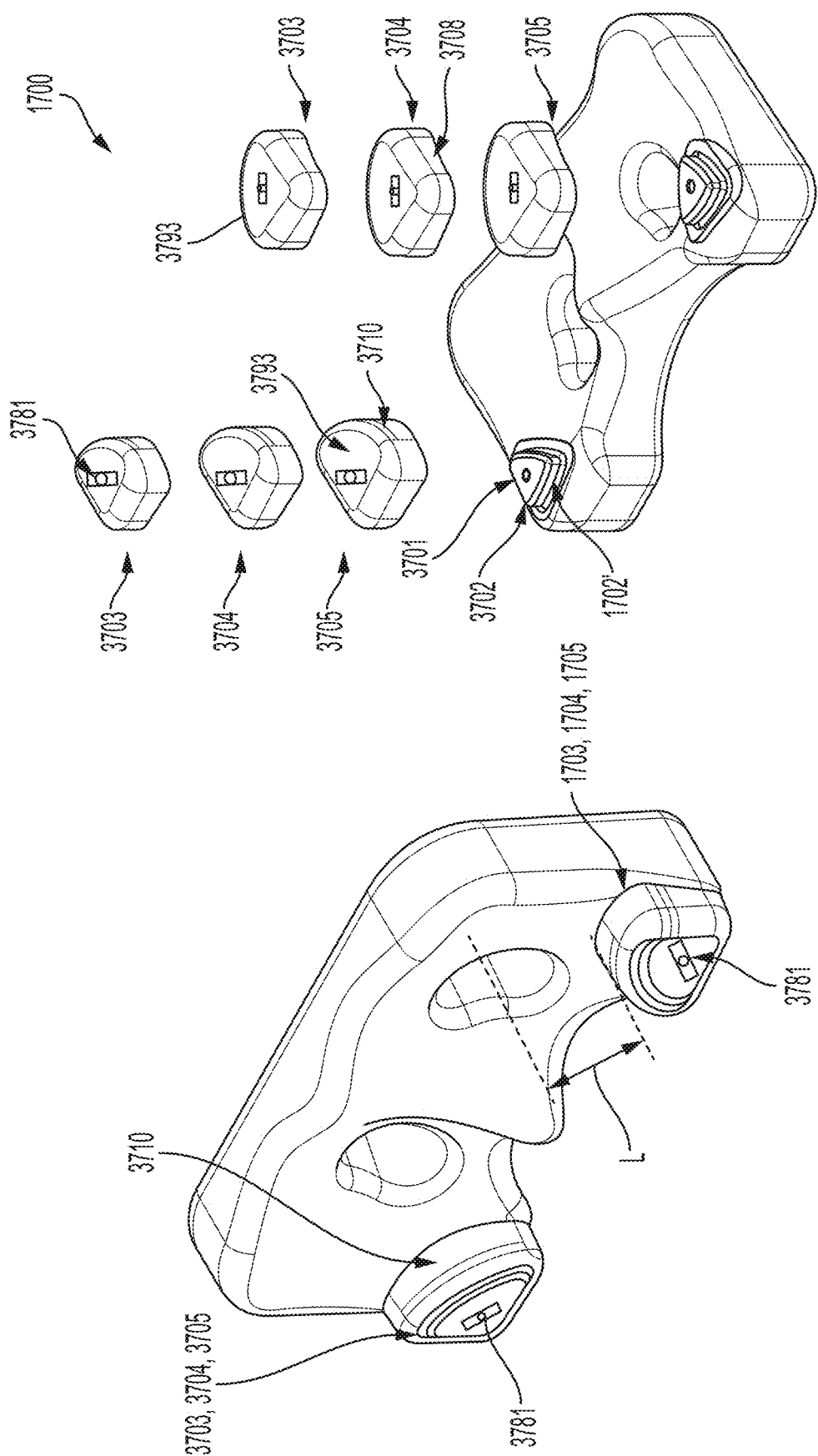

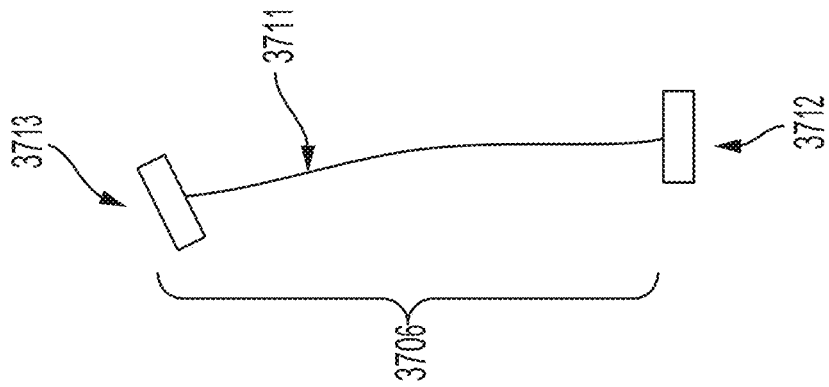
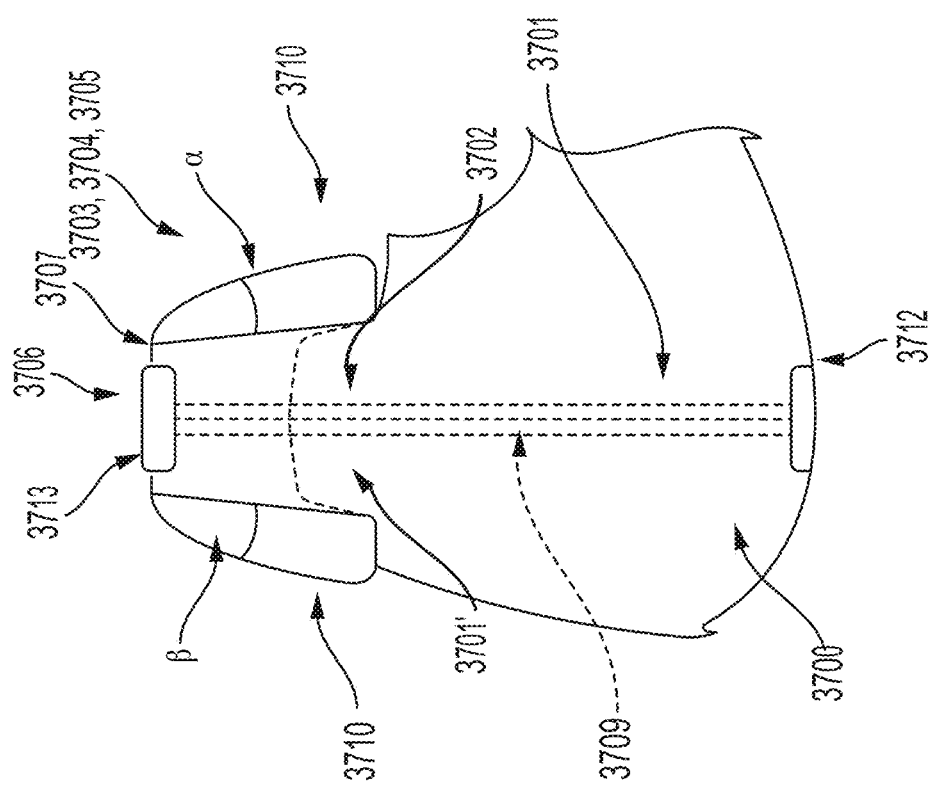

METHOD, SYSTEM, AND APPARATUS FOR FACILITATING POSITIONING A PERSON IN LATERAL SNIFF POSITION

PRIOR APPLICATIONS

This Application claims priority to and the benefit of U.S. Provisional Application No. 62/861,859 filed on Jun. 14, 2019, U.S. Provisional Application No. 62/836,558 filed on Apr. 19, 2019, U.S. Provisional Application No. 62/824,203 filed on Mar. 26, 2019, U.S. Provisional Application No. 62/772,492 filed on Nov. 28, 2018, and U.S. Provisional Application No. 62/769,869 filed on Nov. 20, 2018. The entire teachings of these earlier applications are incorporated herein by reference.

TECHNICAL FIELD

The present disclosure relates to an apparatus (herein also referred to as a pillow or a head-positioning apparatus) for airway management that can provide support for the head and neck of a user while aligning the oropharyngeal, laryngeal, and tracheal axes of the human head and neck for airway management in the lateral decubitus position.

BACKGROUND

Many attempts have been made to design and improve pillows in order to reduce snoring or other obstructive breathing, and/or to facilitate intubation. Obstructive breathing can occur during sleep, or sedation, most commonly in the supine position due to the effects of gravity on the tongue. Pillows have been developed to reduce airway obstruction in the supine position. For example, U.S. Pat. No. 5,048,136 discloses such a pillow. Sleeping in the lateral decubitus position (wherein person sleeps on their side) has been also shown to help reduce, but not eliminate, obstructive breathing during sleep. Because of this known fact, pillows that facilitate sleeping in the lateral position have been developed to keep the airways open including those disclosed in US. Pat. Nos. 7,908,691 B2 and 8,677,531B2 and in provisional patent 62/769,869.

As described in U.S. Pat. No. 8,677,531B2, one method of opening the airways includes aligning the oropharyngeal, laryngeal and tracheal axes by placing the patient into the "sniff" position, which has been determined to be the most effective positional method for improving the patency of the airway and therefore enhancing the volume and smoothness of the flow of air or oxygen into the patient and the flow of carbon dioxide out.

However, there are shortcomings with conventional methods of managing air and oxygen flow through an individual's airway. For example, the conventional methods fail to accommodate the following: varying patient morphologies (for example variances in shoulder to neck distance or neck and jaw length), differing mattress compression caused by variations in user weight, and differences in mattress indentation force deflection (a measure of softness or firmness of a pillow or sleep mattress), all of which can prevent a patient from sleeping comfortably. The method described in the referenced patent also allows a sleeping or awake individual (e.g., a patient) to easily move from the lateral decubitus position into the supine position wherein the alignment of the axes of airways is lost and the luminal diameter of the airways is diminished.

Thus, a need exists for a pillow that is more effective in promoting restful sleep while aligning and/or increasing the diameter of the upper airways (those proximal to the cartilaginous trachea).

BRIEF SUMMARY

Embodiments disclosed herein address and overcome one or more of the above shortcomings and drawbacks, by providing methods, systems, and apparatuses for positioning and maintaining the user comfortably into the lateral sniff position. Further, embodiments disclosed herein include features that allow adjustments for differing patient morphologies, such as varying neck to shoulder measurements for shoulder depth, for differences in patient weight and mattress deformation (affecting required pillow height), for the use of ventilation devices (such as CPAP or BiPAP), for comfortable disposition of the arm during sleep and for varying the chin angle (head size, patient height, shoulder width, patient weight, chin length, range of motion (or lack thereof), of the patient's neck), thus allowing the patient to sleep in the most comfortable position with optimal alignment of the oropharyngeal, laryngeal, and tracheal axes.

In one aspect, an apparatus for supporting the neck and the head of a user for airway management is disclosed. The apparatus can include a top section with a top surface (upper surface) and a bottom mating surface (lower surface), where the top surface is located on a side opposite the bottom mating surface and a bottom section with a bottom surface and a top mating surface. The top section mating surface can be configured to fit snuggly onto the bottom section mating surface, where the indentation deflection load (IDL) of one section can be greater than the IDL of the second section; where the bottom mating surface of the top section and top mating surface of the bottom section fit snuggly together through opposing interfaces and where the opposing interfaces are of sufficient height and depth to prevent the sections from sliding or moving relative to one another; where the height of either the top or bottom sections can vary such that differing user neck and shoulder lengths can be accommodated; where a cut-out on a portion of the pillow, parallel to the user's body accommodates the lateral extension and comfortable anatomic positioning of both arms, and especially the dependent arm, of the user.

In some embodiments, the top section of the pillow can include a removable and replaceable segment that can be removed to provide access to the user's mouth and nose, e.g., to accommodate a ventilation device. Further, in some embodiments, the pillow can include a left head-receiving portion and a right head-receiving portion for receiving and supporting a user's head in the left and the right lateral decubitus position. A ridge or raised surface can separate the left head-receiving portion from the right head-receiving portion. The ridge or raised surface between the first and second head-receiving portions assists in preventing and/or inhibiting the user from inadvertently assuming (or consciously attempting) the supine position while also positioning the user's head into the proper lateral and sniff position or lateral sniff ramp position. In some embodiments, the ridge can have a non-uniform height with a maximum height in a range of about 1 to about 4 inches, e.g., 2.5 inches to about 3.5 inches, relative to the bottom of the head-receiving portions. A left neck supporting surface is connected to the left head-receiving surface and a right neck supporting surface is connected to the right head-receiving surface, where the neck supporting surfaces are dimensioned to support the user's neck.

The top section of the pillow can further include at least one chin support for facilitating the placement of a user in a lateral decubitus position. In some such embodiments, the height of the chin support can vary between 1 inch and 4.5 inches so that the topmost surface of the chin support is not higher than user's ear aperture level to the top of the epicanthus or outer corner of the down side eye, thus preventing claustrophobia tendencies on user's part and/or obstruction of the user's visual axis and/or application of an excessive pressure to the sensitive parts of the eye itself. The surfaces of both head-receiving portions, the ridge or raised surface between the head-receiving portions, and the chin support can collectively align the user's oropharyngeal, laryngeal and tracheal airways in the sniff lateral position with the user's head received in one of the head-receiving portions. In many embodiments, the chin support has a compound slope on its inner surface which can be the mirror image of the compound slope of the neck and platysmal surface of the side of the user's neck allowing the inner surface to comfortably receive the lateral platysmal surface.

In some embodiments, the inner surface of the chin support can be substantially perpendicular to the base of the pillow thus forming an angle with the top surface of the chin support (that surface being parallel with the base of the pillow or supporting surface) in a range of about 80° and 100° (this range of angles being referred to herein as being substantially perpendicular). Further, in some embodiments, the inner surface of the chin support can exhibit a compound curvature that begins at the side of the chin support parallel to the side of the pillow and ends at the side of the chin support that is parallel to the front side of the pillow, where the compound curvature exhibits gradient angles of between 20° and 60°. In some embodiments, this inner surface having a compound curvature receives the platysmal surface of the neck helping position the patient comfortably in the sniff position.

In some embodiments, the recess neck openings (herein also referred to as neck channels) can be angled to position the user's head and neck in an anterior direction, thus allowing for lower neck flexion. Additionally or alternatively, the chin support and ear aperture triangulate the user to permit the head and upper neck to be in an extension position and to be tilted at an angle relative to the cervical spine of between 10° and 30°.

In some aspects, an apparatus for supporting the neck and head of a user for airway management can include one or more head-receiving portions shaped and dimensioned to support the side of a user's head, a chin support that includes an adjustable chin positioner that can be adjusted to support the chin of a user, and a neck supporting surface shaped and dimensioned to support a side of the user's neck; wherein the depth of the recessed surface corresponding to the user's chin can be approximately 2 inches, the depth of the recessed portion of the head-supporting surface can be approximately 3 inches and the depth of a recessed portion of the head supporting surface corresponding to the back of the user's head can be approximately 3 inches, and where the adjustable chin positioner can allow the user's Occipito-Atlanto-Axial joint to be adjusted between 5° and 30°, e.g., in a range of between 18-24°, which can be clinically significant. This can allow placing the user in the anatomic sniffing position providing greater occipito-atlanto-axial extension compared to simple head extension.

In one aspect, an apparatus for supporting the head and neck of a user for airway management is disclosed, which comprises a top surface including at least one head-receiving portion configured and dimensioned for receiving and supporting a user's head, and at least one recess neck opening for supporting a user's neck when the user's head is received in the head-receiving portion. The apparatus further includes at least one chin support protruding above the top surface and configured for facilitating the placement of the user in a sniff position when the user's head is received in the head-receiving portion. The chin support can include a top surface segment and a lateral surface segment, where at least a portion of the lateral surface segment of the chin support extends from the top surface segment thereof to the at least one recess neck opening.

The head-receiving portion, the recess neck opening and the chin support can be positioned relative to one another and dimensioned such that when the user is in a lateral decubitus position with the head received by the head-receiving portion, oropharyngeal, laryngeal and tracheal axes are substantially aligned. Further, the head-receiving portion, the recess neck opening and the chin support can be positioned relative to one another and dimensioned such that when the user is in a lateral decubitus position with the user's head received by the head-receiving portion, the user's upper cervical spine experiences an extension in a range of about 5 to about 20 degrees and the user's lower cervical spine experiences a flexion in a range of about 5 to about 15 degrees.

In some embodiments, a maximum height difference between the top surface segment of the chin support and the bottom of a respective head-receiving portion is in a range of about 1 inch to about 5 inches, e.g., in a range of about 2 inches to about 4 inches. In many embodiments, the maximum height of the chin support is selected so as not to be higher than the zygomatic arch of a user's facial bones.

In some embodiments, at least a portion of an inner lateral surface of the chin support (e.g., a portion of the lateral surface of the chin support facing a head-receiving portion) exhibits a compound slope that varies along two orthogonal directions. For example, the slope of such a lateral portion of the chin support can show variations in a downward direction toward the head-receiving portion as well as along a direction substantially orthogonal to such a downward direction. Such variations of the slope along any of those directions can be, for example, in a range of about 20 degrees to about 90 degrees.

In some embodiments, the top surface segment of the chin support can be downwardly slanted toward a lateral side of the top surface of the top section of the pillow. In other embodiments, the top surface segment of the chin support can be flat.

In other embodiments the top surface of the chin support can be substantially perpendicular to the inner surface of the chin support where the angle between the surfaces can range between 80° and 90° (this angle range is herein referred to as being "substantially perpendicular").

In some embodiments, the neck recess opening can be in the form of a curved ridge. In some embodiments, the recess neck opening can be curved and characterized by a varying radius of curvature from one end thereof to the other. By way of example, the radius of curvature of the recess neck opening can vary between about 1 inch to about 4 inches, e.g., in a range of about 2 and 3 inches.

In some embodiments, the apparatus for supporting the head and neck of a user can include a left and a right head-receiving portion, which are separated from one another by a ridge. In some such embodiments, the apparatus can further include a left and a right recess neck opening, which are also separated by the ridge. Further, in some such embodiments, the apparatus includes a left chin support and a right chin support for facilitating the placement of the user in a sniff position when the user's head is received in the left and right head-receiving portions.

In some embodiments, the chin support can further include an adjustable chin positioner that can be moved to adjust the configuration of the chin support for accommodating different users. In other words, the adjustable chin positioner can allow configuring the chin support so that it can accommodate differing user morphologies and place such users in a sniff position.

The adjustable chin positioner can be implemented in a variety of different ways. For example, in some embodiments, the adjustable chin positioner can be implemented by providing an opening in the inner lateral surface of the chin support, which can at least partially extend from the inner lateral surface toward an outer lateral surface of the chin support. The adjustable chin positioner can include a post that is configured to be movably positioned within the opening formed in inner lateral surface of the chin support. The post can extend between a proximal surface and a distal surface. A portion of the lateral surface of the chin support surrounding the opening can be recessed relative to the opening to allow the post to swivel about the opening. When the post is fully engaged within the opening, the proximal surface of the post is substantially flush with the inner lateral surface of the chin support. In some embodiments, the proximal surface of the post has a compound curvature that in combination with the rest of the lateral surface of the chin support provides a suitable compound curvature for comfortably positioning a user in a sniff position. In some such embodiments, the compound curvature of the proximal surface of the post can complement the compound curvature of the lateral surface of the chin support such that when the post is fully engaged within the opening with the proximal surface thereof substantially flush with the inner lateral surface of the chin support, the combination of the proximal surface of the post and the remainder of the inner lateral surface of the chin support forms a substantially contiguous surface.

As noted above, the post can be moved in and out of, and/or swivel about, the opening provided in the chin support to provide adjustments for accommodating different users. In some embodiments, a plurality of ridges can be provided on the inner surface of the opening to provide multiple settings for the extension of the post outside of the opening.

In some embodiments, the adjustable chin positioner can be implemented by providing a groove on a surface of the chin support, e.g., on or in proximity of the top surface segment of the chin support, where the adjustable chin positioner includes a chin support block that can be movably engaged with the groove to move back-and-forth along the groove. In some such embodiments, the bottom surface of the block comprises a sawtooth surface and the groove includes a mating sawtooth surface for engaging with the sawtooth surface of the block. In some embodiments, the groove can have a curved profile, e.g., it can extend from a front end of the top surface to a lateral side thereof.

In other embodiments, a chin support according to the present teachings can include an adjustable chin support block. More specifically, such a chin support can include a chin support structure in a surface of which a plurality of mount holes are formed, e.g., cut or molded in a top surface of the structure, for receiving one or more pegs associated with a chin support block. The use of a plurality of mount holes allows moving the chin support block in a desired direction (towards or away from a user's neck and chin) so as to accommodate various user morphologies.

In other embodiments, a chin support according to the present teachings includes a raised chin support structure that is configured to removably and replaceably engage with an adjustable and removable chin support block (which is herein referred to as an adjustable chin positioner). The raised chin support structure includes a through hole that extends from a top surface thereof to a bottom surface of the apparatus. The bottom surface of the apparatus includes a slot that contains the bottom opening of the through hole, which extends along the chin support structure.

The chin support block can include a cavity that is configured and shaped for removable and replaceable engagement with the chin support structure. The chin support block further includes a through hole that extends from a top surface thereof to its bottom surface. A slot is provided on the top surface of the chin support block that contains the top opening of the hole extending through the chin support block.

The chin support further includes a chin block mounting toggle that allows for removable and replaceable mounting of the chin block to the chin support structure. The mounting toggle includes a stretchable cord that is attached at each end thereof to a tab (herein also referred to as a handle), i.e., a bottom tab and a top tab. The mounting toggle can be engaged with the through hole provided within the chin support structure such that the bottom of the stretchable cord extends through the hole and the bottom tab is secured within the bottom slot provided on the bottom surface of the apparatus so as to secure the stretchable cord within the hole. The top tab extends outside the through hole and will engage with the chin support block in a manner discussed in more detail below.

Specifically, in order to attach the chin support block to the chin support structure, the top tab can be turned to be substantially parallel to the stretchable cord and then can be passed through the hole provided in the chin support block and be placed within the slot provided on the top surface of the chin support block. The tension in the stretchable cord, which is applied to the top and bottom tabs, secures the chin support block to the chin support structure. In order to remove the chin support block from the chin support structure, the top tab can be pulled and turned to be substantially parallel to the stretchable cord so as to allow disengaging the chin support block from the stretchable cord, thereby removing the chin support block from the chin support structure. In this manner, a variety of different chin support blocks having a variety of shapes and sizes (different lengths, widths, heights or combinations thereof) can be removably and replaceably attached to the chin support structure, thereby accommodating a variety of user morphologies.

In some embodiments, a chin support according to the present teachings can be formed of a molded or cut foam and can have a plurality of removable portions, which can be independently removed so as to adjust the chin support to different user morphologies. By way of example, the chin support can be formed of a plurality of sections that collectively provide a curved surface that can substantially conform to the platysmal surface of user's neck in order to support the user's neck. The sections can be coupled by indentations (perforations) that can allow peeling away the layers in succession as required to accommodate different users' morphologies.

In some embodiments, the ridge separating the right and the left head-receiving portions can be configured to inhibit inadvertent transitioning of a user from a lateral decubitus position to a supine position. For example, in some such embodiments, the ridge can have a maximum height in a range of about 1 inch to about 5 inches. In some embodiments, the ridge can have a non-uniform height. Such non-uniformity of the ridge's height can be selected so as to inhibit a user from moving from a lateral decubitus position to a supine position while ensuring that the ridge would not make the user uncomfortable. In some such embodiments, the ridge exhibits a greater height proximate a front side of the top surface relative to a backside thereof. For example the ridge can exhibit a height non-uniformity in a range of about 10% to about 300%.

In some embodiments, the maximum width of the ridge, which can be defined as the width of the portion of the ridge extending between the left and the right recess neck openings, can be, for example, in a range of about 3 inches to about 6 inches, e.g., in a range of about 4 to about 5 inches.

In some embodiments, each of the head-receiving portions has a downward-sloping surface, which extends from a top edge of the head-receiving portion to a bottom end thereof. In some embodiments, the surface of the head-receiving portion exhibits a varying slope across different segments thereof. In some such embodiments, the surface of the head-receiving portion can exhibit a compound slope characterized by variations of the slope along two orthogonal directions. For example, the slope of such a head-receiving surface can vary along a downward direction and also along a direction that is substantially orthogonal to the downward direction. In some other embodiments, the slope variation of the surface of a head-receiving portion can be only along one direction. Further, in other embodiments, a head-receiving portion may exhibit a single slope across the entire surface thereof.

By way of example, in some embodiments in which the apparatus includes a left head-receiving portion and a right head-receiving portion, the left head-receiving portion comprises a first segment 191 (FIG. 2D) positioned proximate a left side of the top surface, a second segment 192 positioned proximate a back side of the top surface, a third segment 193 positioned proximate the ridge 110, and a fourth segment 194 positioned proximate a front side of the top surface, where the third segment exhibits a steeper slope relative to the second segment, and the second segment exhibits a steeper slope relative to the first segment. Further, in some such embodiments, the right head-receiving portion comprises a first surface segment positioned proximate a left side of the top surface, a second surface segment positioned proximate a back side of the top surface, a third surface segment positioned proximate the ridge, and a fourth surface segment positioned proximate a front end of the surface, where the third surface segment exhibits a slope steeper than that of the second surface segment and the second surface segment exhibits a slope steeper than that of the first segment. In some embodiments, the variation of the slope across the surface of a head-receiving portion can be, for example, in a range of about 20 degrees to about 90 degrees.

In some embodiments, the apparatus for supporting the head and neck of a user for airway management can include at least one ear opening (also herein referred to as ear hole) that is disposed in at least one of the head-receiving portions, e.g., at the bottom of the head-receiving portion. The ear hole can be configured and dimensioned to at least partially receive a user's ear while the user is in a lateral decubitus position with the user's head received and supported in the head-receiving portion. By way of example, the ear hole can have a maximum cross-sectional dimension, e.g., a diameter when the cross-sectional profile is circular, in a range of about 1 to about 5 inches, e.g., in a range of about 2 inches to about 4 inches. The ear hole can have a variety of different cross-sectional profiles, such as, circular, elliptical, polygonal, etc. By way of example, the ear hole can have a substantially cylindrical profile. In some such embodiments, the lateral surface of each ear hole can exhibit a convex profile. The ear hole can extend from the top surface to an opposed bottom surface of the apparatus.

In some embodiments, the ear hole is positioned and dimensioned so as to at least partially muffle or reduce noise generated by the apparatus, e.g., due to compression of the apparatus by a user's head, and/or any other noise which is experienced by the user while the user's head is maintained in the at least one head-receiving portion.

In some embodiments, rather than an ear hole, the apparatus can include an indentation at the bottom of a head-receiving portion for accommodating at least a portion of a user's ear.

In some embodiments, at least a portion of a lateral surface of the ear hole can be covered with a ventilation material. By way of example, the ventilation material can be in the form of a mesh. Some examples of suitable ventilation materials include, without limitation, silk, cotton, wool, polyester or combinations thereof.

In some embodiments, the top surface comprises at least one removable and replaceable portion such that removal of the removable portion allows access to the user's nose and mouth when the user's head is received in the at least one head-receiving portion in a lateral decubitus position. By way of example, the removable portion can be positioned between the head-receiving portion and a lateral side of the top surface. By way of example, the removal of the removable portion can allow the user to use a therapeutic and/or monitoring and/or diagnostic device, such as a CPAP device, while using the apparatus in a lateral decubitus position.

In some embodiments, the apparatus can further include a cover for at least partially enclosing the apparatus. In some such embodiments, a portion of the cover can extend through the ear hole to be fastened to another portion of the cover for securing the cover to the apparatus. In some embodiments, the cover can be treated with an antimicrobial or an anti-pest compound to reduce bacterial growth or inhibit the presence of pests, such as Cimex hemipterus, that can sometimes infect bedding materials.

In some embodiments, the cover can have a snug fit onto matting features molded or cut into the bottom and top surface of the apparatus.

In some embodiments, the cover can have a pocket into which the adjustable chin support can be fitted. In other embodiments in which an adjustable chin support block includes one or more pegs for fitting into at least one mounting hole of the chin support structure, the chin support pocket can have one or more holes corresponding to one or more pegs formed or cut into the bottom surface of the chin support block. By way of example, the one or more holes can correspond to one or more holes in the chin block structure that are configured to receive the one or more pegs associated with the adjustable chin block.

In some embodiments, the cover can be made of a natural material such as silk, cotton, wool, linen or any combination of such a material. In other embodiments, the cover can be made of synthetic material such as a polyester weave, or alternatively it can be made of a combination fabric that includes two or more of these types of materials.

In some embodiments, the apparatus can further include a second cover that at least partially encloses the apparatus including the first cover. In some embodiments, the second cover can extend through openings in the first cover in order to extend through the apparatus ear hole to be fastened to another portion of the second cover for securing the second cover to the apparatus and around the first cover. In some embodiments the second cover can be configured, or sized, to receive foam inserts or wedges that fit between the first cover and the second cover.

In some embodiments the portions of the second cover that surrounds the apparatus ear holes may have marking or designs that indicate where, and in which direction, the user's head is placed. Such markings or designs may be printed, sewn, or screened onto the second cover by mechanical or chemical means.

In some embodiments the second cover can be made of a natural material such as silk, cotton, wool, linen or any combination of such a material. In other embodiments, the second cover can be made of synthetic material such as a polyester weave, or alternatively it can be made of a combination fabric containing two or more of these materials.

In some embodiments the apparatus can include a third cover that at least partially encloses the apparatus including the second and first cover. In some embodiments the third cover can extend through openings in the first and second covers in order to extend through the apparatus ear hole to be fastened to another portion of the third cover for securing the third cover to the apparatus and around the first and second cover.

In some embodiments the third cover can be made of a natural material such as silk, cotton, wool, linen or any combination of such a material. In other embodiments, the third cover can be made of synthetic material such as a polyester weave, or alternatively it can be made of a combination fabric of two or more materials.

An apparatus according to the present teachings can be fabricated using any suitable material, including a variety of different polymeric materials. Some examples of such materials include, without limitation, polyurethane, latex polyurethane, viscoelastic polyurethane, memory foam, polyethylene, and EVA (ethylene-vinyl acetate), among others. In some embodiments, the apparatus is formed of a foamed material. In some embodiments, the density of the foamed material from which the apparatus is formed can be, for example, in a range of about 1.5 to about 5 pound/ft$^3$.

In a related aspect, an apparatus for supporting the head and neck of a user for airway management is disclosed, which comprises a top section, and a bottom section configured for removably and replaceably engaging with the top section. The top section includes a left portion separated from a right portion by a ridge. Each of the left and right portions includes a head-receiving cavity for receiving and supporting a user's head, a recess neck opening for supporting a user's neck when the user's head is received in the head-receiving cavity, and a chin support for facilitating the placement of the user in a sniff position when the user's head is received in the head-receiving cavity in a lateral decubitus position.

In some embodiments, the head-receiving cavity, the recess neck opening and the chin support of each of the right and left portions are positioned relative to one another and dimensioned such that when the user is in a lateral decubitus position with the user's head received by the head-receiving portion, the user's oropharyngeal, laryngeal and tracheal axes are substantially aligned. Further, in some embodiments, the head-receiving cavity, the recess neck opening and the chin support of each of the left and right portions are positioned relative to one another and dimensioned such that when the user is in a lateral decubitus position with the user's head received by the head-receiving cavity, the user's upper cervical spine experiences an extension in a range of about 5 to about 20 degrees and the user's lower cervical spine experiences a flexion in a range of about 5 to about 15 degrees.

The top section can include a top surface, a bottom surface opposed to the top surface, a front surface, a back surface opposed to the front surface, a left side surface, and a right side surface. Further, the bottom section can include a top surface shaped to matingly engage with the bottom surface of the top section, and a bottom surface opposed to the top surface.

The top surface of the top section includes the head-receiving cavities, the recess neck openings and the chin supports. In some embodiments, each recess neck opening can be in the form of a ridge that extends from a respective chin support to the ridge separating the left and right portions of the top section.

In some embodiments, at least one of the head-receiving cavities includes an indentation at a bottom end thereof for receiving at least a portion of a user's ear when the user's head is received in the head-receiving cavity in a lateral decubitus position. In some other embodiments, at least one of the head-receiving cavities includes an ear hole for receiving at least a portion of a user's ear. In some embodiments, such an ear hole extends from the top surface of the top section to the bottom surface thereof.

In some embodiments, the bottom section includes two ear holes that extend from a top surface to a bottom surface thereof, where the ear holes in the bottom section are positioned so as to be substantially aligned with the ear holes formed in the top section upon engagement of the top section with the bottom section, where "substantially aligned" as used herein with reference to the ear holes in the top and the bottom sections means that the planes of the inner surfaces of the ear holes in the top and the bottom sections are aligned to within at least 0.125". In other words, a misalignment of such surfaces, if any, is at most 0.125".

Each of the chin supports protrudes above the top surface of the top section. Further, each of the chin supports provides a cavity for receiving a respective protruding element of the bottom section. The chin supports can be molded or cut into the apparatus or they may be adjustable and/or removable to accommodate differing user morphologies, as discussed in more detail below. In some embodiments, each chin support can include a lateral surface segment and a top surface segment, where at least a portion of an inner portion of the lateral surface segment (i.e., at least a portion of the lateral surface segment facing a head-receiving portion) exhibits a compound slope that varies along two orthogonal directions. For example, the gradient angles associated with the compound slope can vary between 20° and 60°. In some embodiments the each chin support can include an inner lateral surface segment and a top surface segment where the two surfaces are "substantially perpendicular" to each other. In particular, the lateral surface segment and the top surface segement can form an angle in a range between about 80° and about 100° relative to one another. In some embodiments this inner surface of the chin support exhibits a compound curvature that begins at the side of the chin support parallel to the side of the pillow and ends at the side of the chin support that is parallel to the front side of the pillow with gradient angles varying between about 20° and about 60°. In some embodiments, such a compound curvature supports and receives the platysmal surface of the neck helping position the patient comfortably in the sniff position.

Further, in some embodiments, the distance from the center of each ear hole to the inner surface of a chin support associated with that ear hole can be in a range of about 3 inches to about 6 inches, e.g., in a range of about 3 inches to about 4 inches, or in a range of about 4 inches to about 5 inches, or in a range of about 5 inches to about 6 inches. The distance between the center of each ear hole to the inner surface of the respective chin support can be selected based, for example, on the anatomical features of a user. Some anatomical variables that can determine this distance can include, for example, the overall size of the head, the mandibular ramus and body lengths, the neck length and the range of motion (ROM).

In some embodiments, at least one of the left or the right chin support can include an adjustable chin positioner. The adjustable chin positioner can be implemented in a variety of different ways, such as those discussed above.

In some embodiments, the front surface of the top section includes a recess for receiving and supporting a user's shoulder. Each shoulder-receiving recess can extend between a respective chin support and the ridge separating the left and the right portions of the top section. In some embodiments, the ratio of the width to the depth of each shoulder-receiving portion, as defined further below, can be in a range of about 1.5:1 to about 6:1. In some embodiments, the width of each shoulder-receiving section can be, for example, about 6 inches to about 8 inches, and the depth of each shoulder-receiving portion can be, for example, in a range of about 1 inch to about 12 inches.

Further, the bottom section can include a respective shoulder-receiving recess such that when the top section is engaged with the bottom section, the top and bottom recesses cooperatively provide shoulder supporting surfaces for left and right lateral decubitus positions.

In some embodiments, the top section exhibits a hardness characterized by an IDL (indentation-deflection-load) value in a range of about 12 to 50, e.g., in a range of about 20 to about 40. Further, in some embodiments, the hardness of the top section is different from the hardness of the bottom section. By way of example, the difference between the hardness of the top and the bottom sections can be at least about 0.5 IDL, e.g., in a range of about 0.5 IDL to about 2 IDL.

In some embodiments, the ridge separating the left portion from the right portion is configured to inhibit involuntary transitioning of the user from a lateral decubitus position with the user's head received in one of the head-receiving cavities into a supine position. In some embodiments, the ridge can include a cavity into which a mating protrusion provided on the top surface of the bottom section can be inserted upon engagement of the bottom section of the apparatus with the top section.

In some embodiments, the recess neck opening and the chin support of at least one of the left and right portions are positioned relative to one another and dimensioned such that if the user moves from a lateral decubitus position to a supine position with the user's occipital lobe within the head-receiving cavity, the user remains in a sniff position.

In some embodiments, at least one of the right and left portions of the top section (and optionally the bottom section of the apparatus) comprises a removable and replaceable segment such that removal of the segment allows access to the user's nose and mouth when the user's head is received in a respective head-receiving cavity in a lateral decubitus position.

In another aspect, an apparatus for supporting the head and neck of a user for airway management is disclosed, which includes a polymeric block having a top surface, a bottom surface, a right surface, a left surface, a front surface and a back surface. At least one head-receiving cavity is formed in the top surface for receiving and supporting a user's head. Further, at least one recess neck opening is provided on the top surface for supporting a user's neck when the user's head is received in the head-receiving cavity. The apparatus further includes a chin support for facilitating the placement of the user in a sniff position when the user's head is received in the head-receiving cavity, where the chin support protrudes above the top surface at a maximum height relative to the bottom of the top surface in a range of about 2 to about 4 inches.

In some embodiments, the head-receiving cavity, the recess neck opening and the chin support are positioned relative to one another and dimensioned such that when the user is in a lateral decubitus position with the head received by the head-receiving cavity, oropharyngeal, laryngeal and tracheal axes are substantially aligned.

In some embodiments, the head-receiving cavity can exhibit a compound slope.

In some embodiments, the above apparatus can include a left head-receiving cavity and a right head-receiving cavity that are separated from one another by a ridge. In some such embodiments, the ridge can have a maximum height in a range of about 1 to about 4 inches. Further, in some such embodiments, the ridge can have a non-uniform height with the height decreasing from a portion proximate the front surface of the apparatus to a portion proximate the back surface of the apparatus.

In some embodiments, the polymeric block can include a portion that is removable and replaceable such that its removal can provide access to a user's mouth and nose while the user is in the lateral decubitus position with the user's head received in the head-receiving cavity.

In some embodiments, the recess neck opening can have a radius of curvature in a range of about 1 inch to about 4 inches.

In some embodiments, the apparatus can include at least one shoulder-receiving recess for receiving and supporting a user's shoulder. In some such embodiments, the shoulder-receiving recess can have a width in a range of about 6 inches to about 18 inches.

In some embodiments, at least one of the right or the left side surface of the apparatus includes an arm cut-out for accommodating at least a portion of a user's arm as the user's head is received in at least one head-receiving portion of the apparatus. In some embodiments, each of the left and the right side surfaces of the apparatus includes an arm cut-out for accommodating at least a portion of a user's left or right arm, respectively, as the user's head is received in the head-receiving portion.

In some embodiments, the arm cut-out is positioned at an angle in a range of about 0° to about 45° relative to a center line of the top surface.

As discussed above, in some embodiments, the apparatus can include an ear hole that extends from the top surface of the apparatus to a bottom surface thereof. In some such embodiments, the apparatus includes a first cover for at least partially enclosing the apparatus such that at least an extension portion of the first cover extends through the ear hole to be fastened to a bottom portion of the cover. In some embodiments, the first cover can snuggly fit about the apparatus. For example, in some embodiments, the first cover can be treated with one or more anti-microbial agents and/or one or more anti-pest agents.

In some embodiments, the apparatus can include a second cover for at least partially enclosing the first cover; where an extension portion of the second cover extends through the ear hole via a passage provided by the extension portion of the first cover to be fastened to a bottom portion of the first and the second cover.

In some embodiments, at least one of the first and the second cover includes one or more directional markings for indicating the correct positioning of the user's head in at least one head-receiving portion of the apparatus.

In some embodiments, the second cover is configured to fit snuggly over the first cover. In some embodiments, the cover has one or more pockets that are sized and shaped to receive one or more removable and replaceable chin support blocks. In other embodiments, the first cover has one or more holes that are positioned so as to align with holes in the top surface of the apparatus that are opposite to, and align with, one or more mount posts disposed on the bottom surface of a removable and replaceable chin support block.

In some embodiments, the apparatus further includes a third cover for at least partially enclosing the second cover, where an extension portion of the second cover extends through the at least one ear hole via a passage provided by the extension portions of the first and second covers to be fastened to a bottom portion of any of the first, the second and third cover.

In some embodiments, the extension portion of any of the first, the second, and the third cover is attached to the bottom portion of any of the first, the second, and the third cover via any of one or more buttons, one or more zippers, sewing, or glue.

In some embodiments, any of the first, the second and the third cover comprises a natural and/or a synthetic fabric. In some embodiments, the natural fabric can include, for example, any of silk, cotton, wool, linen or a combination thereof. The synthetic fabric can include, for example, polyester, nylon, etc.

In some embodiments, the apparatus can include height-adjusting wedges or inserts that can be fitted or slid beneath the bottom surface of the apparatus. In some such embodiments, the height adjusting wedges or inserts can be made of visco-elastic materials that include, without limitation, polyurethane, latex polyurethane, viscoelastic polyurethane, memory foam, polyethylene, and EVA (ethylene-vinyl acetate), among others. In some embodiments, the apparatus is formed of a foamed material in others it is made from die cut materials. In some embodiments, the density of the material of the wedges and inserts, for example, can be in a range of about 1.5 to about 5 pound/ft$^3$. In some embodiments the height adjusting wedges, or inserts, can have an angle between the top surface and the bottom surface starting at the edge of such height adjusting inserts proximal to the front edge of the pillow ranging from about 15° to about 45° in order to elevate the user's back and head.

In some embodiments the bottom surface of the pillow can have an angle, relative to the back side of the apparatus, ranging between about 90° and about 120° in order to elevate the user's back and head.

In some embodiments, the height-adjusting wedges or inserts can have the same width and/or length of the bottom surface apparatus, while in other embodiments, the width of a height-adjusting wedge can be up to 4 inches shorter than the width of the bottom surface of the apparatus while the length of a height-adjusting wedge can be up to 4 inches shorter than the length of the bottom surface of the apparatus; such widths and lengths providing height adjustments and stability to the apparatus. In other embodiments, the width and length of a height-adjusting wedge can be up to 4 inches longer than the respective width and length of the bottom surface of the apparatus In some embodiments the height adjusting inserts can individually have a thickness, or height, of between 0.25 to 3 inches.

In some embodiments up to eight of the height adjusting inserts, of varying thickness and heights can be used with the apparatus.

In some embodiments a first height adjusting insert can be configured to match the contours of the bottom surface of the apparatus with holes that correspond to the recessed ear holes in the apparatus, such holes extending from the top surface of the height adjusting insert to the bottom surface of the height adjusting insert. In such an embodiment, the top of holes of the first height adjusting insert can extend between ½ inch and four inches above the top surface of the first height adjusting insert forming a flange that can be configured to fit snuggly into the recessed ear hole in the bottom surface of the apparatus. A second height-adjusting insert with holes corresponding to the holes on the bottom surface of the first height adjusting insert can be employed. This second insert may have holes extending between ½ inch to four inches above the top surface of the second height adjusting insert. It can be seen that additional height adjusting inserts can be configured with the same features as the first and second height adjusting inserts allowing for the use of unlimited stackable height adjusting inserts that fit into one another and/or into, and onto, the bottom surface of the apparatus. In some embodiments, the top surface of a height-adjusting insert can include a plurality of holes, e.g., three or more holes, that extend from the top surface of the height-adjusting insert to the bottom surface thereof. In some embodiments, the bottom surface of the height-adjusting inserts include a plurality of slots, each of which contains the opening of the one of the holes extending through the height-adjusting inserts. In some embodiments, such holes formed in a plurality of height-adjusting inserts can be positioned to be substantially aligned when the height-adjusting inserts are stacked. In some embodiments a chin support of a pillow according to the present teachings can include at least one through hole that can be substantially aligned with at least one hole formed in a wedge according to the present teachings, such that upon coupling of the wedge with the apparatus, the holes can be substantially aligned. In some such embodiments, a toggle mount comprising a stretchable cord and two handles attached to the two ends of the cord, can be passed through the holes in the wedge and the apparatus to couple to the two together. In some embodiments in which a chin support structure of a pillow according to the present teachings includes a through hole for removable and replaceable coupling to a chin support block, as discussed in more detail below, at least one of the holes formed in a wedge or insert can be aligned with the through hole formed in the chin support structure. In some such embodiments, a chin support block configured for mounting onto the chin support structure can also include a hole that can be substantially aligned with the hole in the chin support structure and in the wedge. The alignment of the holes allows using a toggle mount, such as that disclosed below, to removably couple the wedge and the chin block to the chin support structure.

In some embodiments in which an apparatus according to the present teachings is enclosed in first and second covers, the second cover can be sized so as to allow the insertion of at least one height-adjusting element (herein also referred to as a height-adjusting insert or wedge) between the second cover and the bottom surface of the apparatus. By way of example, the height-adjusting element can have a height in a range of about 0.25 inches to about 3 inches.

As noted above, in some embodiments, the height-adjusting element has a length and a width less than a respective length and width of the bottom surface of the apparatus. For example, any of the length and the width of the height-adjusting element can be equal to or less than about 70% of the length and/or the width of the bottom surface of the apparatus. In other embodiments, the height-adjusting element can have a length and/or a width that is substantially identical with a respective length and/or width of the bottom surface.

In some embodiments, the height-adjusting element comprises a visco-elastic material. Some examples of suitable visco-elastic materials include, without limitation, elastic polyurethane, memory foam, and ethylene-vinyl acetate.

In some embodiments, the height-adjusting element comprises a material density in a range of about 1.5 to about 5 pounds/ft$^3$.

In some embodiments, the bottom surface of the apparatus and a top surface of the height-adjusting element include interlocking mating features for removably and replaceably engaging the height-adjusting element to the bottom surface. By way of example, the interlocking mating features can be in the form of mating sawtooth surfaces.

In some embodiments, the at least one height-adjusting element comprises a plurality of stacked height-adjusting elements that can be removably and replaceably engaged in a pairwise fashion via opposed interlocking surfaces. In some embodiments, the interlocking surfaces can be in the form of mating sawtooth surfaces. In some embodiments, the plurality of stacked height-adjusting elements exhibit varying thicknesses. By way of example, the stacked height-adjusting elements can include 2 to 5 height-adjusting elements.

In a related aspect, an apparatus for supporting the head and neck of a user for airway management is disclosed, which comprises a top surface including at least one head-receiving portion configured and dimensioned for receiving and supporting a user's head, and at least one recess neck opening for supporting a user's neck when the user's head is received in the head-receiving portion, and an opposed bottom surface. At least one ear opening (e.g., an ear hole) is disposed in the head-receiving portion. In some embodiments, the ear opening extends from the top surface to the bottom surface while in other embodiments the ear opening extends only partially from the top surface to the bottom surface. A first cover at least partially encloses the apparatus such that at least an extension portion of the first cover extends through the ear hole to be fastened to a bottom portion thereof that covers at least a portion of the bottom surface of the apparatus. A second cover at least partially encloses the first cover. An extension portion of the second cover extends through the ear hole via a passage provided by the extension portion of the first cover to be fastened to a bottom portion of the first and/or the second cover.

In some embodiments, at least one of the first and the second cover is treated with at least one of an anti-microbial agent and/or an anti-pest agent.

In some embodiments, at least one of the first and/or the second cover can include one or more directional markings for indicating a correct positioning of a user's head in the head-receiving portion. Further, in some embodiments, the second cover is configured to snuggly fit over the first cover. In some embodiments, a third cover at least partially encloses the second cover, where an extension portion of the third cover extends through the at least one ear hole via a passage provided by the extension portions of the first and the second covers to be fastened to a bottom portion of any of the first, the second and the third cover.

The extension portion of any of the first, the second, and the third cover can be attached to a respective one of the bottom portions of any of the first, the second, and the third cover via any of one or more buttons, one or more zippers, sewing or glue, among other means.

In a related aspect, an apparatus for supporting the head and neck of a user for airway management is disclosed, which comprises a top surface providing a single head-receiving portion configured and dimensioned for receiving and supporting a user's head, and at least one recess neck opening for supporting a user's neck when the user's head is received in the head-receiving portion, and at least one chin support protruding above the top surface and configured for facilitating the placement of the user in a sniff position when the user's head is received in the head-receiving portion. The chin support can include a top surface segment and a lateral surface segment, where at least a portion of the lateral surface segment of the chin support extends from the top surface segment thereof to the at least one recess neck opening.

In some embodiments, the head-receiving portion, the recess neck opening and the chin support are positioned relative to one another and dimensioned such that when the user is in a lateral decubitus position with the user's head received by the head-receiving portion, oropharyngeal, laryngeal and tracheal axes are substantially aligned. In some embodiments, a maximum height difference between the top surface segment of the chin support and the top surface can be in a range of about 1 inch to about 4 inches. In some embodiments, at least a portion of the lateral surface segment of the chin support exhibits a downward slope toward the head-receiving portion. In some such embodiments, the downward slope of the at least a portion of the chin support varies in a range of about 90 degrees to about 20 degrees. In some embodiments, the at least a portion of the lateral surface segment of the chin support exhibits a compound slope. In some embodiments, the neck recess opening comprises a concave surface. The concave surface can have a radius of curvature in a range of about 1 inch to about 4 inches.

In some embodiments, an apparatus according to the present teachings can further include at least one chin support extending above the top surface. The chin support can include a raised chin support structure having a mounting surface, the chin support structure comprising a hole extending from a top surface thereof to a bottom surface of the apparatus, wherein the bottom surface of the apparatus comprises a slot containing a bottom opening of the hole. The chin support can further include a removable and replaceable chin support block having a cavity shaped and sized for mounting on the mounting surface of the raised chin support structure, the chin support block comprising a hole extending from a top surface to a bottom surface thereof, wherein the hole extending through the chin support block is positioned to be substantially aligned with the hole extending through the chin support structure when the chin support block is mounted onto the chin support structure, and wherein the top surface of the chin support block comprises a slot containing a top opening of the hole extending through the chin support block. The chin support can further include a chin support mounting toggle that extends through the holes in the chin support structure and the chin support block to allow removably securing the chin support block to the chin support structure. In some embodiments, one or more holes formed in the apparatus, the chin support structure, the chin support block and one or more height-adjusting inserts are substantially aligned such that the chin support mounting toggle can extend through the holes in these elements, thus allowing the chin support block and the height-adjusting insert(s) to be removably secured to the apparatus. In some embodiments, one or more holes in the top surface of the apparatus on a side opposite to at least one of the chin blocks, can extend through the apparatus and be substantially aligned with through holes formed in one or more height-adjusting insert(s). In such embodiments, a mount toggle can be inserted through such holes in the apparatus, and the height-adjusting insert(s), to replaceably and removably secure the height-adjusting insert(s) and the chin support block(s) to the apparatus.

In some embodiments, the chin support mounting toggle can include a stretchable cord, a top handle attached to top end of the stretchable cord, and a bottom handle attached to a bottom end of the stretchable cord. The top handle is configured for being received in the slot provided on the top surface of the chin support block and the bottom handle is configured for being received in the slot provided on the bottom surface of the apparatus.

The chin support block can include a top surface, an outer side surface, an inner side surface and a front surface. In some embodiments, the top surface is substantially orthogonal to at least one of the outer or the inner side surface of the chin support block. By way of example, the top surface of the chin support block can form an angle in a range of about 80° to about 100° with any of the inner or the outer side surface of the chin support block. Further, in some embodiments, the top surface of the chin support block forms an angle in a range of about 80° to about 100° with the front surface of the chin support block.

In some embodiments the inner side surface of the chin support exhibits a compound curvature. In some embodiments, the compound curvature can be characterized by different slopes along two orthogonal directions. In some embodiments, the compound curvature can be characterized by varying slopes in a range of about 20° to about 60°.

In a related aspect, a system for supporting the head and neck of a user for airway management is disclosed, which comprises an apparatus for supporting the head and neck of a user for airway management. The apparatus can include a top surface including at least one head-receiving portion configured and dimensioned for receiving and supporting a user's head, at least one recess neck opening for supporting a user's neck when the user's head is received in the head-receiving portion, and at least one chin support structure protruding above the top surface. The system can further include a plurality of chin support blocks having different sizes, each of the chin support blocks being configured for removable and replaceable coupling to the chin support structure.

In a related aspect, an apparatus for supporting the head and neck of a user for airway management is disclosed, which comprises a top surface including at least one head-receiving portion configured and dimensioned for receiving and supporting a user's head, at least one recess neck opening for supporting a user's neck when the user's head is received in the head-receiving portion, and a chin support structure protruding above the top surface and configured for removably and replaceably receiving a chin support block, the chin support structure having a top surface, a bottom surface, an outer side surface and an inner side surface. The top surface of the chin support structure can include two or more chin block mounting holes and the chin support block includes at least one mount post configured for engaging with each of the mount holes to allow adjusting position of the chin support block relative to the chin support structure. In some embodiments, the mount holes are cut or molded in the chin support structure.

In some embodiments, the outer surface of the chin support structure is substantially orthogonal to the top surface of the support structure. In some embodiments, the inner surface of the support structure forms an angle in a range of about 80° to about 100° with the top surface of the support structure.

Additional features and advantages of the invention will be made apparent from the following detailed description of illustrative embodiments that proceeds with reference to the accompanying drawings.

The accompanying drawings, which are incorporated herein and form part of the specifications, illustrate various embodiments of a pillow for facilitating the lateral sniff position and for facilitating airway management. Together with the descriptions the figures further serve to explain the principles of the pillow described herein and thereby enable a person skilled in the applicable arts to make the apparatus.

BRIEF DESCRIPTION OF THE DRAWINGS

FIGS. 10A, 10B, and 10C schematically depict another example of an adjustable chin positioner according to another embodiment;

FIG. 14AA schematically depicts another embodiment of a pillow according to the present teachings, which is enclosed within an inner cover and an outer cover;

FIG. 14BB is a plan view of the bottom surface of the top section of the pillow depicted in FIG. 14AA, illustrating the second cover fitting snuggly around the first cover;

FIG. 14CC shows a cut-away view along axis A-A of the embodiment depicted in FIG. 14BB;

FIG. 18A-2 is another a schematic side view of an apparatus for supporting the head and the neck of a user according to an embodiment;

FIG. 18C is a schematic perspective view of the apparatus depicted in FIG. 17A;

FIG. 18D is a schematic perspective view of the apparatus depicted in FIG. 17A; illustrating a plurality of chin support blocks that can removably and replaceably coupled to each of two raised chin block structures;

FIG. 18E schematically depicts section A-A from FIG. 18B;

FIG. 18F schematically depicts one embodiment of a mount toggle that can be employed in the apparatus of FIGS. 18A-18E for removably and replaceably coupling chin support blocks to each of the chin support structures and for supporting and coupling one or more height-adjusting inserts, such as those depicted in FIG. 16;

DETAILED DESCRIPTION

Figure 1A:
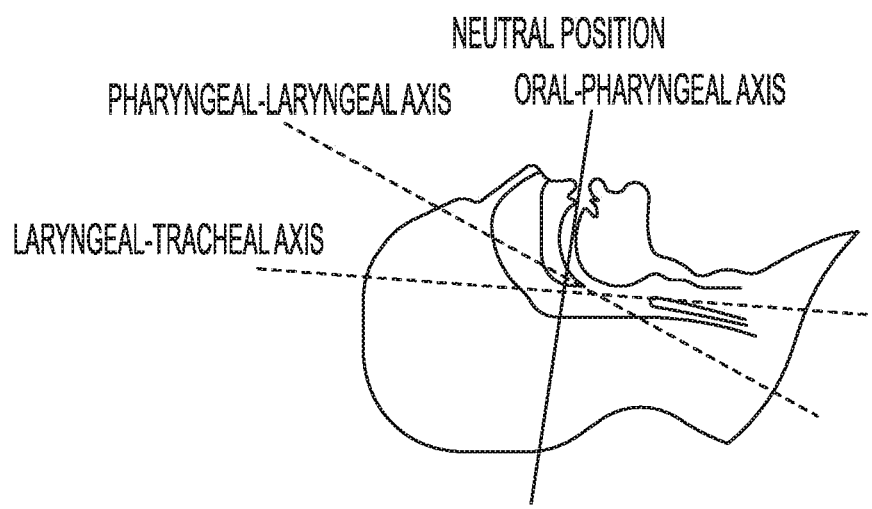
FIGS. 1A and 1B schematically depict an individual's airway passages in a supine position as well as in a sniff positioning, indicating better alignment of the airway passages in the sniff position.
Figure 1B:
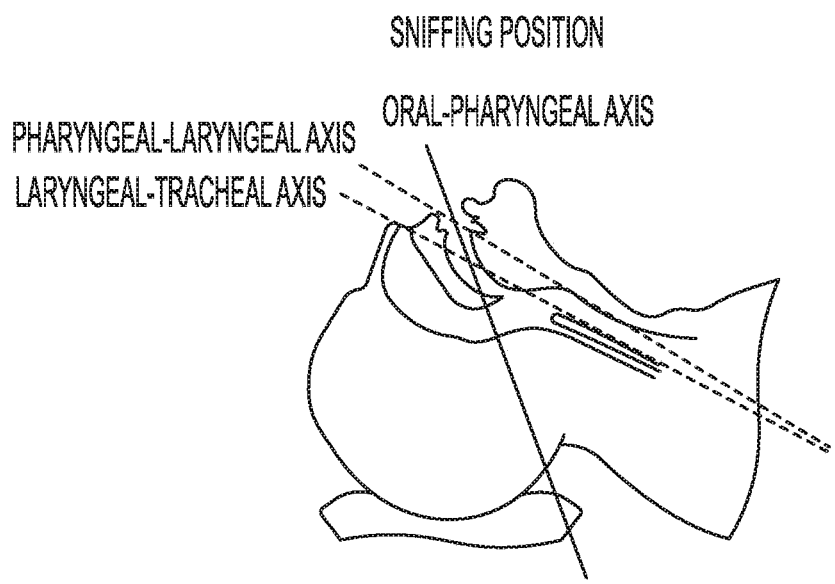

The present invention is generally directed to an apparatus for supporting the head and neck of a user for airway management. In many embodiments, an apparatus according to the present teachings can be used to place a user in a position in which the user's oropharyngeal, laryngeal and tracheal axes are substantially aligned, as discussed in more detail below. With reference to FIGS. 1A and 1B, in a neutral position, e.g., when a person is lying on his/her back on a flat surface with the occipital portion of the skull supported by that surface, the pharyngeal and laryngeal axes are not aligned and the oral axis is substantially normal to the supporting surface and can typically form an angle greater than about 80 degrees with the pharyngeal and laryngeal axes. In contrast, as shown schematically in FIG. 1B, in a so-called "sniffing" or "sniff" position, the pharyngeal and the laryngeal axes can be substantially aligned. The term "substantially aligned" as used herein in reference to airway axes, means a variation from perfect parallelism by at most 10 degrees. Further, the oral axis can be better aligned with the pharyngeal and laryngeal axes compared to the neutral position. For example, in a sniff position, the angle between the oral axis and any of the pharyngeal and/or laryngeal axes can be in a range of about 5 degrees to about 30 degrees.

Various terms as used herein have their ordinary meanings. As noted above, the term "substantially aligned," as used herein with reference to the airway axes, refers to an alignment that may deviate from a state of perfect alignment by at most 10 degrees. The term "about," as used herein, indicates a deviation of a numerical value by at most +/−10 percent.

Reference will be made in detail to embodiments of the present invention with reference to the accompanying figures, in which like reference numerals will indicate like elements. While specific configurations are discussed it should be noted that this is for illustrative purposes. The present invention relates to an apparatus (herein also referred to as a pillow, a head-positioning device or a head-positioning apparatus) for aligning the oropharyngeal, laryngeal, and tracheal axes and the extension of the Occipito-Atlanto-Axial joint, together with flexion of the lower cervical spine for airway management while the user is in the lateral decubitus position. Airway management involves adjusting the patient head and neck for improved ventilation and respiration. By improving the position of a user's head and neck, the user can experience improved sleep, rest, oxygenation and ventilation and avoid airway obstruction and airflow turbulence that may result, for example, in snoring. Although a pillow has been introduced to align the upper airways of the human head and neck while in the lateral decubitus position, it has certain shortcomings, which the current invention addresses. For example, a pillow according to the present teachings can accommodate differing user morphologies (for example neck to shoulder distance, which can vary widely even for individuals of the same height and weight), mattress compression (which varies with indentation force load and user's weight). Further, in some embodiments, a pillow according to the present teachings provides at least one arm cutout to allow disposition of the user's arm. Some embodiments are directed to pillows that can be used during sleep, while others are directed to pillows that can support the individual's neck during other activities.

Figure 2A:
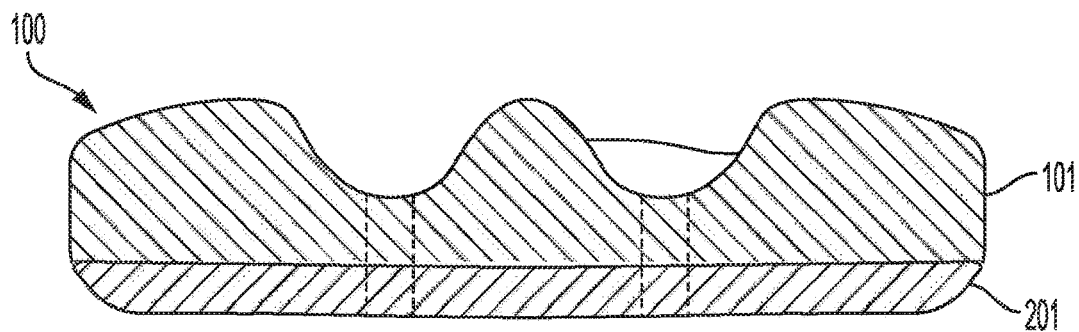
FIG. 2A is a schematic side view of a pillow according to the present teachings having a top section that is removably engaged with a bottom section.
Figure 2B:
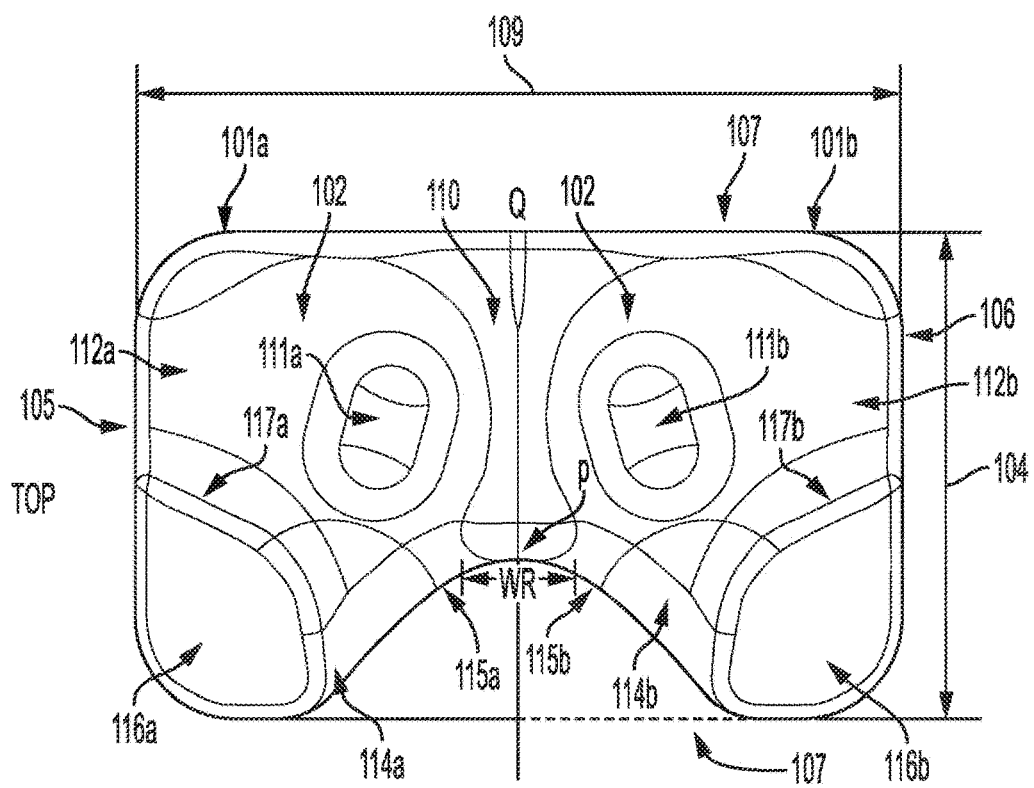
FIG. 2B shows schematic top and side views of the top section of the pillow depicted in FIG. 2A.
Figure 2B:
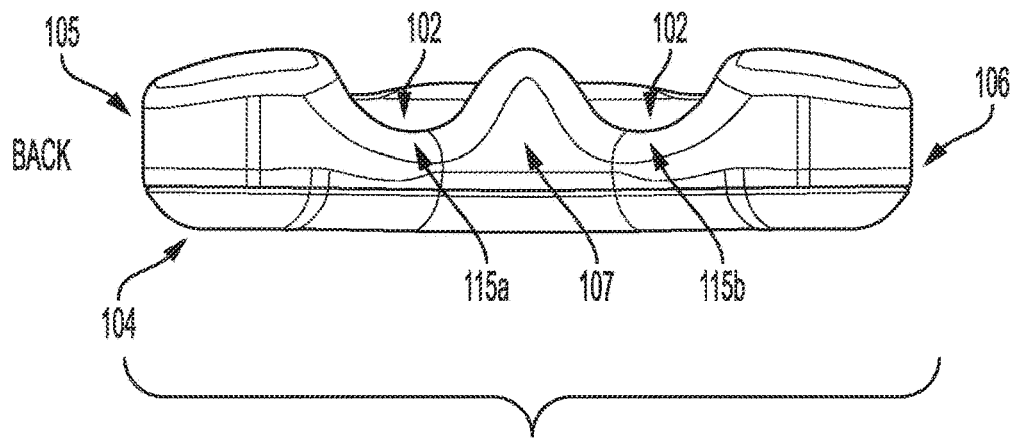
Figure 2C:
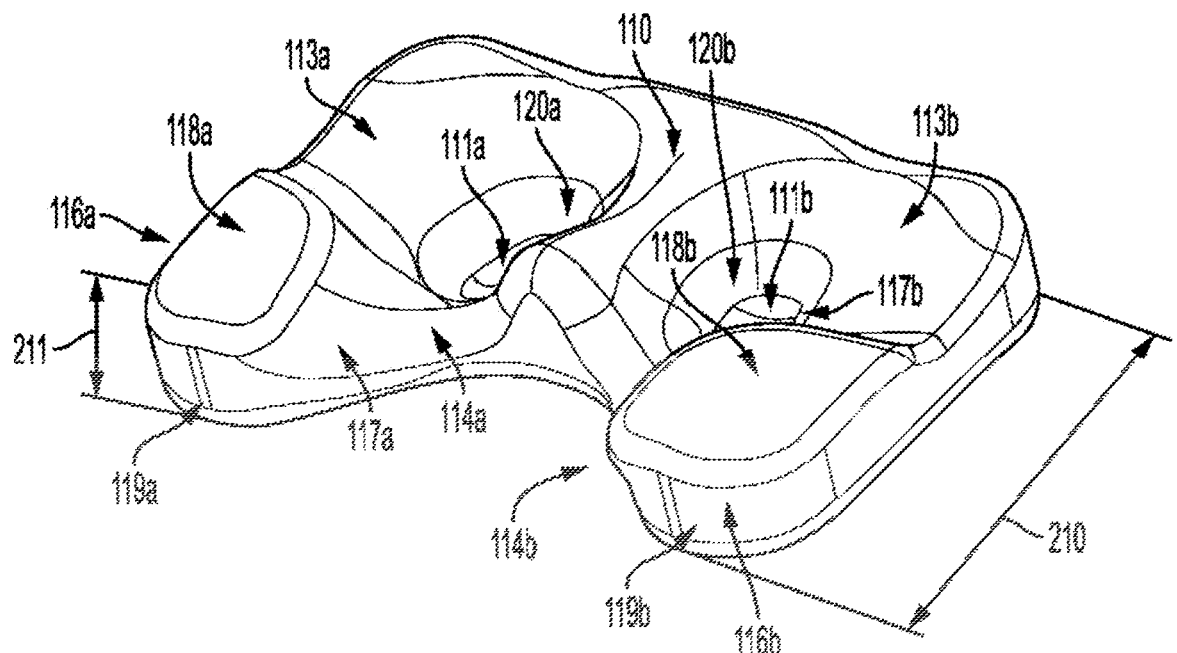
FIGS. 2C and 2D depict schematic views of the top surface of the top section of the pillow depicted in FIGS. 2A and 2B.

With reference to FIGS. 2A, 2B, a pillow 100 according to one embodiment of the present invention is disclosed, which allows left and right side sleeping for a user. The sizes of various features of the pillow 100 can be adjusted to accommodate many users' heights and weights. By way of example, the pillow can be sized for use by a 5'8", 180 lb. male or an average user. One of ordinary skill will appreciate that the dimensions of various features of the pillow 100 can be adjusted based on the present teachings to optimize the pillow for larger and smaller users.

In this embodiment, the pillow 100 includes a top section 101 and a bottom section 201, which can matingly engage with the top section 101 in a manner discussed in more detail below. The top section 101 includes a left portion (herein also referred to as left segment) 101a and a right portion (herein also referred to as right segment) 101b, which are separated from one another by a ridge or raised surface 110. As discussed in more detail below, the left portion 101a and the right portion 101b accommodate left and right lateral decubitus positions of the user. Further, as discussed in more detail below, the ridge or raised surface 110 can assist in aligning a user's head and prevent and/or inhibit the user from inadvertently assuming the supine position.

In this embodiment, the top section 101, which has a generally rectangular cross-sectional profile, extends axially from a top surface 102 to a bottom surface 104. Further, the top section 101 extends laterally along a width dimension 109 from a left side surface 105 to a right side surface 106 and along a length dimension 104 from a front surface 107 to a back surface 108.

In some embodiments, the height of the top section 101 of the pillow, defined as the maximum distance between its top surface 102 and its bottom surface 104 in uncompressed condition of the pillow, can be, for example, in a range of about 2 inches to about 6 inches, e.g., less than about 5.5 inches. Further, in some embodiments, the width dimension 109 and the length dimension 104 of the top section 101 can vary based on a population of users for whom the pillow is designed. By way of example, for the average user the length dimension 104 is about 16 inches and the width dimension 109 is about 27 inches.

With reference to FIGS. 2A, 2B, 2C and 2D, the top surface 102 is configured and dimensioned to accept the head and neck of a user in the right and left decubitus lateral positions. In particular, the top surface 102 includes a right head-receiving portion 112a and a left head-receiving portion 112b for receiving and supporting a user's head in the right and left lateral decubitus positions.

The top section 101 further includes left and right recess neck openings 114a/114b and left and right shoulder cut-outs 115a/115b for receiving and supporting a user's shoulder in left and right decubitus positions, respectively. In this embodiment, the shoulder cut-outs 115a/115b (herein also referred to as shoulder-receiving portions) are formed as curved portions of the front surface 107 of the top section. Further, the left and the right recess neck openings 114a/114b are in the form of curved ridges disposed, respectively, over the shoulder receiving portions (herein also referred to as shoulder cut-outs) 115a/115b.

In this embodiment, the head-receiving portions 112a/112b are formed by surface portions 113a and 113b of the top surface 102, respectively. The left head-receiving surface portion 113a is in the form of a downward-sloping surface that is circumscribed by a portion of the left side surface 105, a portion of the back surface 108, the inner lateral surface of a right chin support 116a (which is discussed in more detail below), the left recess neck opening 114a, and the ridge 110. Further, the surface 113b of the right head-receiving portion 112b is also in the form of a downward-sloping surface that is circumscribed by a portion of the right side surface 106, a portion of the back surface 108, the inner lateral surface of a left chin support 116b (which is also discussed in more detail below), the right recess neck opening 114b and the ridge 110. In this embodiment, the head-receiving surface portions 113a and 113b terminate at bottom at recessed ear openings (herein also referred to as recessed ear holes) 111a/111b, respectively.

The surface portion 113a includes segments with varying slopes both along the downward direction toward the recessed ear hole opening 111a as well as along a direction perpendicular to the downward direction. For example, as depicted schematically in FIG. 2C, in this embodiment, the slope of the surface portion 113a becomes steeper in a clockwise direction (looking from the top) such that a surface segment proximate the back surface 108 of the top surface has a steeper downward slope than a surface segment proximate the left side surface 105 of the top section, and a surface segment proximate the ridge 110 separating the left and the right portions has a steeper slope than the surface segment proximate the back surface 108 of the top section. Further, as noted above and discussed in more detail below, the slope of the surface portion 113a in a direction orthogonal to the downward direction also exhibits variations at different locations of the surface. In this embodiment, the surface portion 113b of the right head-receiving portion (cavity) is a mirror image of the left surface portion 113a relative to an orthogonal plane bisecting the ridge separating the left and the right portions.

In other words, in this embodiment, the surface of each of the head-receiving portions 112a/112b has a compound slope with variations in both downward direction and a direction orthogonal to the downward direction.

In this embodiment, each of the recessed ear openings 111a/111b extends from the top surface 102 to the bottom surface 104 of the top section. In this embodiment, the recessed ear openings 111a/111b have generally cylindrical shapes, with a generally circular cross-sectional profile, with lateral surfaces 120a/120b, each of which extends from the top surface 102 of the top section to the bottom surface 104 thereof and has a convex curved profile. In other embodiments, the recessed ear openings can have other shapes. For example, in some embodiments, the recessed ear openings can have an elliptical cross-sectional profile. The recessed ear holes in combination with the sloped planes of the head-receiving surface help the user position their head in the top surface.

Figure 4:
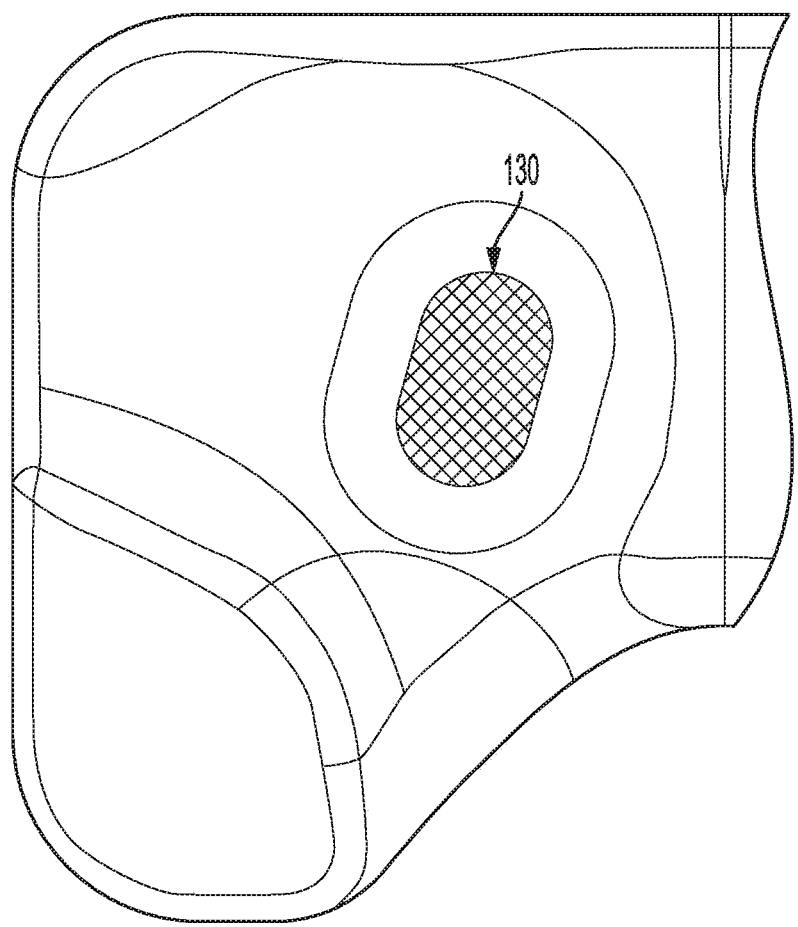
FIG. 4 schematically depicts a ventilation material coupled to a recessed ear hole formed in a head-receiving portion of a pillow according to the present teachings.
Figure 5A:
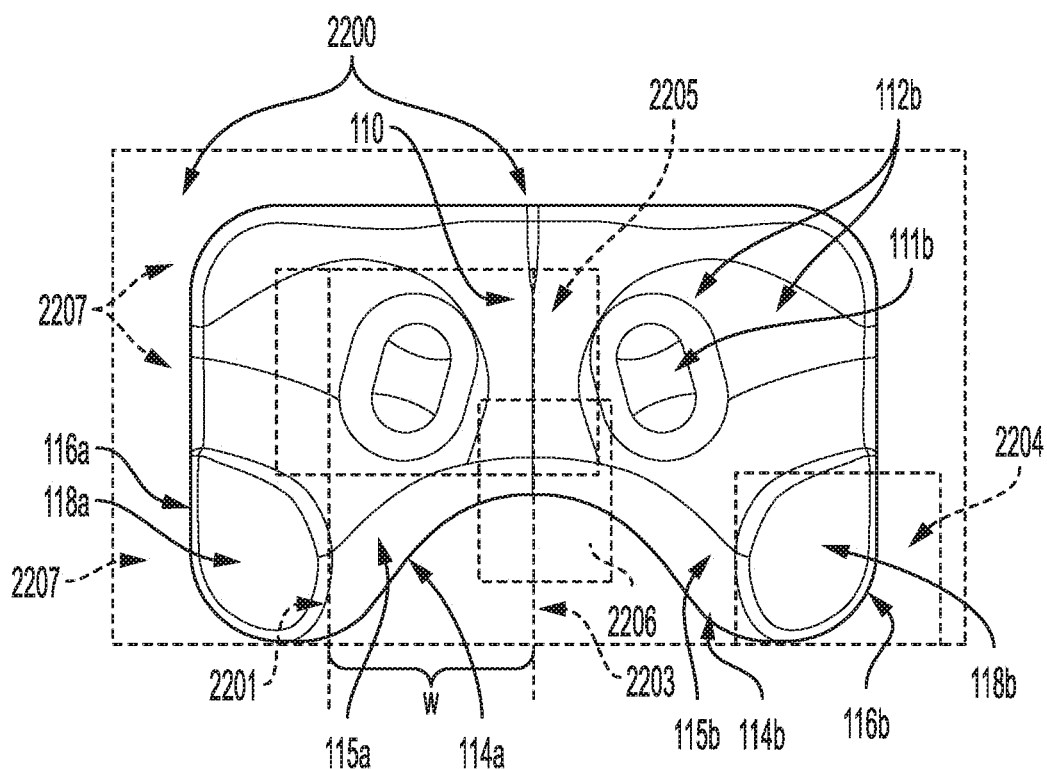
FIGS. 5A, 5B, 5C, and 5D depict various schematic views of a pillow according to an embodiment depicting relationship of various elements of the pillow by utilizing a plurality of putative planes.
Figure 5B:
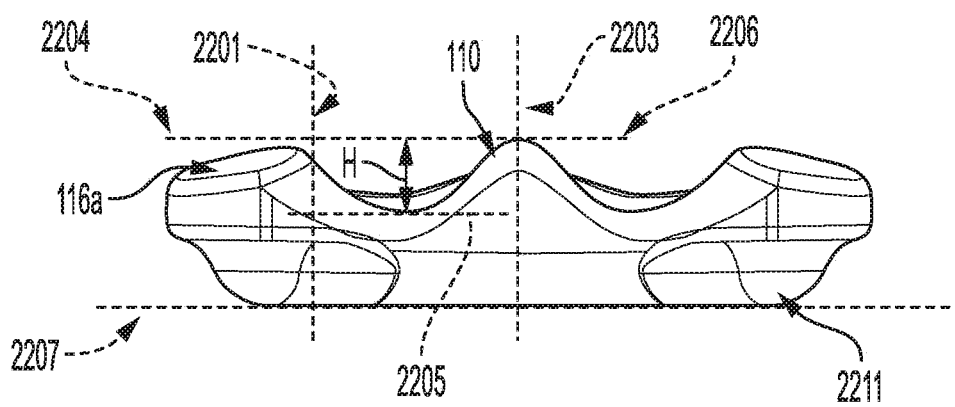
Figure 5C:
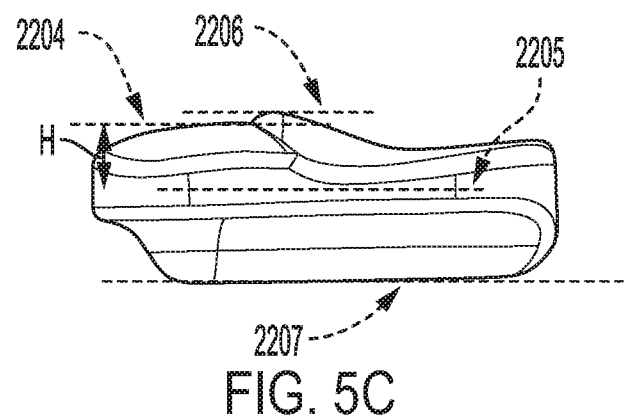
Figure 5D:
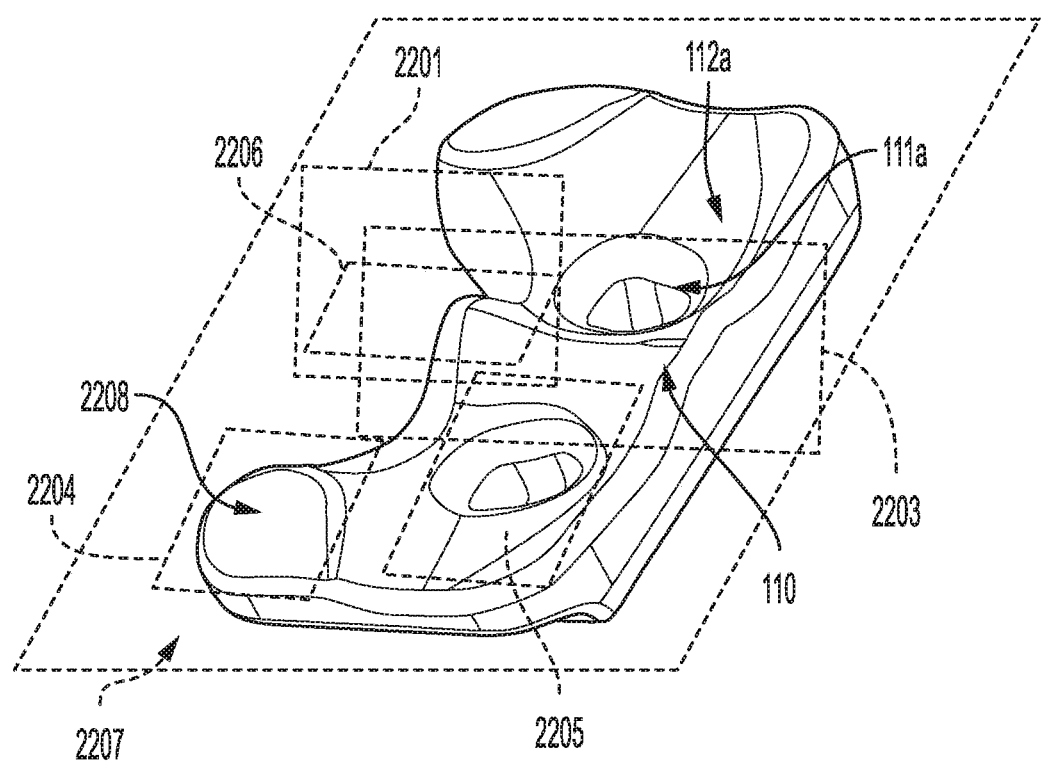

In some embodiments, a maximum cross-sectional dimension, e.g., a diameter, of each recessed ear opening can be, for example, in a range of about 1 inch to about 5 inches so as to comfortably accommodate the variable ear sizes of the users. As depicted in FIG. 4, in some embodiments, at least a portion of the lateral surfaces of the ear openings 111a/111b can be covered with a venting material 130. Some examples of suitable venting materials include, without limitation, silk, cotton, wool, polyester or any combination thereof.

In addition to at least partially receiving a user's ear, the recessed ear openings can also muffle or reduce the noise in the surrounding environment, possible devices used by the user (CPAP machine, noise possibly generated by the pillow, and/or any other noise which is experienced by the user while the user's head is maintained in one of the head-receiving portions.

With reference to FIGS. 2A, 2B, 2C and 2D and as noted above, the top section 101 further includes a left chin support 116a and a right chin support 116b, each of which protrudes above the surfaces 113a/113b of the left and the right head-receiving portions 112a/112b, respectively. In this embodiment, the chin supports 116a/116b include top surface segments 118a/118b and lateral surface segments 117a/117b, respectively, which extend from the top surface segments downwardly to the head-receiving portions (cavities) 112a/112b.

With reference to FIGS. 5A, 5B, 5C and 5D, a maximum height difference (H) between the top surface of each chin support 118a/118b relative to the bottom of the respective head-receiving portions 112a/112b can be, for example, in a range of about 1 inch to about 5 inches, e.g., in a range of about 1 inch to about 4 inches, e.g., in a range of about 2 to about 3 inches. In this embodiment, the maximum height difference between the top of a chin support and the bottom of a respective head-receiving portion can be determined as the distance between a putative plane 2205, which is tangential to the lowest point of a head-receiving portion, which can cover in this embodiment the top of a respective recessed ear opening (e.g., the head-receiving portion 112b covering the top of the recessed ear opening 111b), and a putative parallel plane 2204 that is tangential to the highest point of the top surface of a chin support (e.g., the chin support 116a) and parallel to a flat support surface 2207.

FIGS. 5A, 5B, 5C, and 5D present other putative planes for ease of description of the relationships of various elements of the top section of the pillow 100 relative to one another. For example, the plane 2203 bisects the raised ridge 110. The plane 2201 is parallel to the plane 2203 and is tangential to a portion of the inner lateral surface of the left chin block 116a at the intersection of this lateral inner surface with the left recess neck opening 114a. A putative plane similar to the plane 2201 can be defined with respect to the right chin support 116b. The distance between the planes 2201 and 2203 can be defined as the width (W) of the left shoulder-receiving recess 115a. The width of the right shoulder-receiving recess 115b can be similarly defined. Further, the depth of each shoulder-receiving recess can be defined as a normal distance between the front tip of the ridge 110 (depicted as point P in this illustration) and a surface that is perpendicular to the support surface 2207 and is tangent to the front surface of the chin supports 116a and 116b.

With continued reference to FIGS. 5A, 5B, 5C, and 5D, the height (H) of the highest point of the ridge 110 separating the left and the right portions of the top section of the pillow 100 can be defined as the distance between a plane 2206 tangent to that point and parallel to the flat support surface 2207 and the plane 2205, which is tangent to the lowest point of a head-receiving portion. The heights of other points along the ridge can be found in a similar fashion.

With continued reference to FIGS. 2C, 2D, 3A, and 3B, the lateral surfaces of the left chin support and the right chin support 116a/116b include outer lateral surface segments 119a and 119b and inner lateral segments (herein also referred to as inner laterals surfaces) 117a/117b, where the inner lateral segment of the left chin support extends from the front end of the top section in proximity of the left recess neck opening 114a to the left side of the top surface, and the inner lateral segment of the right chin support extends from the front end of the top section in proximity of the right recess neck opening 114b to the right side of the top section. The inner lateral segments of the chin supports exhibit a varying downward slope from the front end of the top section to a side thereof. For example, the inner lateral surface 117a of the left chin support exhibits a downward slope that becomes progressively steeper as the inner lateral surface 117a extends from the front end of the top section to its left side. The inner lateral segment 117b of the right chin support is a mirror image of the inner lateral segment 117a of the left chin support, and exhibits a progressively steeper downward slope as it extends from the front end of the top section to the right side thereof. In this embodiment, the compound slope of the inner lateral surface of each chin support is configured to substantially conform with the contour of the neck of individuals within $50^{th}$ percentile of the population.

As noted above, the chin supports 116a/116b further include outer lateral surface segments 119a and 119b, respectively. The outer lateral surface segment 119a of the left chin support 116a is in the form of a curved surface that extends from the left end of the left recess neck opening 114a to a lower end of the left side of the left head-receiving portion 112a. Further, the outer lateral surface segment 119b of the right chin support, which is a mirror image of the outer lateral surface 119a of the left chin support, is also in the form of a curved surface that extends from the right end of the right recess neck opening 114b to the lower end of the right side of the right head-receiving portion 112b. In this embodiment, the outer lateral surfaces 119a/119b of the left and the right chin supports 116a/116b extend orthogonally from the top surface of the chin support to the bottom surface of the top section.

Figure 3A:
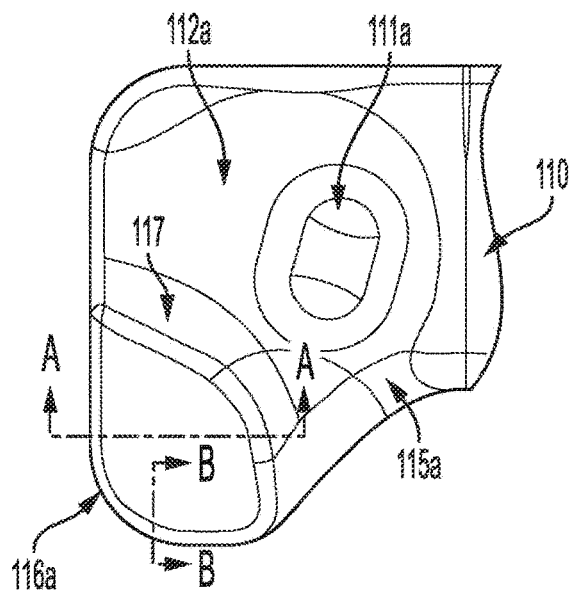
FIG. 3A depicts a partial view of the top section of the pillow.
Figure 3B:
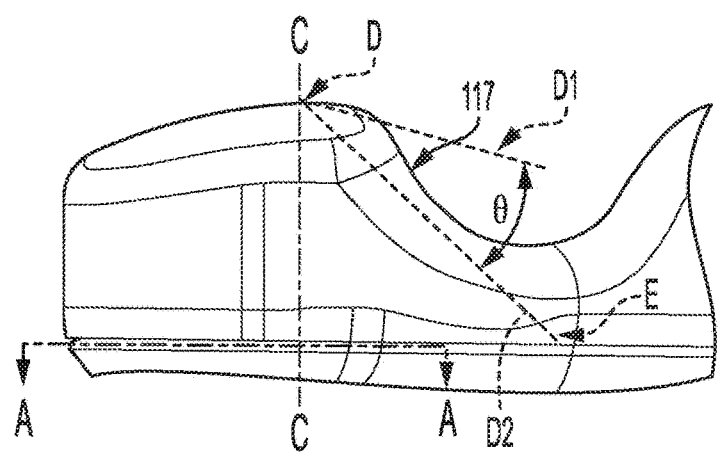
FIGS. 3B-3C schematically depict that the lateral surface of the chin support according to an embodiment has a compound slope.
Figure 3C:
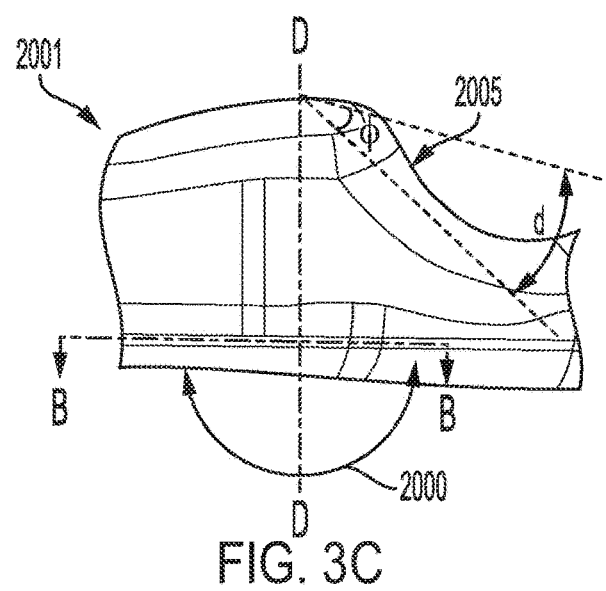

As noted above, the inner lateral surface of each of the left and the right chin support 116a/116b has a compound slope that can vary across the inner lateral surface. By way of illustration, FIG. 3A is a schematic plan view of the left portion of the top section of the pillow 100, which depicts the head-receiving cavity 112a, the chin support 116a and the recessed ear hole 111a. In this embodiment, an inner lateral surface 117 of the chin support 116a exhibits a compound slope. For example, FIG. 3B provides a cross-sectional view of the chin support 116a along the A-A direction. This cross-sectional view depicts the downward slope of the chin support at a point (D) at the top of the chin support, which can be characterized by an angle (θ) between a putative line segment D1 tangent to the point (D) and a putative line segment D2, which extends from the point D to a point E, which is at the boundary of the inner lateral surface 117 of the chin support and the surface of the head-receiving cavity. As this figure shows, the slopes at other points along the inner lateral surface defined similarly as that defined for point (D) can vary from one surface point to another. Further, FIG. 3C, which is a cross-sectional view of the inner lateral surface of the chin support along the B-B direction, shows that the slope of the inner lateral surface of the the chin support varies also along a direction perpendicular to the downward direction. More specifically, FIG. 3C shows that such a slope at the point D can be characterized by an angle φ, which is similarly defined as the angle θ above. Similar to the downward slope, such a slope of the lateral surface of the chin support can also vary from one point to another. Further, at each point of the lateral surface, the angles θ and φ can be the same or different.

The compound slope of the inner lateral surface of the chin support can help place a user in a sniff position, thus aligning the user's airways for improved airway management. In particular, in many embodiments, the compound slope of the inner lateral surface of the chin support can be the mirror image of the compound slope of the neck and platysmal surface of the side of the user's neck allowing the inner surface to comfortably receive the lateral platysmal surface.

In this embodiment, the top of each chin support is slanted toward a side of the top section of the pillow (i.e., to the left side for the left chin support and to the right for the right chin support). In other embodiments, the top surface of at least one, or both chin supports, can be flat.

As noted above and shown in FIG. 2D, the top section 102 includes the ridge or raised surface 110, which separates the left and the right portions of the top section 101 and assists in aligning a user's head and prevents and/or inhibits the user from inadvertently assuming the supine position. In some embodiments, the ridge 110 rises above the surface of the head-receiving portions 112a/112b such that it has a maximum height, as defined above and in connection with FIGS. 5A-5D, in a range of about 1.5 inches to about 5 inches, e.g., in a range of about 2 inches to about 4.5 inches, or in a range of about 3 inches to about 4 inches, above the lowest portion of that surface.

With reference to FIG. 2B, in this embodiment, the ridge 110 separating the left and the right portions of the top section of the pillow has a non-uniform height. In particular, the height of the ridge decreases as the ridge extends from the point (P) proximate the front surface of the top section to point (Q) proximate the back surface of the top section. In some such embodiments, the ridge 110 exhibits a height non-uniformity in a range of about 10% to about 300%. In other words, the fractional height difference between the highest and the lowest points of the ridge, as measured relative to the putative plane covering a recess ear opening, can be in a range of about 10% to about 300%.

The non-uniform height of the ridge can help inhibit the user from inadvertently assuming a supine position while ensuring that the user will not experience claustrophobia due to excessive height of the ridge, particularly in the distal end of the ridge, which may block the user's vision.

Further, in some embodiments, the ridge extends at its proximal end from the right end of the left recess neck opening to the left end of the right recess neck opening. Referring to FIG. 2B, the width (WR) of the ridge 110 at its proximal end can be, for example, in a range of about 3 inches to about 6 inches, e.g., in a range of about 4 inches to about 5 inches. The left and the right side surfaces of the ridge 110 slope downwardly to the left and right head-receiving portions 116a and 116b.

Figure 2D:
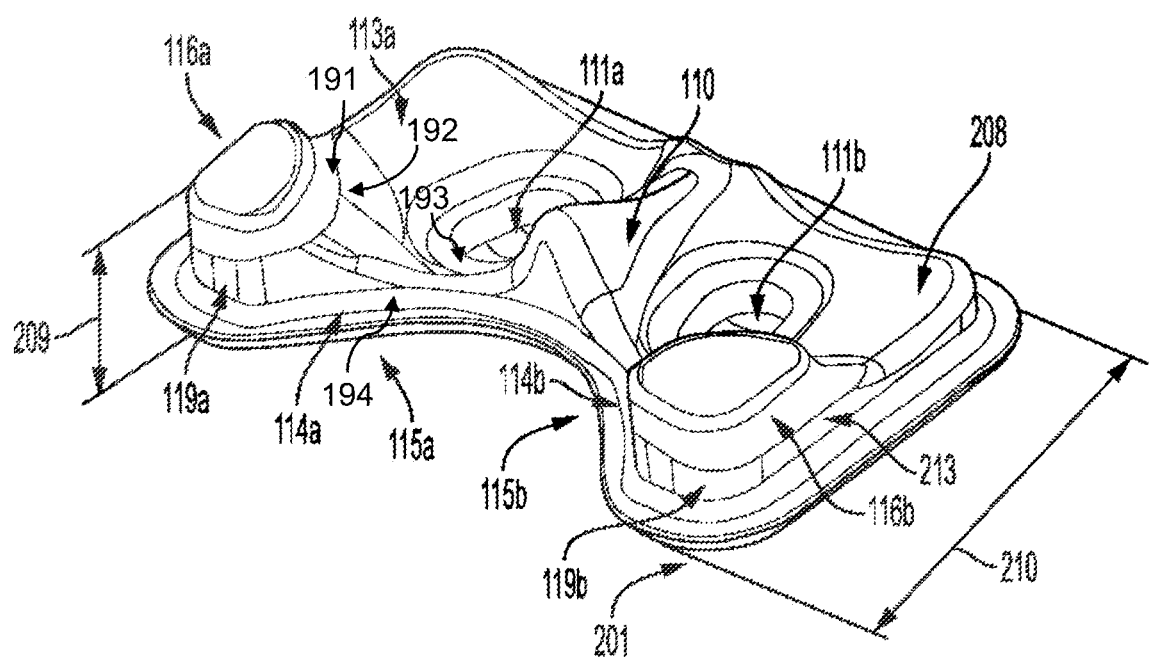

With reference to FIG. 2D, the left and right recess neck openings 114a/114b are in the form of curved ridges that extend from the left and right chin supports, respectively, to the ridge 110. In this embodiment, each of the recess neck receiving ridges exhibits a varying radius of curvature from its one end to the other. For example, the radius of curvature of the left recess neck opening 114a can increase as the recess neck opening extends from the chin support 116a to the ridge 110, and the radius of curvature of the right recess neck opening 114b can decrease as the recess neck opening extends from the ridge 110 to the right chin support 116b. In some embodiments, the recess neck openings can have a compound curvature, for example, in a range of about 1 inch to about 4 inches in order to able to comfortably receive differing user neck sizes. In other embodiments, one or both of the recess neck openings can be configured to have a single radius of curvature.

The dimensions of the shoulder-receiving recesses are generally chosen so as to inhibit the movement of a user from a lateral decubitus position to a supine position. For example, in this embodiment, the ratio of the width to the depth of each of the shoulder-receiving recesses 115a/115b can be, for example, in a range of about 1.5:1 to about 6:1, e.g., in a range of about 4:1 to about 6:1. By way of example, the width of each of the shoulder-receiving recesses can be in a range of about 6 inches to about 18 inches, and the depth of each of the shoulder-receiving recesses can be in a range of about 1 inch to about 12 inches.

Figure 2E:
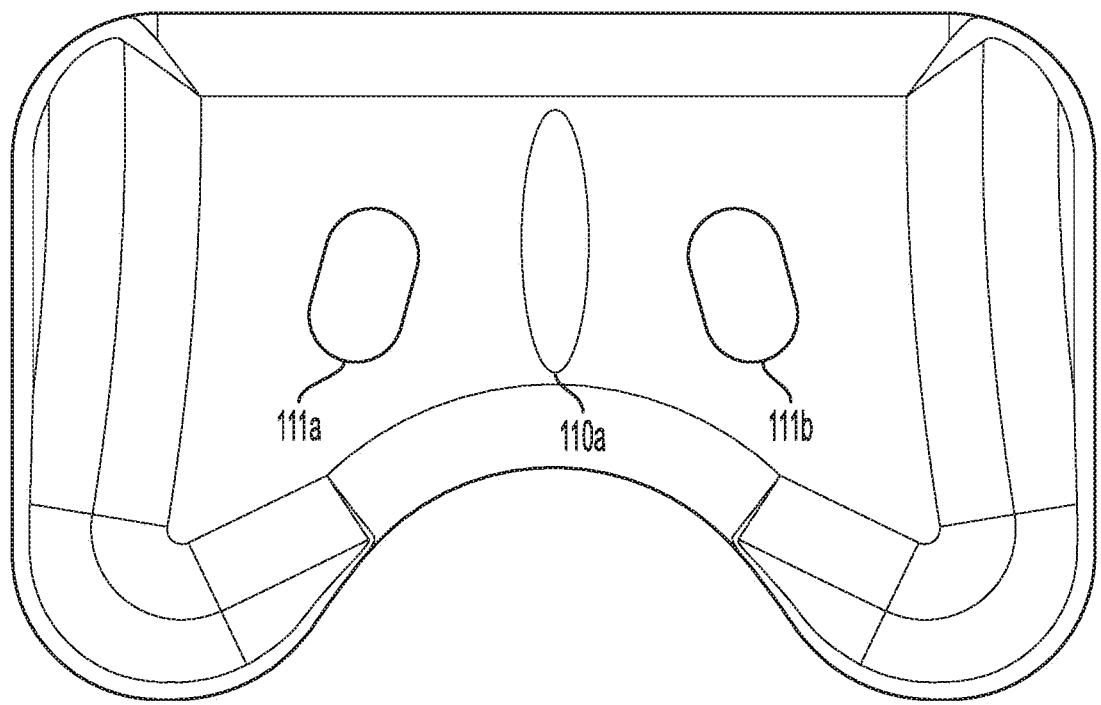
FIG. 2E schematically depicts the bottom surface of the top section of the pillow depicted in FIGS. 2A and 2B.

FIG. 2E schematically depicts the bottom surface 104 of the top section, which can matingly engage with the top surface of the bottom section, depicting the bottom of each recessed ear hole 111a/111b as well as a cavity 110a associated with the ridge 110, which separates the right and left portions of the top section.

Figure 6A:
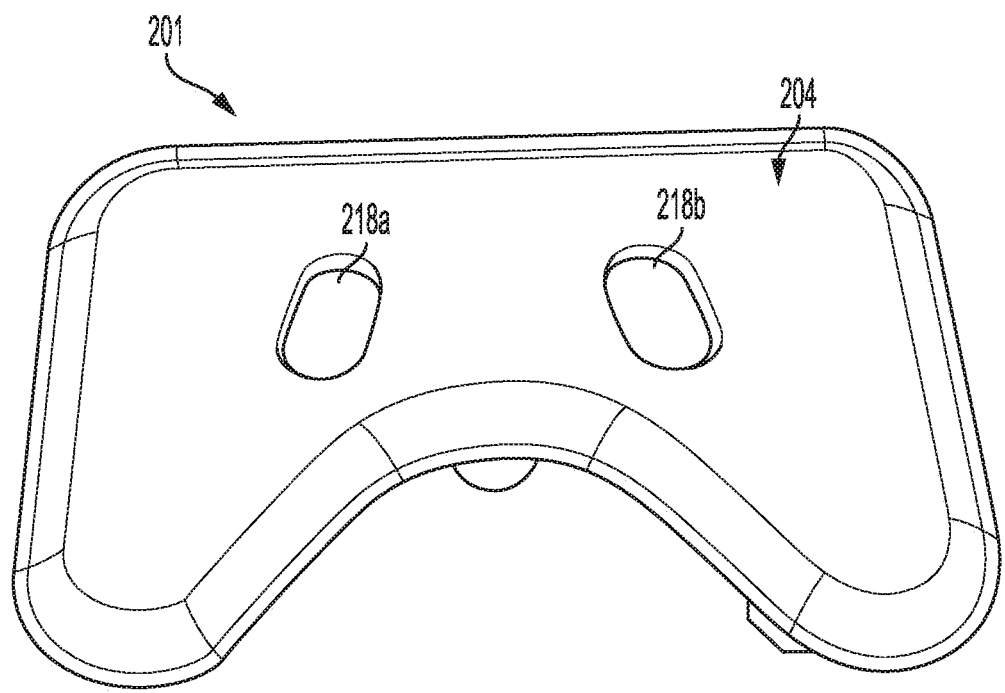
FIG. 6A schematically depicts the top surface of the bottom section of the pillow depicted in FIG. 2A.
Figure 6B:
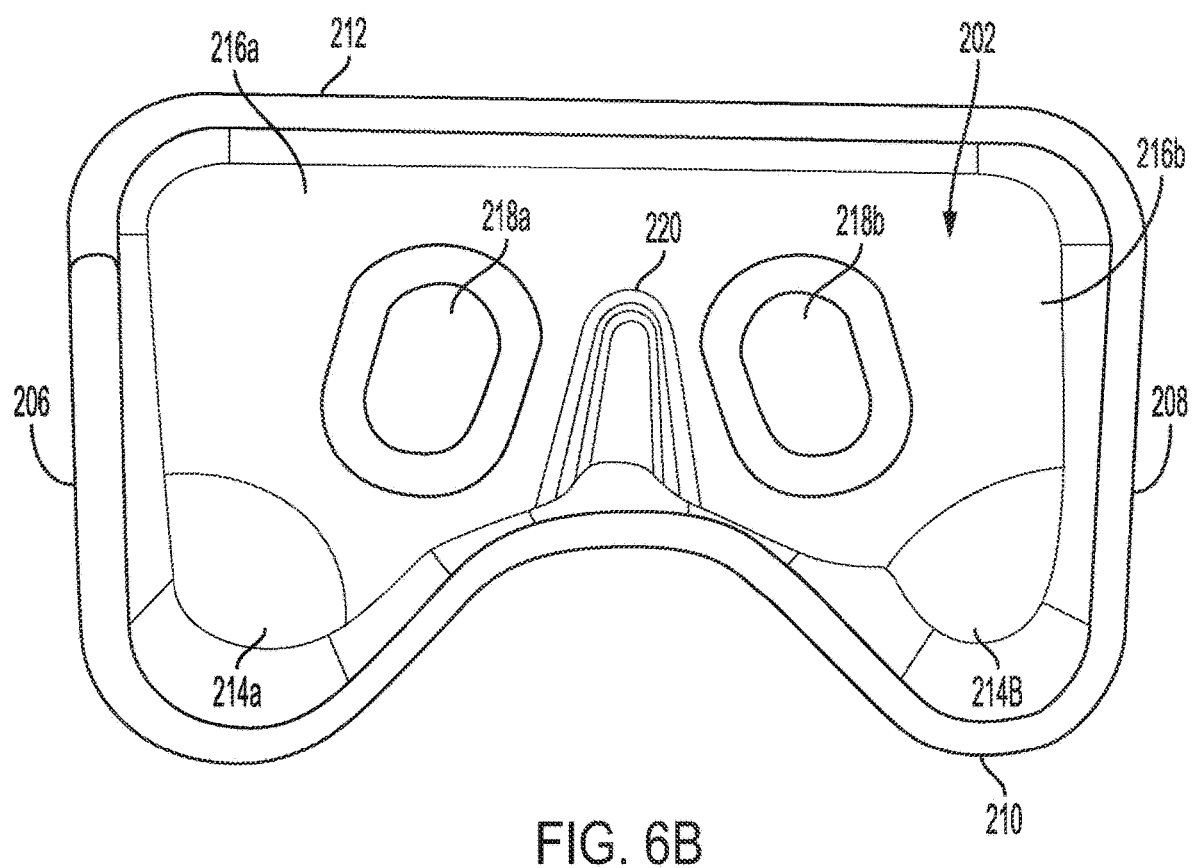
FIG. 6B schematically depicts the bottom surface of the bottom section of the pillow depicted in FIG. 2A.

More specifically, with reference to FIGS. 6A and 6B, the bottom section 201 extends from a top surface 202 to a bottom surface 204. The bottom section 201 further includes a left side surface 206, a right side surface 208, a front surface 210 and a back surface 212. In this embodiment, the top surface 202 of the bottom section is shaped so as to matingly engage with the bottom surface of the top section.

In this embodiment, the bottom surface of the bottom section is substantially flat for positioning on a supporting surface, e.g., a mattress.

Figure 6C:
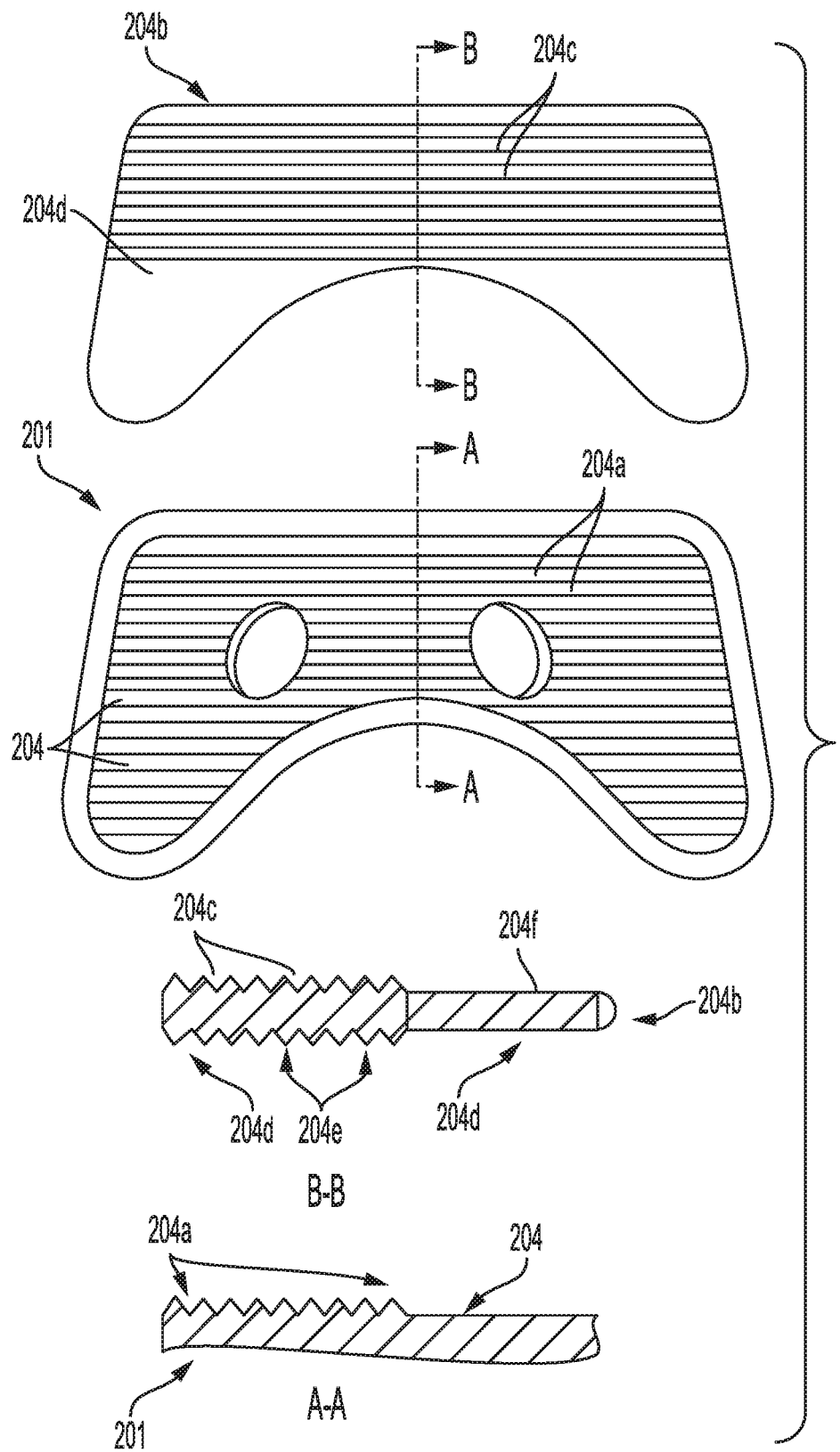
FIG. 6C schematically depicts the bottom surface of the bottom section of the pillow depicted in FIG. 2A with mating surfaces and height adjustment inserts with mating surfaces.

In some embodiments, one or more height-adjusting inserts (herein also referred to as wedges) can be removably and replaceably coupled to the pillow 100 to adjust its height, e.g., based on the needs of individual users. By way of example, FIG. 6C illustrates one embodiment of the pillow 201, which can be removably and replaceably coupled to one or more height-adjusting inserts. More specifically, a height-adjustment insert 204b can be removably and replaceably coupled to the bottom section 201. In this embodiment, the bottom surface 204 of the bottom section 201 includes a plurality of sawtooth features 204c disposed on a top surface 204f of the height-adjusting element. The engagement of the complementary sawtooth surfaces provided on the bottom surface of the bottom section 201 and the top surface of the insert 204b can provide mating surfaces that allow for a snug fit between the pillow and the insert. Such mating surfaces can be cut or otherwise formed on any suitable surface of the pillow and the insert. Although in this embodiment, the mating surfaces are shown as sawtooth interlocking surfaces, in other embodiments the mating surfaces can have other forms so long as they can fit snuggly together, e.g., to stabilize the coupling between the pillow and the insert. The mating surfaces can be removably and replaceably engaged with one another, thus allowing adjustment of the height of the apparatus by adding and subtracting one or more inserts. The thickness of the insert 204b can be, for example, in a range of about 0.25 inches to about 3 inches, though other thicknesses can also be employed. Although in this embodiment the height-adjusting insert has a length and a width that are substantially identical to the respective length and width of the bottom section 201, in other embodiments, the length and/or the width of the insert can be less than the respective length and/or width of the bottom section of the pillow, e.g., by about 70%.

With continued reference to FIG. 6C, in this embodiment, the bottom surface 204d of the insert 204b also includes a plurality of sawtooth surfaces that can matingly engage with a plurality of complementary sawtooth surfaces provided on a top surface of another insert (not shown in this figure). In this manner, more than one insert can be coupled to the bottom section of the pillow to allow more flexibility for adjusting the pillow's height.

The bottom section 201 of the pillow can be removably and replaceably engaged with the top section 101 thereof. For example, as noted above, the top surface of the bottom section can be matingly engaged with the bottom surface of the top section. For example, as shown in FIG. 6, the top surface 202 of the bottom section 201 includes left and right raised ridges 214a/214b, each of which is shaped and dimensioned to fit snuggly within a pocket associated with a respective one of the chin supports 116a/116b of the top surface 102 of the top section 101. The top surface of the bottom section further includes a ridge 220 that is shaped and dimensioned to fit snugly within a cavity associated with the ridge 110 in the top section, which separates the left and right portions of the top section. Further, the top surface 202 of the bottom section 201 includes downward-sloping portions 216a/216b that extend downwardly to recessed ear holes 218a/218b. The downward-sloping portions 216a/216b can fit matingly to portions of the back surface of the top section forming the back surfaces of the head-receiving portions 112a/112b formed in the top section.

The recessed ear holes 218a/218b formed in the bottom section of the pillow extend from the top surface of the bottom section to a bottom surface thereof. Similar to the recessed ear holes formed in the top section of the pillow, in this embodiment, the recessed ear holes 218a and 218b are substantially cylindrical with a convex-shaped lateral surface, though in other embodiments other cross-sectional profiles and shapes can be employed. The recessed ear holes 218a and 218b are positioned in the bottom section of the pillow such that upon coupling the bottom section with the top section of the pillow, each of the recessed ear holes in the bottom section is substantially aligned with a respective recessed ear hole in the top section. Thus, in this embodiment, when the top and the bottom sections of the pillow are engaged, recessed ear holes extend from the top surface of the top section of the pillow to the bottom surface of the bottom section of the pillow.

With reference to FIG. 4, in some embodiments, the lateral surfaces of the recessed ear holes can be covered at least partially with a venting material 130. By way of example, the venting material 130 can be in the form of a mesh. Some examples of suitable venting materials include, without limitation, silk, cotton, wool, polyester or any combination thereof.

The top and the bottom sections of the pillow can be formed of a variety of different materials. The material from which the top and the bottom sections of the pillow are fabricated is preferably hypoallergenic. Some examples of suitable materials can include, without limitation, polyurethane, a memory foam, an open cell foam, polyethylene and ethylene vinyl acetate (EVA). For example, the top and the bottom sections of the pillow can be formed of viscous elastic foam material. The foam material can be convoluted or otherwise configured to evenly distribute pressure caused by pressure points of the user's head and neck. By way of example, the convolutions of the foam material may exhibit a maximum depth of less than about 2 centimeters.

In some embodiments, the density of the material used to fabricate the pillow can be, for example, in a range of about 1.25 to about 1.35 lb/ft$^3$. In some embodiments, different portions of the pillow can be fabricated using foam materials with different densities.

In some embodiments, the top section and the bottom section of the pillow can be fabricated using foam materials of different densities. For example, in some embodiments, the bottom section of the pillow can have a hardness greater than that of the top section of the pillow. By way of example, the difference in the hardness of the top and the bottom sections of the pillow can be characterized by an IDL equal to or greater than about 0.5, e.g., in a range of about 0.5 to about 2.

Figure 7:
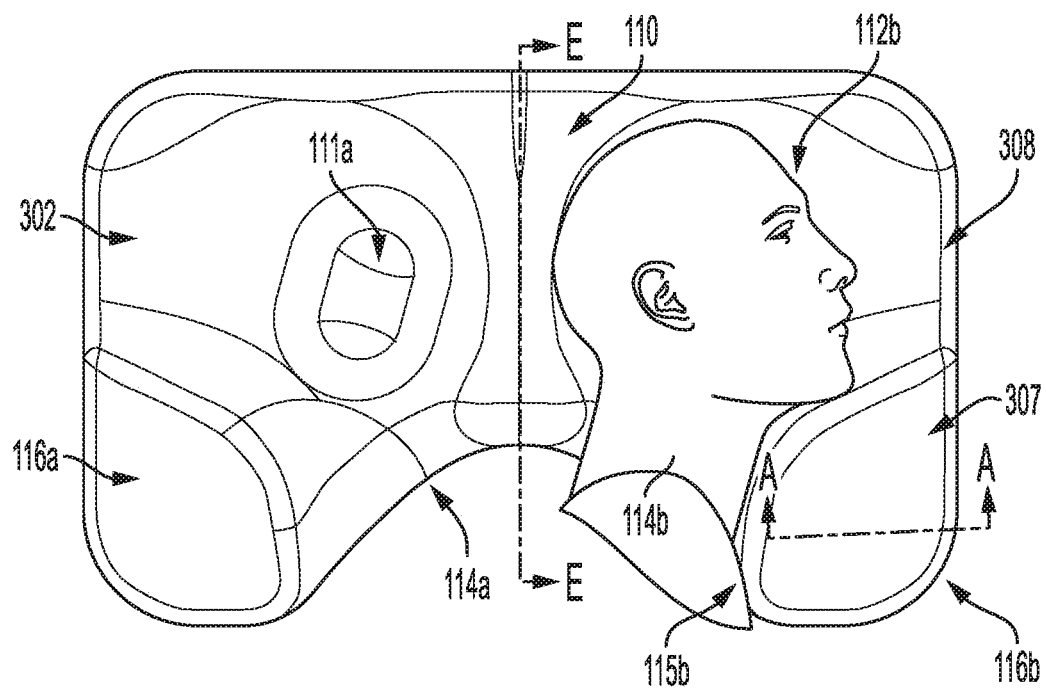
FIG. 7 schematically depicts an individual using a pillow according to an embodiment in the left lateral decubitus position.

The pillow 100 can be used by a user in left lateral decubitus position and in the right lateral decubitus position. By way of example, FIG. 7 schematically depicts a user using the pillow 100 lying on his left side in a left lateral decubitus position with the user's head received and supported in the right head-receiving portion 112b and the shoulder and the neck of the user supported by the right shoulder-receiving recess 115b and the right recess neck opening 114b allowing comfortable assumption of the lateral decubitus position. A portion of the lateral surface of the right chin support 116b is in contact with a portion of the user's jaw to elevate the user's chin so as to cause extension of the user's upper cervical spine and a flexion of the user's lower cervical spine, thereby facilitating the placement of the user in a sniff position.

Figure 8:
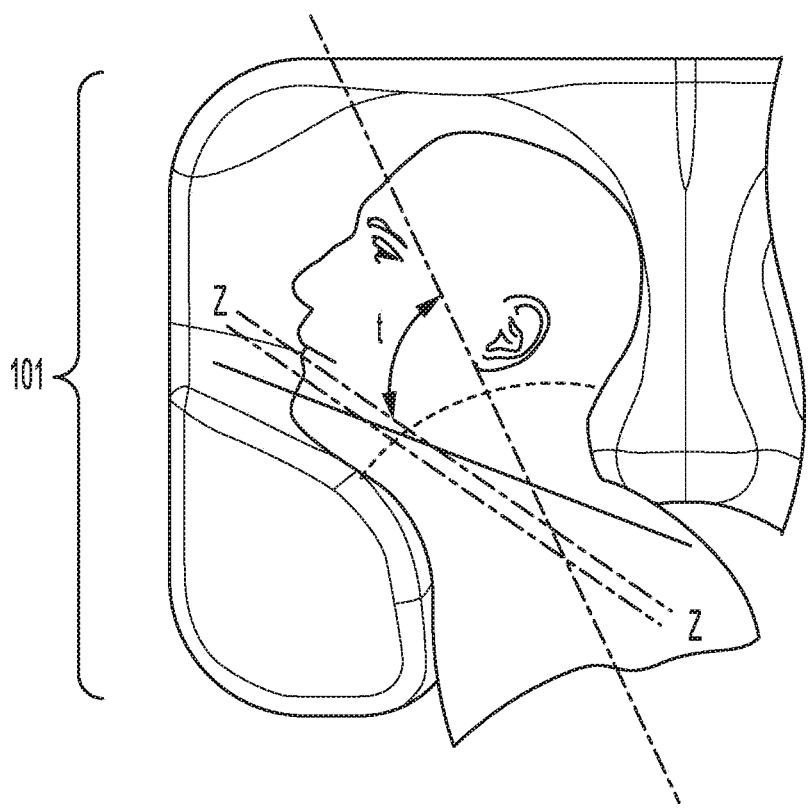
FIG. 8 schematically depicts an individual using a pillow according to an embodiment in the right lateral decubitus position in a sniff position, indicating better alignment of the airway passages relative to a neutral position.

As discussed above with reference to FIG. 8, in a sniff position, the laryngeal, tracheal and oropharyngeal airway axes of the head are better aligned than in a neutral position of the head, thus enhancing airway management. For example, in many embodiments of a pillow according to the present teachings, the pillow allows aligning the tracheal and laryngeal axes such that an angle between these two axes is less than about 10 degrees, and preferably less than about 5 degrees. Further, the pillow allows positioning of the user in a lateral decubitus position such that an angle between the oropharyngeal and laryngeal axes is less than 90 degrees, e.g., in a range of about 5 degrees to about 30 degrees.

In some embodiments, the pillow allows a user to assume the lateral decubitus position with the user's Occipito-Atlanto-Axial joint at an angle t between about 5 degrees and 60 degrees.

As discussed above, the left and the right chin supports facilitate the placement of the subject in a sniff position by elevating the subject's head. In many embodiments, each of the head-receiving portions, and the respective recess neck opening as well as the chin support are configured, dimensioned and positioned relative to one another such that when the user is in a lateral decubitus position with the user's head received by the head-receiving portion, the user's upper cervical spine experiences an extension in a range of about 5 to about 20 degrees and the user's lower cervical spine experiences a flexion in a range of about 5 to about 15 degrees.

Further, in some embodiments, the configuration and relative positioning of the head-receiving portion and the recess neck opening are such that the user's cervical spine can be maintained into substantially parallel alignment with the surface upon which the user is lying.

Figure 9A:
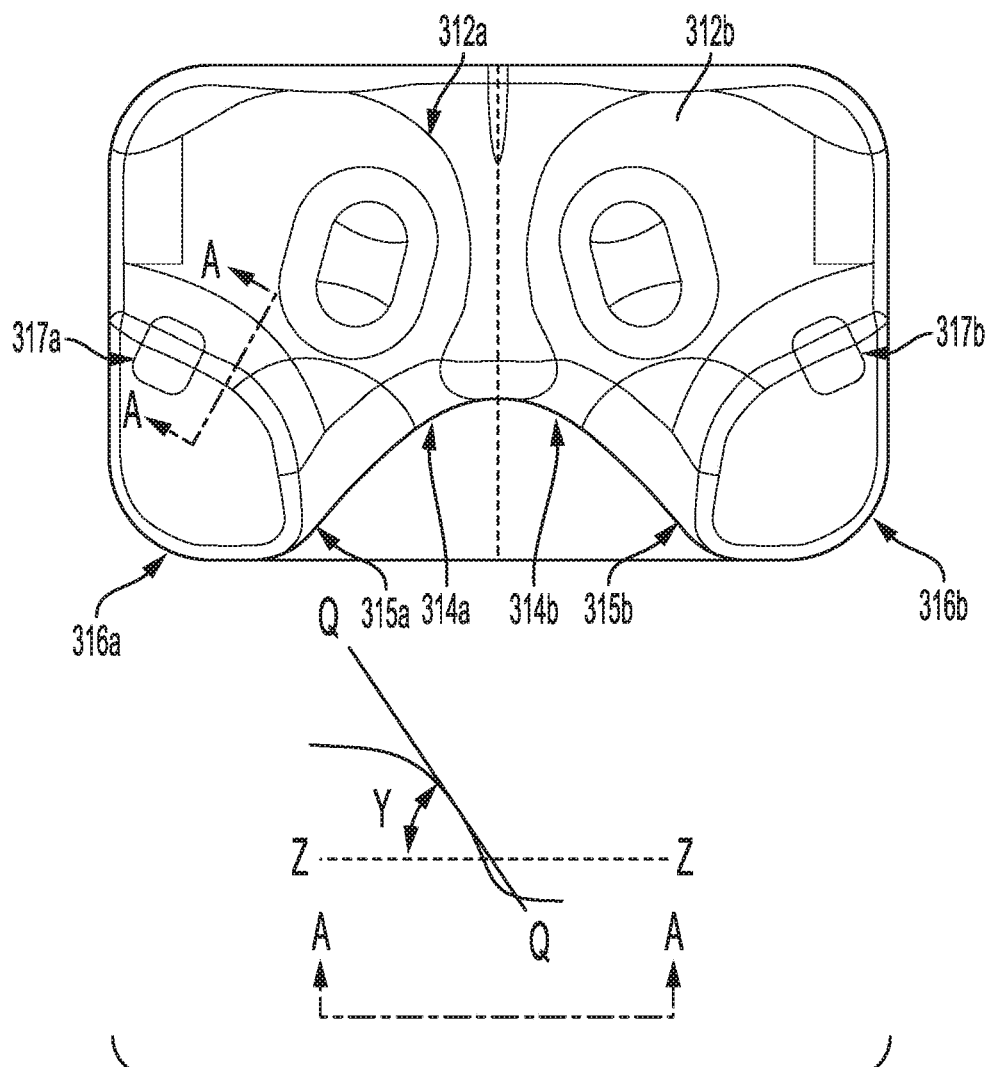
FIG. 9A schematically depicts the top section of a pillow according to an embodiment in which a left and a right adjustable chin positioner are coupled to the left and right chin supports of the pillow.

With reference to FIG. 9A, in some embodiments, a pillow 300 can include a left chin support 316a and a right chin support 316b, where the left chin support 316a includes an adjustable chin positioner 317a and the right chin support 316b includes an adjustable chin positioner 317b. Similar to the previous embodiment, the pillow 300 includes a top section 301, a bottom section (not shown in this figure), where the top section includes left and right portions having head-receiving portions 312a/312b, recess neck openings 314a/314b, and shoulder-receiving portions 315a/315b. Similar to the previous embodiment, in this embodiment, each of the chin support 312a/312b is in the form of a protrusion rising above a top surface 302 of the top section of the pillow. However, in this embodiment, each of the chin supports includes a movable/adjustable chin positioner that can be moved so as to accommodate different sizes and/or contours of the jaws, the chins and the necks of different users.

An adjustable chin positioner according to the present teachings can be implemented in a variety of different ways. For example, an adjustable chin positioner can be movably mounted onto a surface of a chin support using hook & loop fasteners, posts and corresponding holes, or other non-permanent means of attachment, which would allow moving the adjustable chin positioner to configure the pillow for a particular user.

Figure 9B:
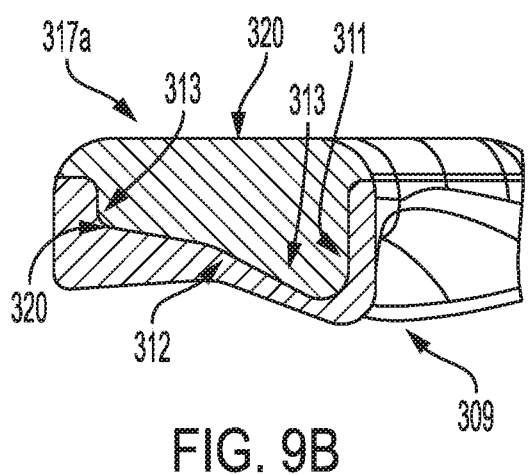
FIGS. 9B and 9C schematically depict an example of an implementation of an adjustable chin positioner in which a chin support block is movably engaged within a groove provided on a surface of the chin support.
Figure 9C:
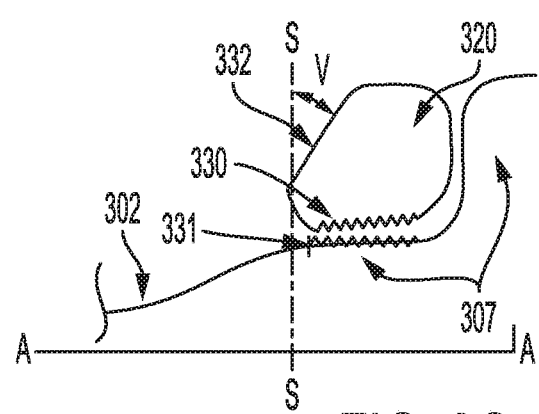

By way of another example, with reference to FIG. 9B, the adjustable chin positioner 317a can include a chin block 320 that is movably engaged within a groove 313 provided on a top surface of the chin support 316a. More specifically, as shown in FIG. 9C, in this embodiment, the bottom surface 330 of the chin block 320 includes a sawtooth surface and the groove includes a mating sawtooth surface 331 for releasably engaging the sawtooth surface of the adjustable chin positioner such that the adjustable chin positioner can be moved back and forth along the groove. In this embodiment, the groove has a curved profile and extends from a front side of the top surface to a lateral side thereof. Further, in this embodiment, the chin block 320 includes a slanted lateral surface 332, which can make an angle V, e.g., in a range of about 20 degrees to about 90 degrees, with a vertical axis S-S. The lateral surfaces of the chin block 320 are in contact with the lateral surfaces 313 and 311 of the groove. While in some embodiments, the slanted lateral surface 332 can be flat, in other embodiments it can be sloped. For example, it can have a compound slope.

As noted above, the adjustable chin positioner can be implemented in a variety of different ways. By way of another example, FIGS. 10A, 10B, and 10C schematically depict the left portion of a pillow 2400 that includes a head-receiving portion 2403 having a recessed ear hole 2402 at the bottom thereof, and a chin support 2401 having an inner lateral surface 2406, which incorporates an adjustable chin positioner. More specifically, the inner lateral surface 2406 includes an opening 2405a into which a chin support block 2405 can be movably coupled. In other words, the movable chin support block 2405 can be moved inward and outward relative to the opening so as to accommodate different sizes and contours of the jaws, the chins and the necks of different users.

With reference to FIG. 10B, in this embodiment, the chin support block 2405 of the adjustable chin positioner includes a collar 2406 from which a stem 2407 extends, where the stem can be movably positioned within the opening 2405a. In this embodiment, a portion of the lateral surface of the chin support surrounding the opening 2405a is recessed relative to the opening so as to allow swiveling the chin support block 2405 around the opening. In this manner, the chin support block 2405 is provided with two degrees of freedom, i.e., in-and-out movement and rotation relative to the opening, which allow adjusting the chin support surface to a user's need. In this embodiment the outer surface 2406a of the collar 2406 can have a curved profile such that when the support block 2405 is fully engaged within the opening 2405a, the outer surface of the collar can be substantially flush, at least for one orientation of the collar, with the remainder of the lateral surface of the chin support. In some such embodiments, the outer surface 2406a of the chin support block 2405 can exhibit a compound slope that can complement the compound slope of the inner lateral surface of the chin support.

Figure 11A:
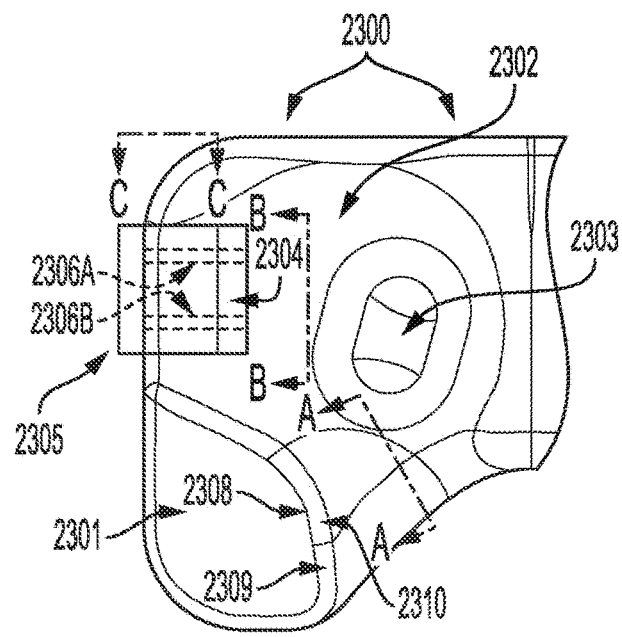
FIG. 11A is a partial schematic view of a pillow according to an embodiment, which includes a removable and replaceable block.
Figure 11B:
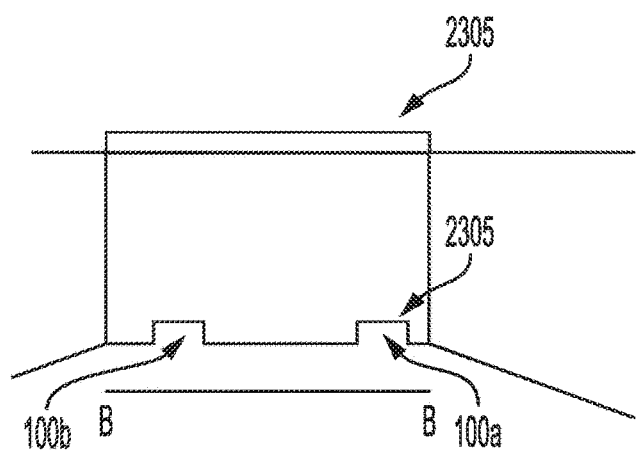
FIGS. 11B and 11C schematically depict the removable block shown in FIG. 11A includes two grooves for movably coupling to two rails provided on the top section of the pillow.
Figure 11C:
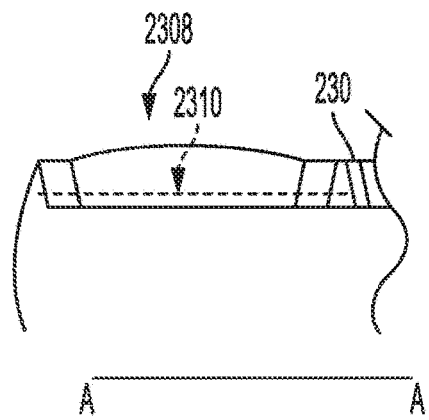

In some embodiments, the top section of a pillow according to an embodiment of the present teachings can include a left and a right removable and replaceable portion (block) that can be removed to allow access to the user's nose and mouth when the user's head is received in the left and the right head-receiving portions, respectively. By way of illustration, FIGS. 11A, 11B, and 11C schematically depict the left portion of such an embodiment 2300, which includes a head-receiving portion 2302 having a recessed ear hole 2303 at the bottom thereof. A chin support 2301 rises above the head-receiving portion. The depicted pillow further includes a removable and replaceable block 2305, which includes two grooves 100a/100b for engaging with two rails 2306a and 2306b provided on the top surface of the pillow. Such engagement of the grooves in the removable block with the respective rails allows replaceably removing the block from the pillow so as to provide access, e.g., to a user's mouth and nose. By way of example, such access may be utilized to connect the user to a monitoring device and/or a therapeutic device (e.g., CPAP) as the user's head is received and supported in the head-receiving portion in a lateral decubitus position.

Figure 12:
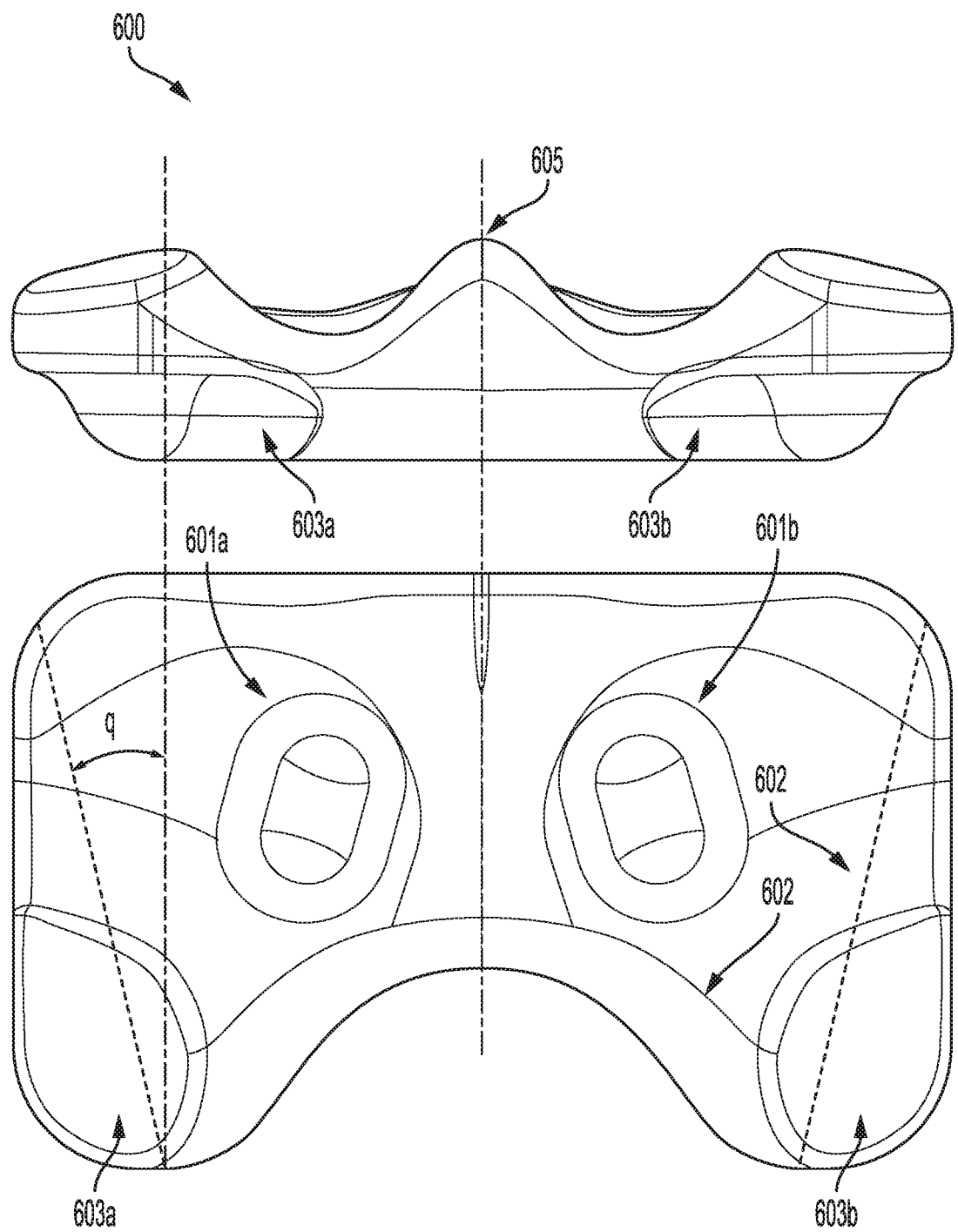
FIG. 12 schematically depicts a pillow according to an embodiment of the present teachings that includes a left and a right arm cut-out.

With reference to FIG. 12, in some embodiments, the left and the right side surfaces of the top section of a pillow 600 according to an embodiment of the present teachings includes left and right cut-outs 603a and 603b, respectively, which can accommodate at least a portion of a user's left and right arms, as the user's head is received in the respective left and right head-receiving portions 601a/601b in a left or a right lateral decubitus position. The arm cut-outs 603a/603b provide additional comfort as the user uses the pillow in a left or a right lateral decubitus position. More specifically, FIG. 12 shows a plan view of the top surface of the pillow with spine or raised ridge 605 between head-receiving portions 601a/601b. In this embodiment, the arm cut outs 603a/603b are positioned at an angle q relative to axis x-x with angle z being in a range between 0° and 45°.

Figure 13A:
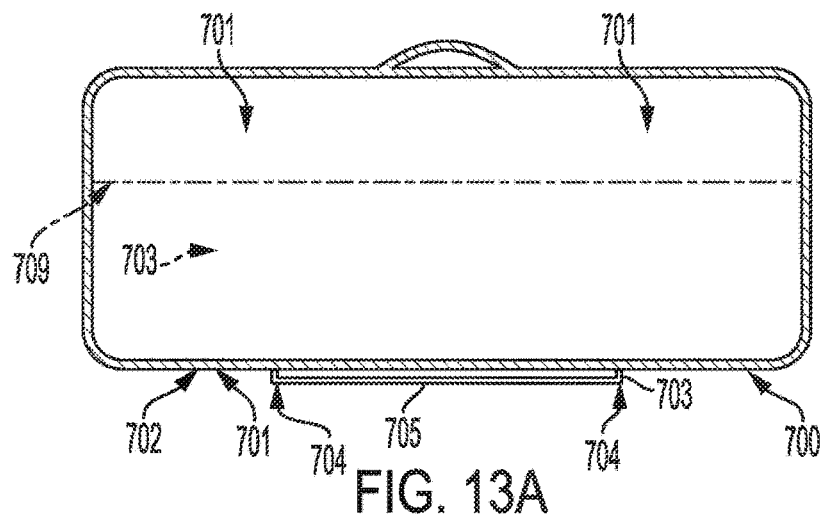
FIGS. 13A, 13B, and 13C schematically depict a pillow according to an embodiment enclosed within a pillow cover.
Figure 13B:
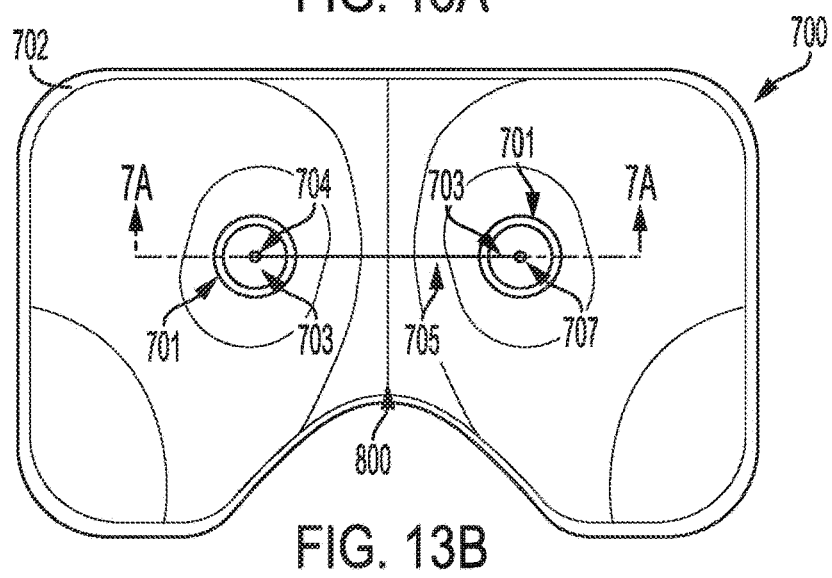
Figure 13C:
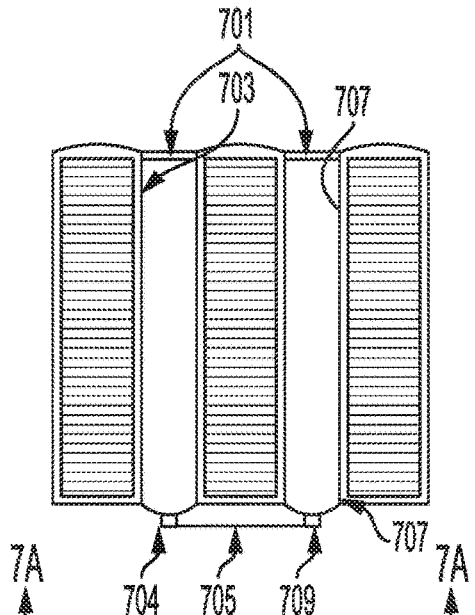

In some embodiments, in addition to the top section, the bottom section can also include respective arm cut-outs, e.g., similar to those shown for the top section. In some embodiments, such arm cut-outs provided in the bottom section can be positioned substantially below the respective arm cut-outs on the top section when the top and bottom sections of the pillow are engaged with one another. In some embodiments, a pillow according to the present teachings can be at least partially covered by a cover. By way of example, with reference to FIGS. 13A, 13B, and 13C, a pillow 700 includes a top and bottom section (in this figure only the top section is visible). Further, similar to previous embodiments the top section includes a left and a right portion separated by ridge 800 where each of the left and right portions includes a head receiving portion, a chin support, and a recessed ear opening. For example, FIGS. 13A, 13B, and 13C show how an embodiment of the cover can fit around a pillow. A zipper 709 in cover 702 allows pillow 700 to be inserted into cover 702 and be encapsulated therein, where cover 702 fits snugly over pillow 700. Ear hole extension 703 can be fitted into, and passed down through, recessed ear hole cover 701 in pillow 700. The end of each hole extension 703 distal to the top surface of pillow 700 in this embodiment has strap 705 attached to it by mechanical means (including sewing or glue). One end of strap 705 has a mechanical means of attachment (a button, hook, or hook and loop fabric) 704. The end of ear hole extension 707 distal to top surface of pillow 700 in this embodiment has a means of receiving an attachment built into it (such as a button hole, a hook receptor, or hook and loop fabric). One end of strap 705 can then be attached to the end of ear hole extension 707 by these means of attachment and thus secure cover 702 around pillow 700.

Figure 14A:
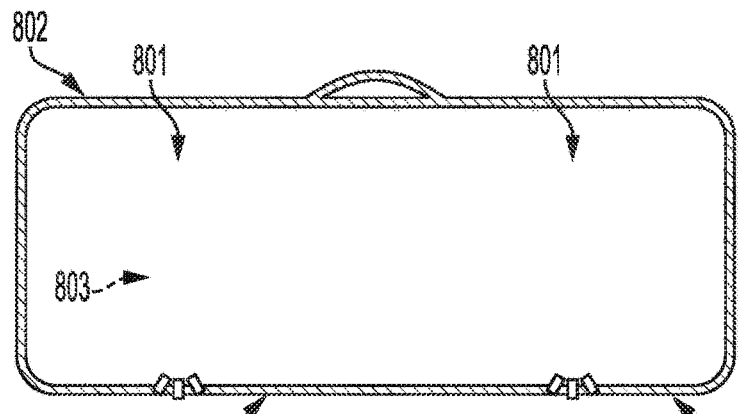
FIGS. 14A, 14B, and 14C schematically depict a pillow according to an embodiment enclosed within another pillow cover.
Figure 14B:
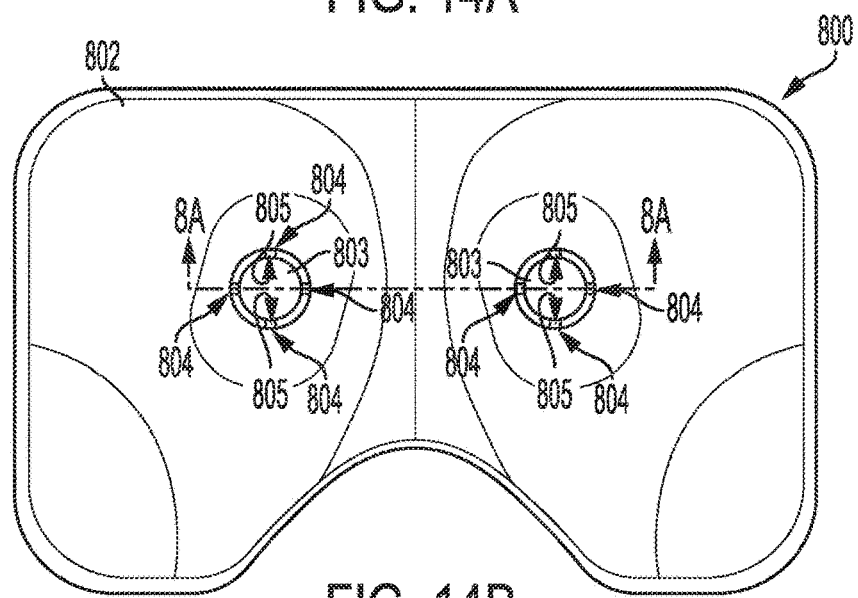
Figure 14C:
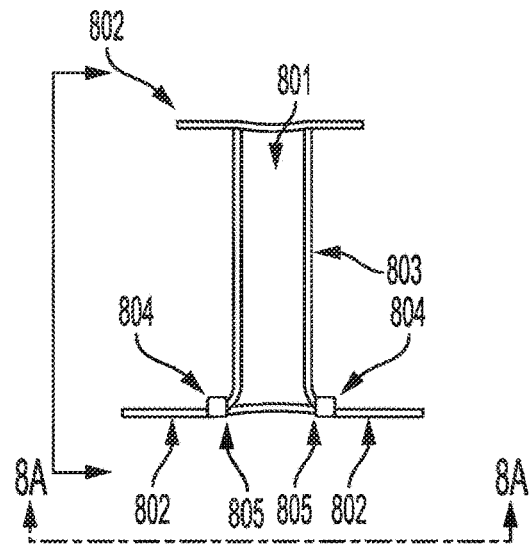
Figure 14A:
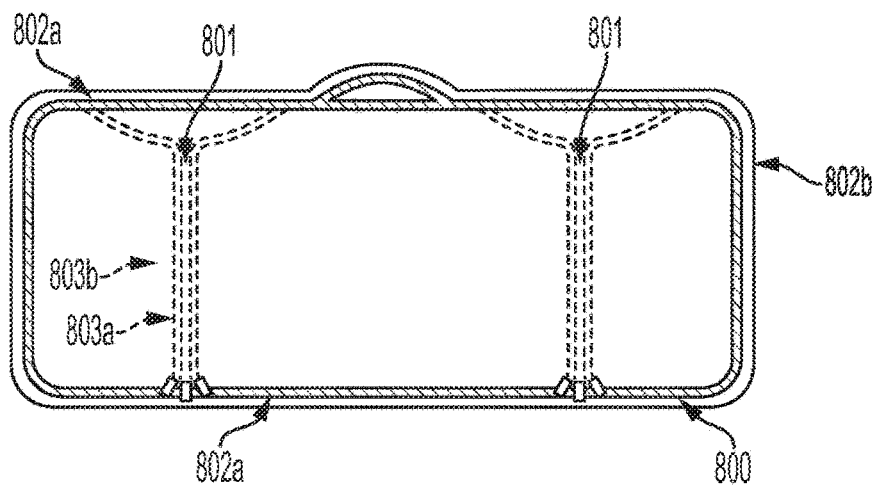
Figure 14B:
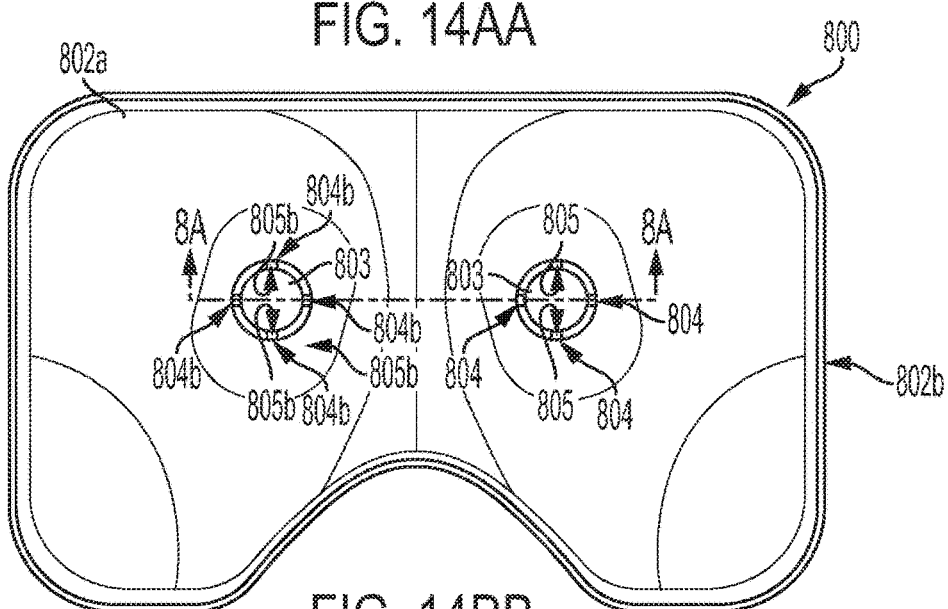
Figure 14C:
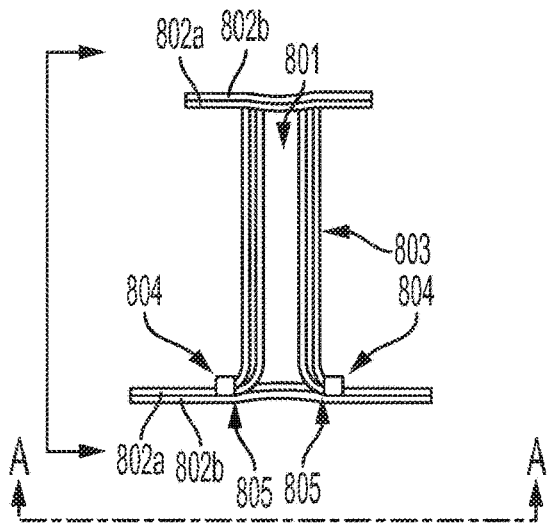

FIG. 14A shows a side view of another embodiment of a top section of a pillow 800 with a cover 802 that fits snugly around pillow 800. In this embodiment, the pillow cover 802 includes extension covers 803 that fit in through the recessed ear holes 801. FIG. 14B is a plan view of the bottom surface of top section of pillow 800 with cover 802 fitting snugly around pillow 800 and the circumference of the bottom sides of recessed ear holes 801. In this embodiment, the recessed ear hole extension covers 803 can include buttons 805, which can be attached to the extension covers using a variety of different mechanisms (e.g., they can be sewn or glued to the extension covers). Further, portions of the bottom side of the cover surrounding the recessed ear holes 801 can include receptacles 804 for receiving the buttons, thereby securing the cover around the pillow. FIG. 14C shows cutaway view of axis A-A (FIG. 14B) in which recessed ear hole extension covers 803 with buttons 805 extend into, and through, the recessed ear holes 801 and are attached to cover 802 using the buttons 805.

FIG. 14AA schematically depicts another embodiment of the pillow 800 that is enclosed within an inner cover 802a and an outer cover 802b. In some embodiments, the inner cover 802a fits snugly around the pillow 800 and the outer cover 802b fits snuggly around the inner cover 802a. The inner cover 802a includes an extension portion 803a that extends through the ear hole 801 and a passage provided by an extension portion 803b of the outer cover 802b. FIG. 14BB is a plan view of the bottom surface of the top section of the pillow 800 showing the second cover 802b fitting snuggly around the first cover 802a, which in turn covers the circumference of the bottom sides of the recessed ear holes 801. In this embodiment, the extension portion 803b can include buttons 805b that can be received by receptacles 804b, which are provided in the bottom side of the inner and outer covers 802a and 802b in the vicinity of the ear holes 801, to secure the covers around the pillow. By way of further illustration, FIG. 14CC shows a cut-away view of axis A-A (FIG. 14BB) in which extension portion 803a extends through a passage provided by the extension cover 803b. As discussed above, in this embodiment, the extension portions 803a and 803b are attached to the bottom sides of the covers using the buttons 805b. In other embodiments, other mechanisms, such as using an adhesive and/or sewing, can be employed to secure the covers to the pillow.

In some embodiments, any of the covers, and in some cases all of the covers, can be treated with an anti-microbial and/or an anti-pest agent.

Figure 14E:
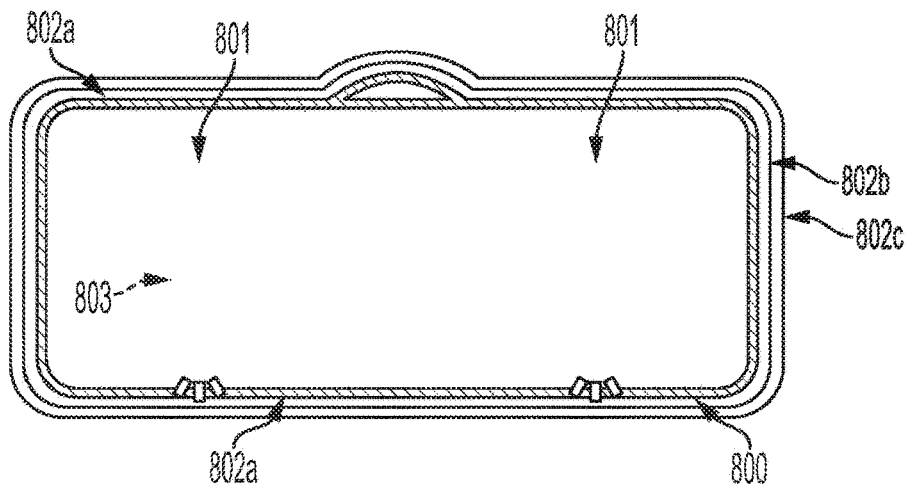
FIG. 14E schematically depicts another embodiment of a pillow, which is enclosed within three covers.
Figure 14F:
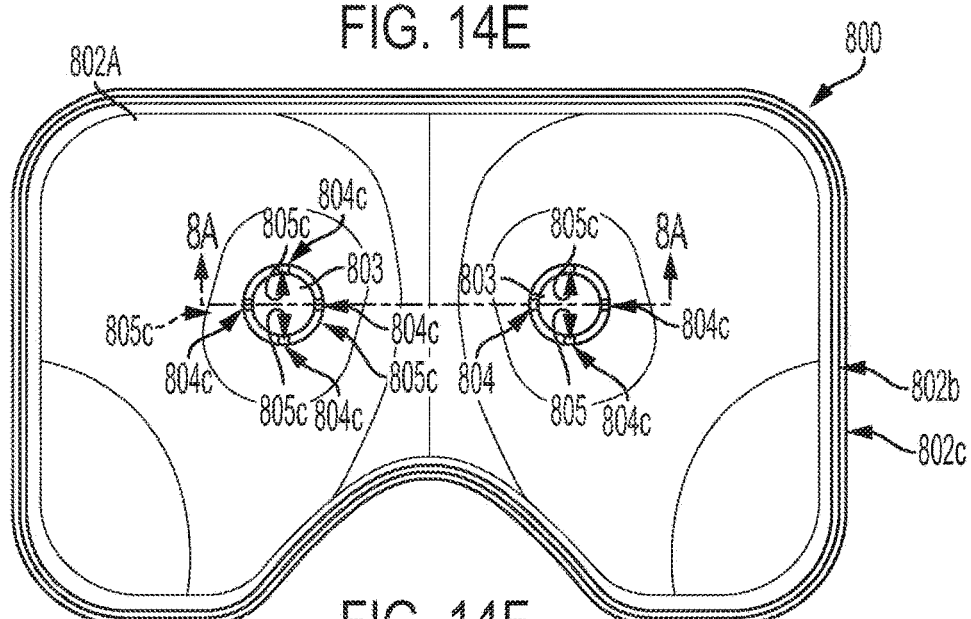
FIG. 14F is a plan view of the bottom surface of the top section of the pillow shown in FIG. 14AA, illustrating the third cover fitting snuggly around the second cover.
Figure 14G:
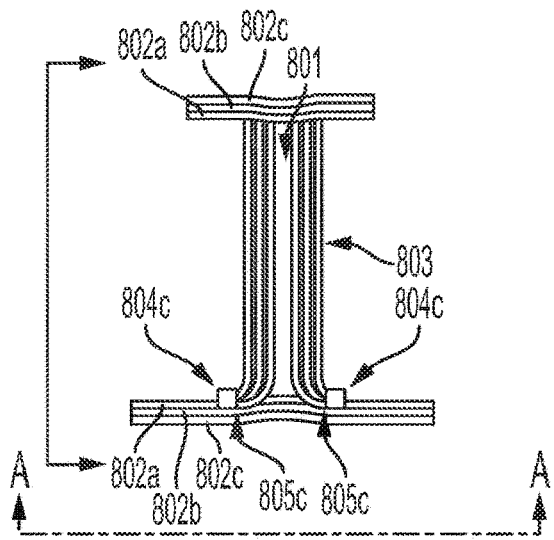
FIG. 14G shows a cut-away view along axis A-A of the pillow depicted in FIG. 14F.

FIG. 14E schematically depicts another embodiment in which the pillow 100 is enclosed by three covers, namely, the above covers 802a and 802b as well as a third cover 802c that fits snuggly around the cover 802b. An extension portion 803c of the cover 802c passes through a passage provided by the extension portions of the covers 802a and 802b through the ear hole 801. FIG. 14F is a plan view of the bottom surface of the top section of the pillow 800 showing the third cover 802c fitting snugly around the second cover 802b and covering the circumference of the bottom sides of the recessed ear hole 801. In this embodiment, the extension portion 803c of the cover 802c includes buttons 805c, which can be received by receptacles 804c provided on the bottom sides of the covers 802a, 802b, and 802c in the vicinity of the ear hole 801 to secure the covers to the pillow. In other embodiments, other mechanism, such as glue or sewing, can be employed to secure the covers to the pillow. FIG. 14G shows cut-away view of axis A-A (FIG. 14F) in which the extension portion 803c extends through the ear hole 801 and is secured to the pillow via the buttons 805c. Alternatively, as discussed in more detail below, the extension portions of the covers can be attached to the bottom sides of the covers using one or more zippers.

Figure 14H:
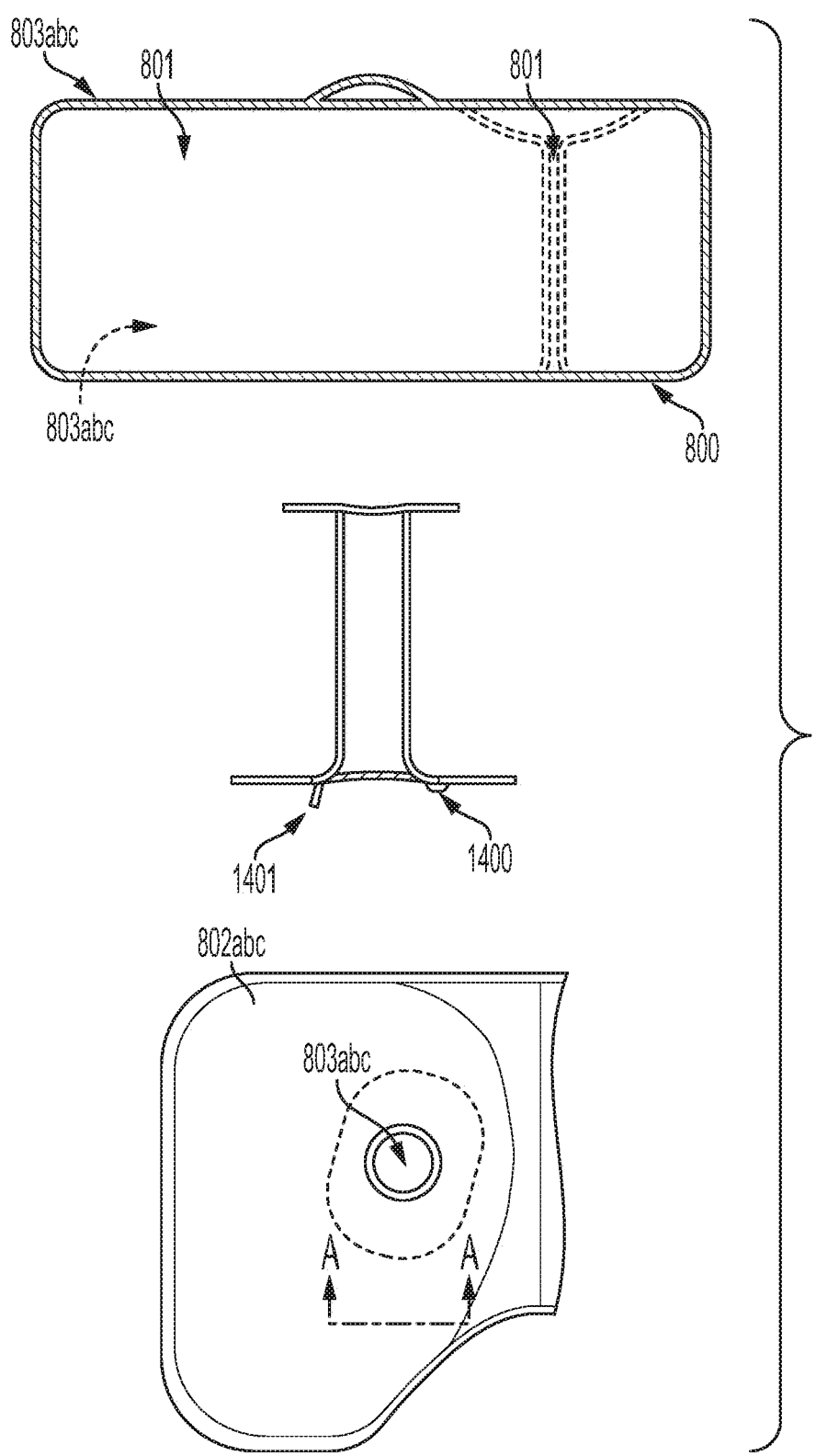
FIG. 14H schematically depicts an embodiment of a pillow according to the present teachings, which is enclosed by three covers secured around the pillow via a zipper.

FIG. 14H schematically depicts an embodiment of the pillow 800 in which the extension portions 803a, 803b, and 803c of the covers 802a, 802b, and 802c can be attached to the bottom sides of the covers in the vicinity of the ear hole 801 using a zipper 1400 having a zipper pull 1401, which allows the zipper to be opened and closed to facilitate the placement of the covers around the pillow and securing the covers to the pillow. In some embodiments, the zipper 1400 and the zipper pull 1401 can be constructed into an inner cover, e.g., 802a (e.g., in the extension portion 803a), to be hidden from view.

Figure 15:
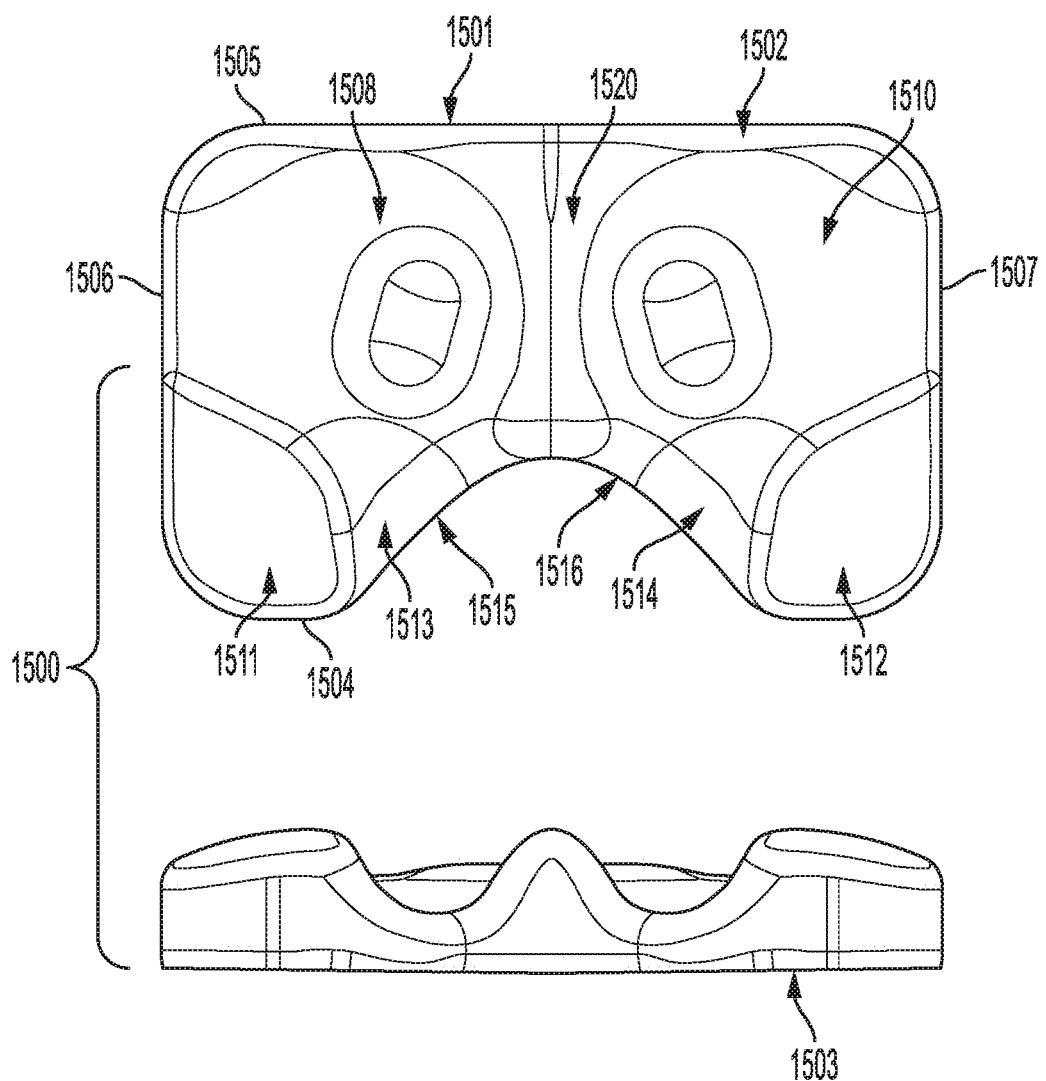
FIG. 15 schematically depicts a pillow according to an embodiment, which is formed of a single polymeric piece.

Although in this embodiment, the above apparatuses for airway management include two pieces, i.e., a top section and a bottom section, that can be removably and replaceably engaged with one another, in other embodiments, an apparatus according to the present teachings for airway management can be formed of a single piece. By way of example, FIG. 15 schematically depicts an apparatus 1500 for airway management that is formed as a substantially rectangular-shaped block 1501, which extends axially between a top surface 1502 and a bottom surface 1503 and laterally between a front surface 1504, a back surface 1505, a left side surface 1506 and a right side surface 1507. The apparatus 1500 is similar in all respects to the top section of the apparatus 100 discussed above, except that the bottom surface 1503 of the apparatus 1500 is substantially flat so as to allow positioning it on a flat surface. In particular, the apparatus 1500 includes left and right head-receiving portions 1508/1510, left and right chin supports 1511/1512, left and right recess neck openings 1513/1514, left and right shoulder-receiving recesses 1515/1516, and a raised ridge 1520, which separates the left portion from the right portion.

Thus, similar to the previous embodiments, the pillow 1500 allows placing a user in a left or a right lateral decubitus position with the user's head received and supported in the head-receiving portions and user's neck and shoulders supported by the recess neck openings and the shoulder-receiving recesses.

Figure 16A:
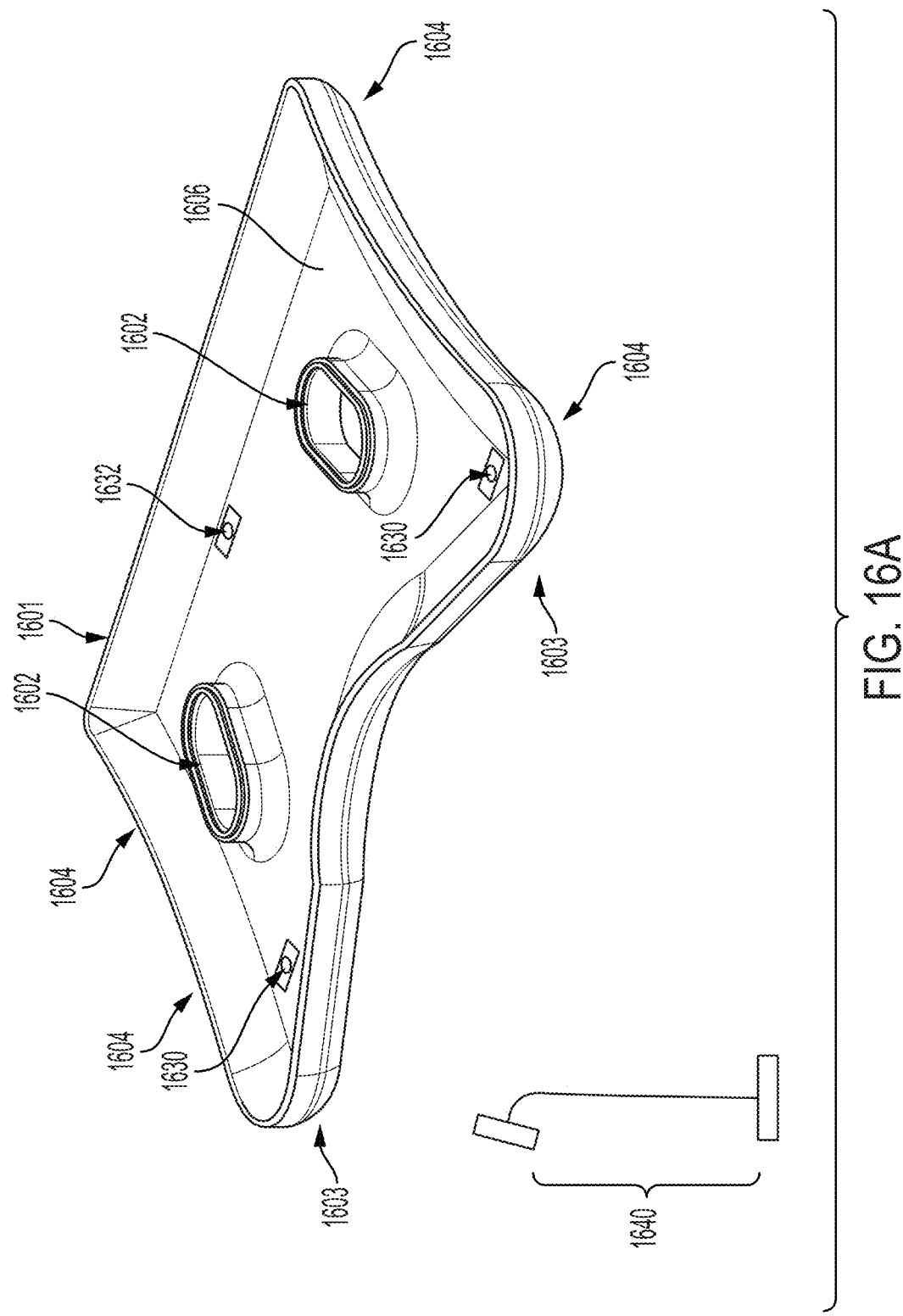
FIG. 16A schematically illustrates a front perspective view of an embodiment of a stackable height-adjusting insert, which can be used with an apparatus according to the present teachings.

FIG. 16A schematically illustrates a front perspective view of an embodiment of a stackable height-adjusting insert 1601 (herein also referred to as the height-adjusting element or height-adjusting wedge), which can be used with an apparatus according to the present teachings to adjust the height of the apparatus. The stackable height-adjusting insert 1601 extends from a front side 1603 to a back side 1605 and further extends between two lateral sides 1604. The height-adjusting insert 1601 further includes flanged recessed ear holes 1602. The flanged recessed ear holes 1602 are configured to fit snugly and matingly into the recessed ear holes of the apparatus (such as ear hole 111a/111b depicted in FIG. 2B). Further, the top surface of the height-adjusting insert 1601 is configured to fit snuggly and matingly into the bottom surface of the apparatus (not shown).

Figure 16B:
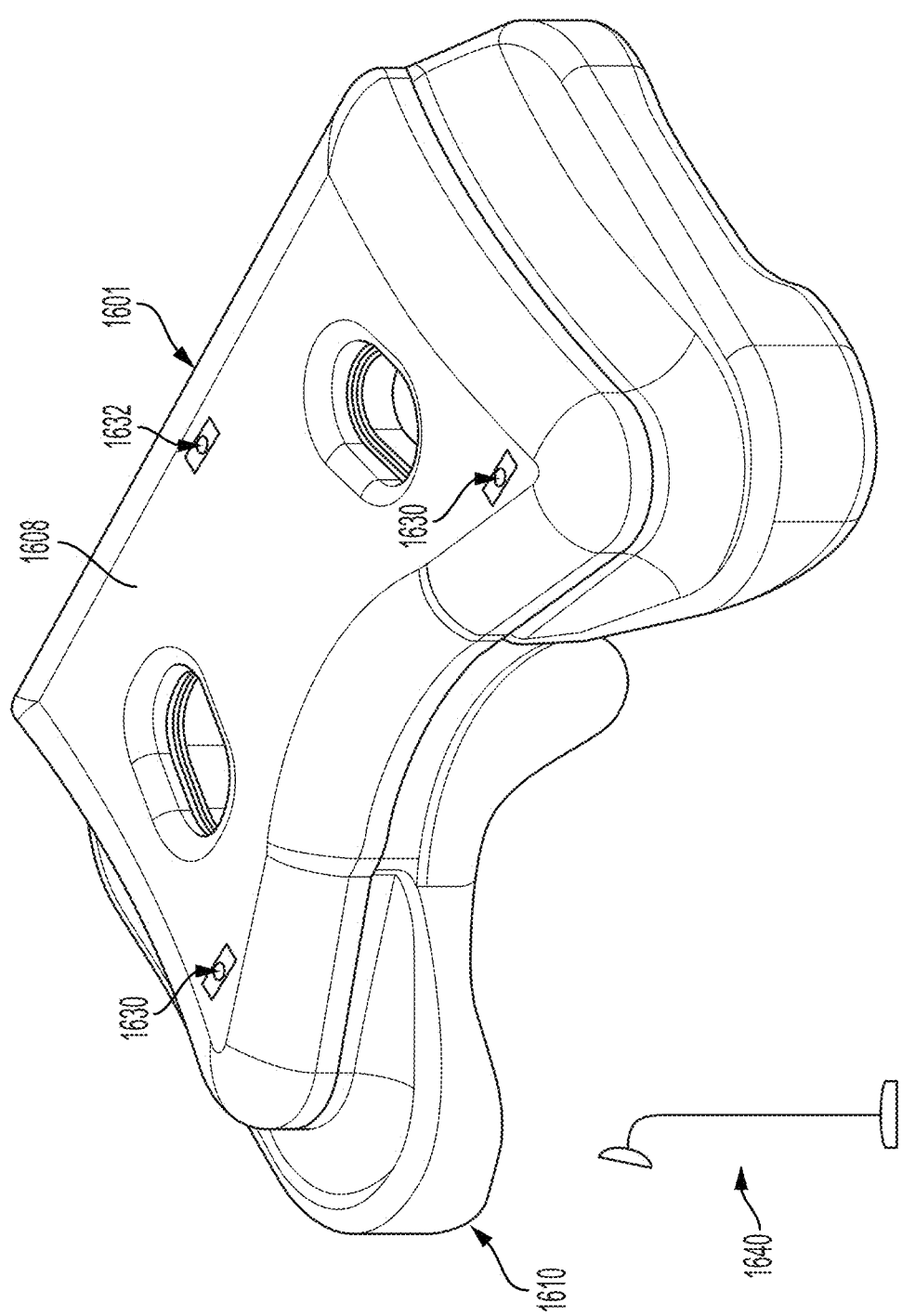
FIG. 16B illustrates a perspective view of an apparatus according to an embodiment of the present teachings that is coupled to the head-adjusting insert depicted in FIG. 16A.

FIG. 16B illustrates a perspective view of an apparatus 1610 that is coupled to the height-adjusting insert 1601, where the height-adjusting insert 1601 fits snugly and matingly into the bottom side of the apparatus.

Figure 16C:
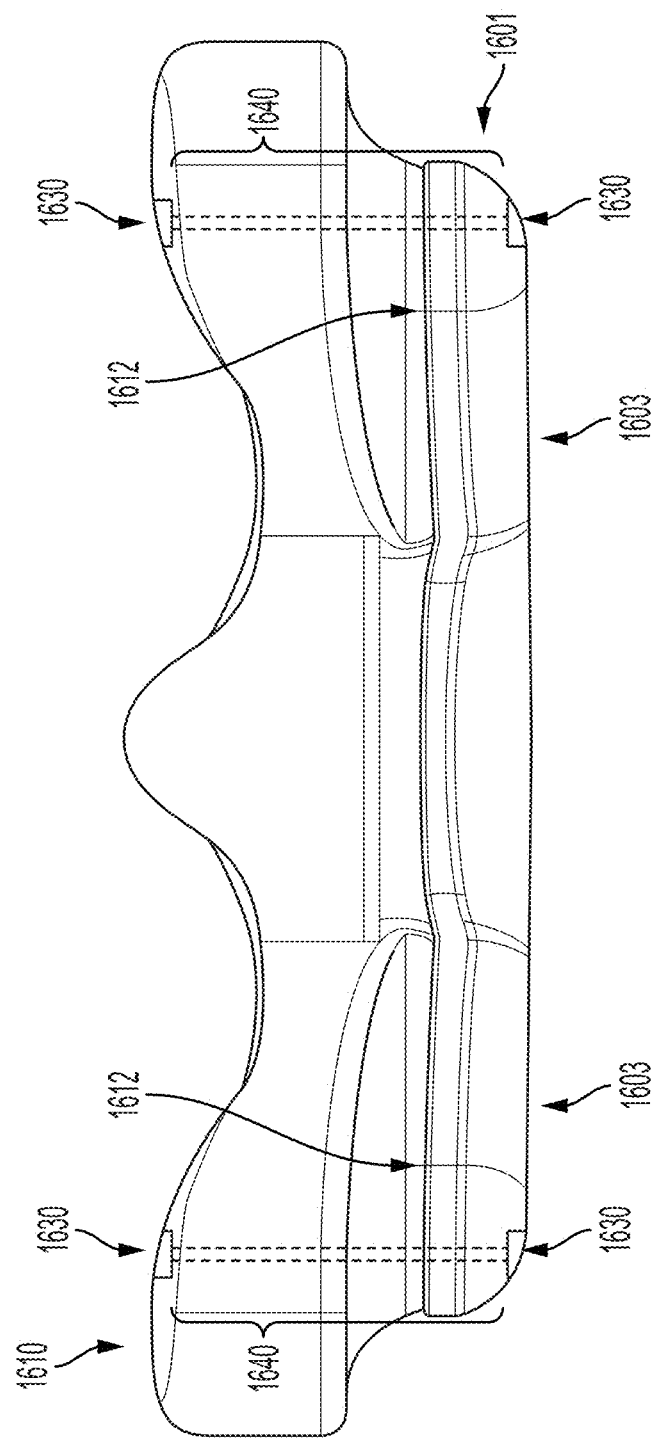
FIG. 16C schematically depicts a front plan perspective view of the apparatus of FIG. 16B coupled to the height-adjusting insert according to one embodiment of the apparatus.

FIG. 16C schematically depicts a front plan perspective view of the apparatus 1610 coupled to the height-adjusting insert 1601. Specifically, in this embodiment, the height-adjusting insert 1601 fits snugly and matingly into the bottom surface of the apparatus. In this embodiment, the contour of the front side 1603 of the height-adjusting insert and that of the front side 1612 of the apparatus substantially conform to one another.

With reference to FIGS. 16A and 16B, in this embodiment the height-adjusting insert 1601 includes slot holes 1630 that are substantially aligned with respective through holes provided in the apparatus (not visible in FIG. 16B because they are covered by the insert). The holes 1630 are provided in the chin supports of the apparatus. The height-adjusting insert 1601 further includes a slot hole 1632 that is substantially aligned with a respective hole provided in the apparatus at a side thereof that is opposite to the side at which the chin supports are located. Mount toggles 1640 can be passed through the slot holes 1630 and 1632 into and through the corresponding holes in the apparatus in order to removably and replaceably attach the height-adjusting inserts to the apparatus. In this embodiment, each of the mount toggles 1640 includes a stretchable cord 1640a that is attached at its ends to handles 1640b and 1640c, which are configured to be seated in the slots associated with the holes.

Figure 16D:
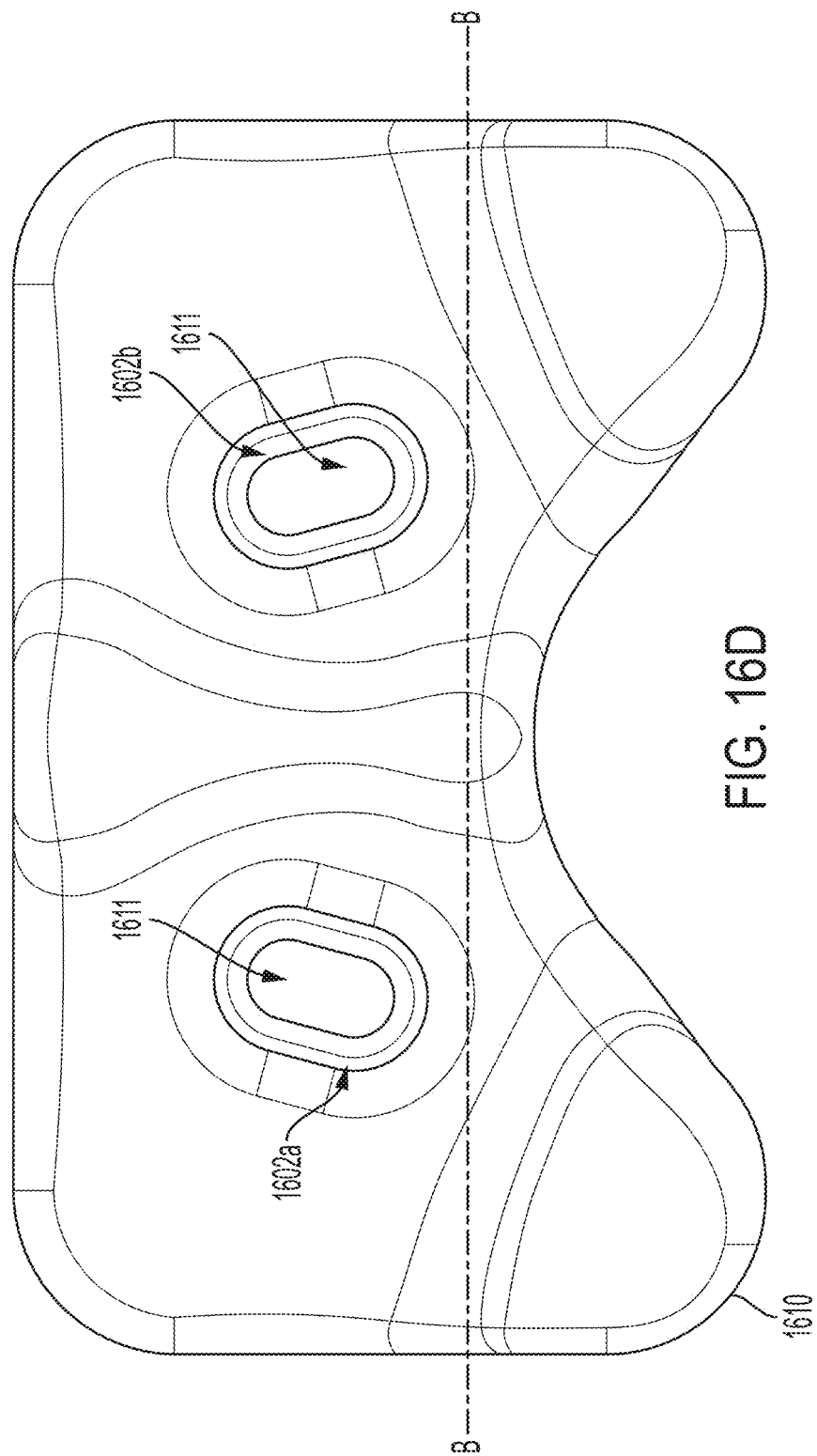
FIG. 16D schematically depicts a top plan perspective view of the apparatus shown in FIG. 16C with the height-adjusting insert fitting snuggly around the apparatus.

FIG. 16D schematically shows a top plan perspective view of an embodiment of the apparatus 1610 with the height-adjusting insert 1601 fitting snugly and matingly into the apparatus 1610. In this embodiment, the apparatus and the height-adjusting inserts do not include holes for coupling the two together via one or more mounting toggles. Rather, in this embodiment, the height-adjusting insert can be fitted with the apparatus via frictional fit. FIG. 16D further shows that the flanges 1602a/1602b of the height-adjusting insert 1601 are received by ear holes 1611 of the apparatus to provide a snug fit between the insert and the apparatus.

Figure 16E:
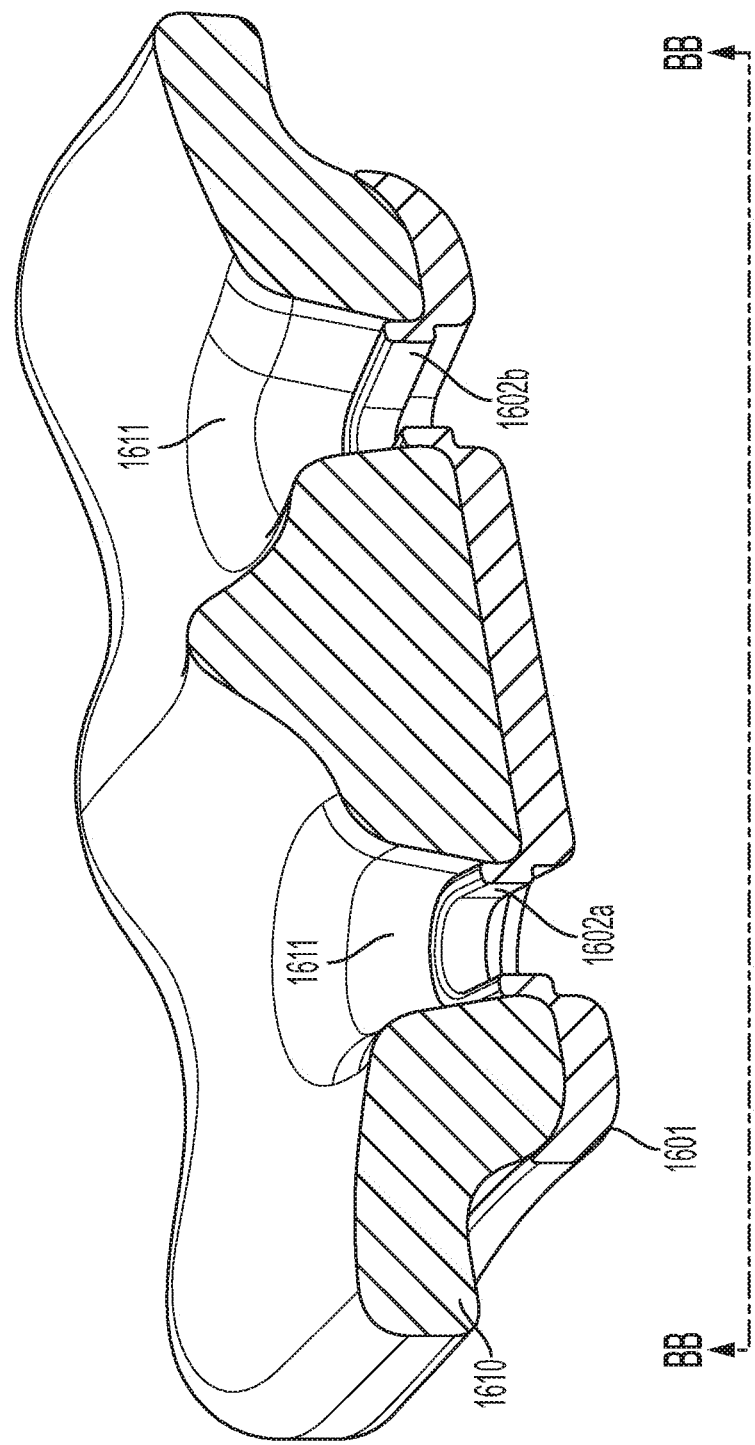
FIG. 16E shows a schematic cut-away view along axis B-B of the embodiment shown in FIG. 16D.

FIG. 16E shows a cutaway view along B-B axis from FIG. 16D depicting the stackable height-adjusting insert 1601 fitting matingly and snugly into the bottom surface of the apparatus 1610 with the flanged recess ear holes fitting snugly and matingly into recessed ear holes 1611.

Figure 16F:
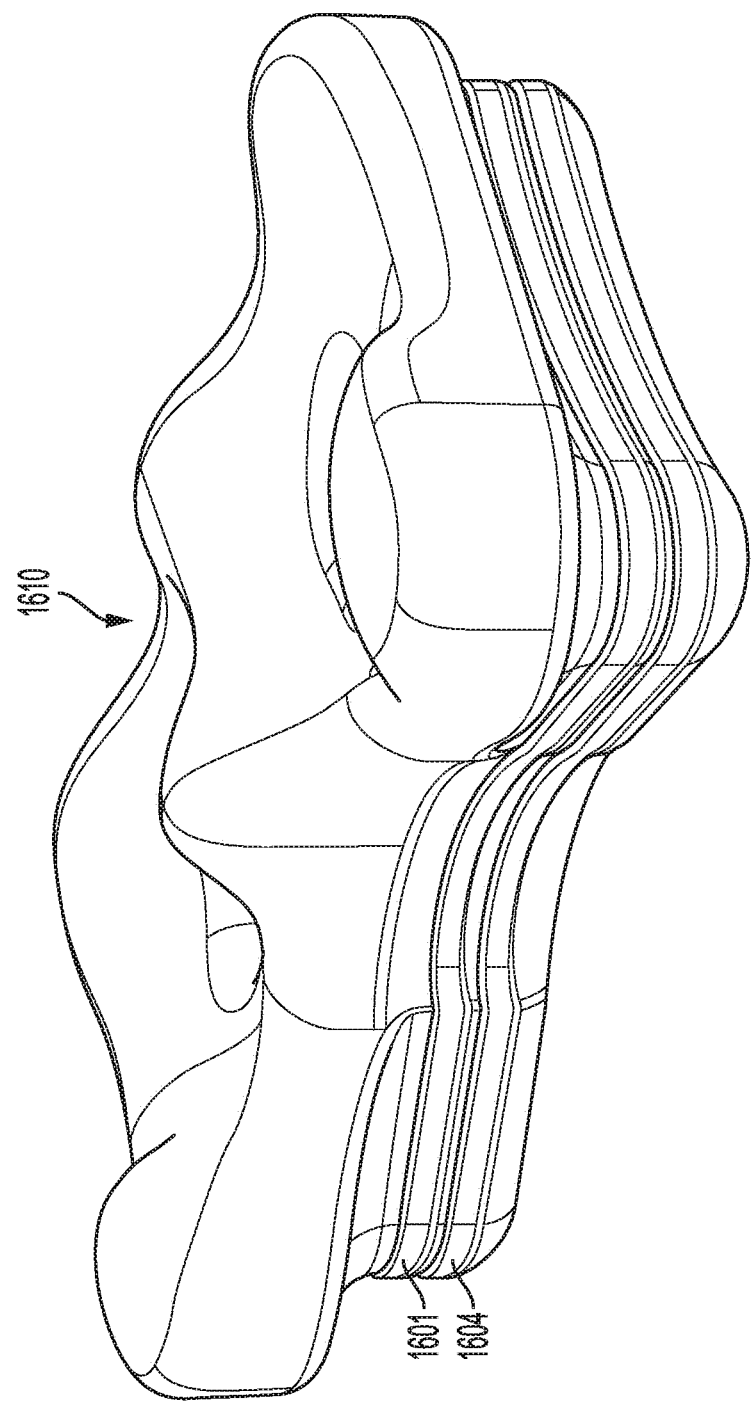
FIG. 16F is a schematic perspective view of an apparatus according to an embodiment that is coupled to two height-adjusting inserts.
Figure 16G:
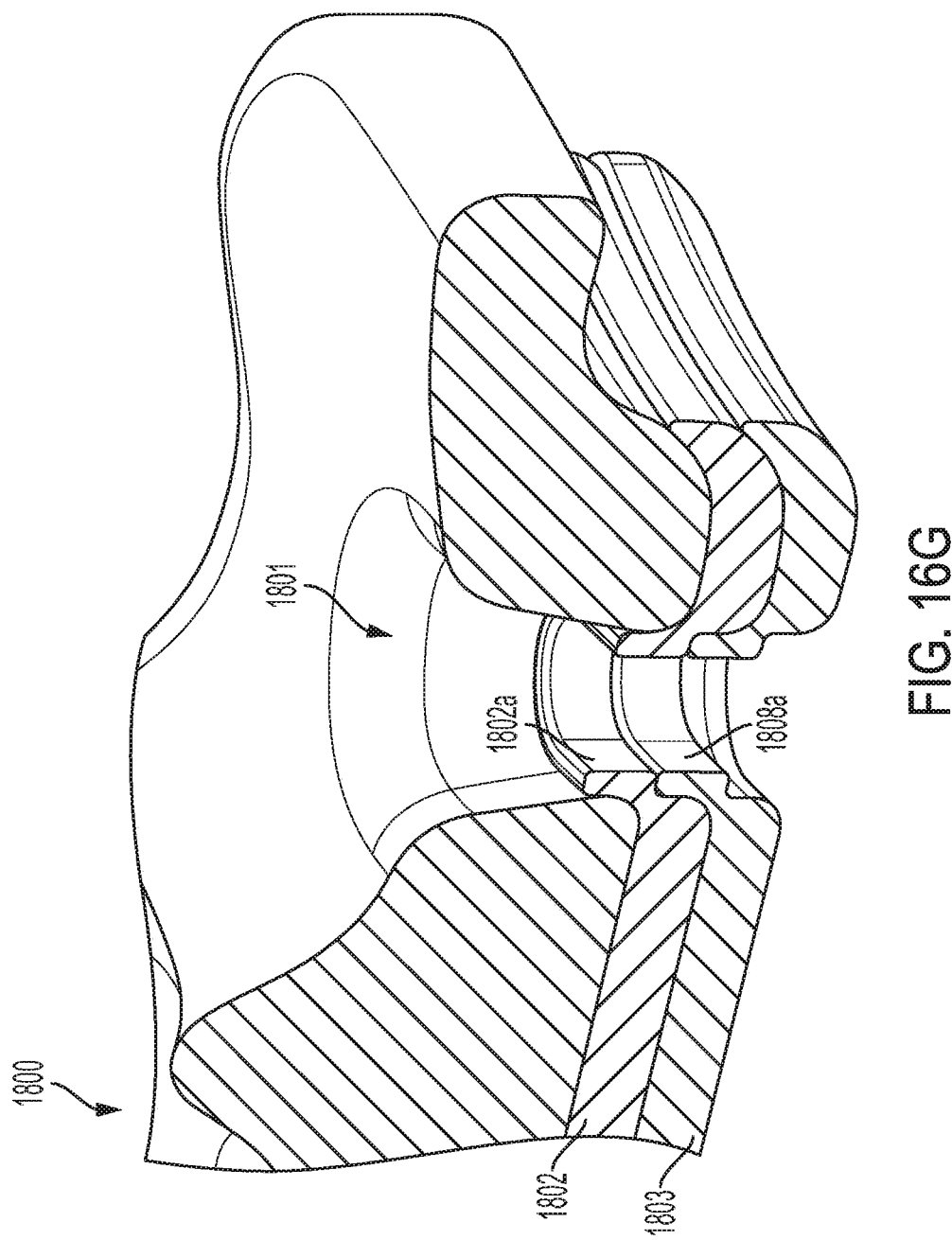
FIG. 16G is a schematic cut-away view of the apparatus shown in FIG. 16F.

FIG. 16F shows a perspective view of the apparatus 1610 that is coupled to the above stackable height-adjusting insert 1601, which is in turn coupled to a second stackable height-adjusting insert 1604. The first height-adjusting insert 1601 is contoured to fit matingly and snugly into the bottom surface of the apparatus, and the second height-adjusting insert 1604 is contoured to fit matingly into the bottom surface of the height-adjusting insert 1601. FIG. 16G illustrates a cutaway view of an apparatus 1800 according to an embodiment of the present teachings for supporting the head and neck of a user for airway management, which includes a single ear hole 1801 and which is coupled to first and second inserts 1802 and 1803. The inserts 1802 and 1803 include flanged recessed ear holes 1802a and 1803a, where the flanged recessed ear hole 1802a is received in the ear hole 1801 and the flanged recessed ear hole 1803a is received in the opening provided by the flanged recessed ear hole 1802a.

Figure 17:
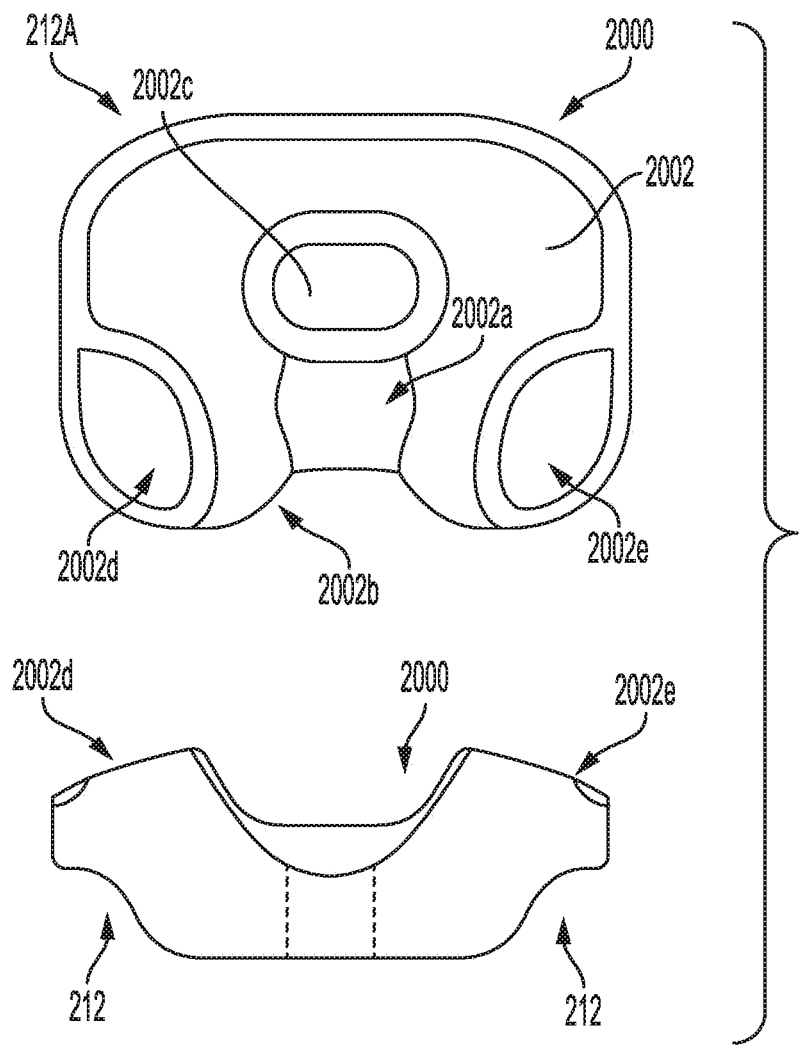
FIG. 17 schematically depicts a pillow according to an embodiment in which the pillow includes only one head-receiving portion.

FIG. 17 schematically depicts a pillow 2000 according to an embodiment in which the pillow includes only one neck and head receiving areas and one shoulder receiving portion. FIG. 17 shows the plan view of top surface 2002 of the pillow 2000 and a side view of the pillow, illustrating a neck receiving opening 2002a, shoulder receiving portions 2002b, ear hole 2002c, and chin blocks 2002d and 2002e. In this embodiment, the pillow 2000 includes arm cut-outs 2003a/2003b for receiving at least a portion of a user's arm when the user's head is received in the head-receiving area. In some embodiments, the top surface of the pillow as well as the lateral surfaces of the chin blocks can have contoured surfaces having compound slopes, similar to that discussed above in connection with embodiments in which the pillow includes two head-receiving portions.

With reference to FIGS. 18A-1, 18A-2, 18B, 18C, 18D, 18E, 18F, 18G, and 18H, one embodiment of an apparatus 3700 according to the present teachings includes two chin supports 3701' each of which is associated with a portion of the apparatus intended for accommodating a user in the left or right lateral position. Each chin support 3701' includes a raised chin support structure 3702' having a top surface 3702. As shown in FIGS. 18A-1, 18A-2, 18D and 18E, a through hole 3709 extends from the top surface 3702 of each chin support structure 3702' to the back surface 3799 of the apparatus. At the bottom of the apparatus, the through hole 3709 terminates in a slot 3701. A plurality of chin support blocks 3703, 3704, and 3705 are provided, where each of the chin support blocks 3703, 3704, 3705 can removably and replaceably engage with a corresponding chin support structure 3702', in a manner described in more detail below.

Figures 1, 18A:
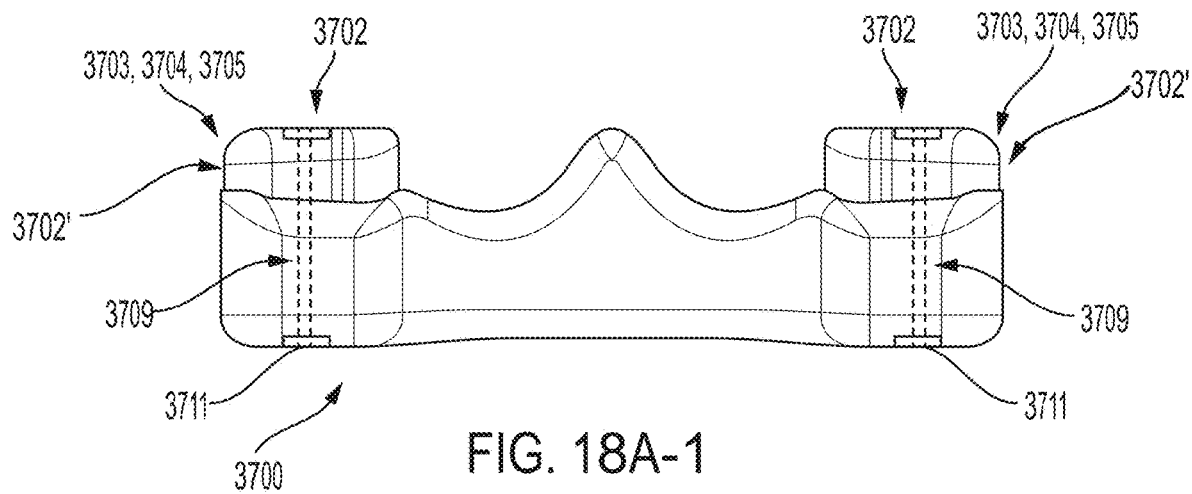
FIG. 18A-1 is a schematic side view of an apparatus for supporting the head and the neck of a user according to an embodiment disclosed herein.
Figures 2, 18A:
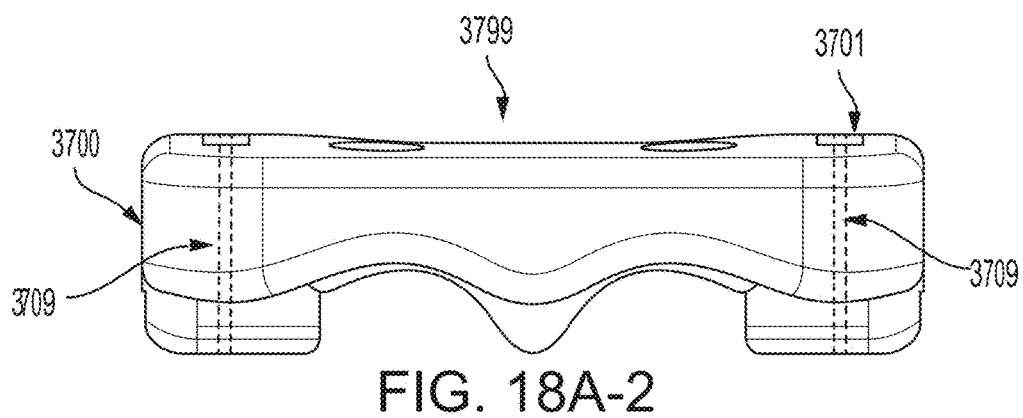
Figure 18B:
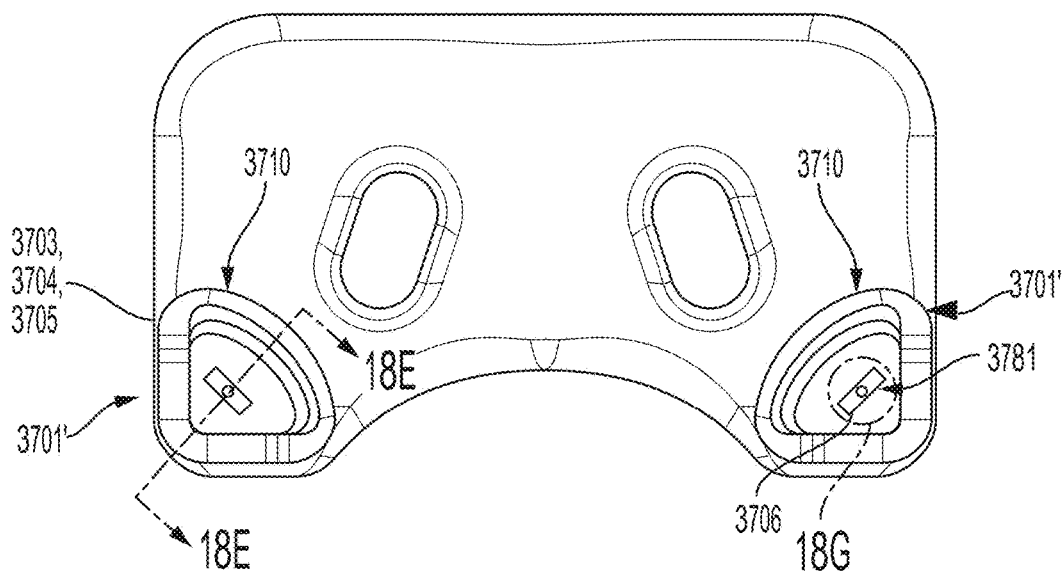
FIG. 18B is a schematic plan view of the apparatus depicted in FIG. 17A.
Figure 18G:
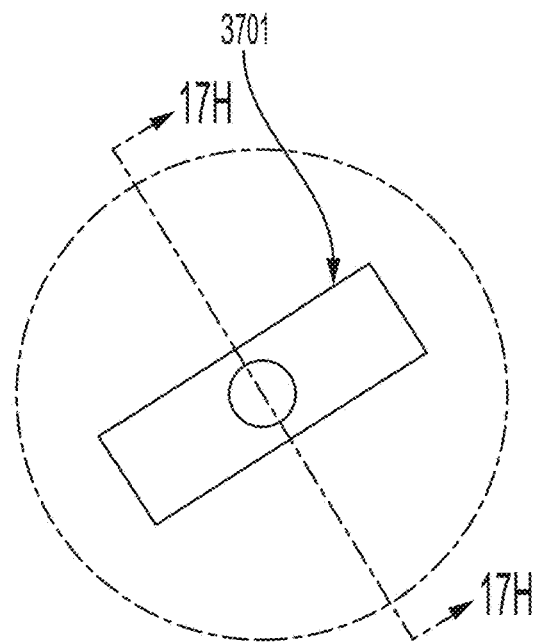
FIG. 18G is a close-up view a portion of the apparatus depicted in FIG. 18B illustrating a slot provided in the top surface of the removable chin blocks.
Figure 18H:
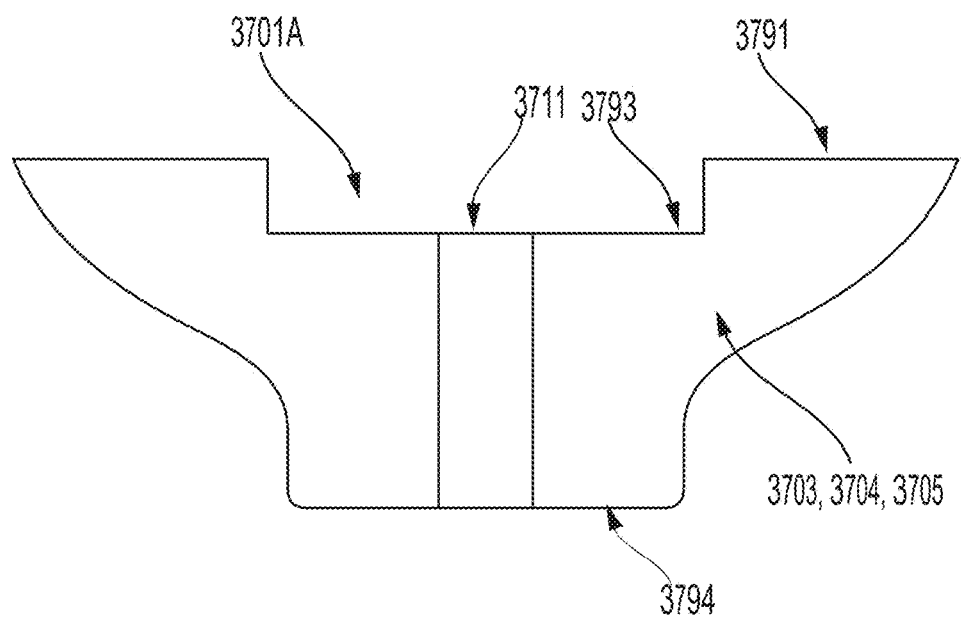
FIG. 18H shows a cut-away view of Section B-B from FIG. 18G.

Specifically, as shown in FIG. 18H, which illustrates a chin support blocks 3703, 3704, 3705 in an inverted configuration, each chin support blocks 3703, 3704, 3705 can include a cavity 3701A that can removably and replaceably receive the chin support structure 3702'. As shown, a chin support blocks 3703, 3704, and 3705 can include a through hole 3711 that extends from the top surface 3793 of the cavity of the chin support blocks 3703, 3704, 3705 to a bottom surface thereof 3794. Further, the top surface of each chin support block cavity 3793 can include a slot 3781 that contains the top opening of the through hole 3711. By way of example, the slot 3781 can be molded or cut in the top surface 3793 of the chin block 3703, 3704, 3705. As discussed above, chin support blocks of the embodiments disclosed herein, such as chin support blocks 3703, 3704, and 3705, can be removably and replaceably engaged with the raised chin support structure 3702' to accommodate users having different morphologies.

Upon engagement of a chin support blocks 3703, 3704, 3705 with a corresponding chin support structure 3702', the through hole 3711 extending through the chin support blocks 3703, 3704, 3705 is brought into substantial alignment with the through hole 3709 provided in the raised chin support structure 3703, 3704, 3705 such that together the through hole 3711 and the through hole 3709 provide a channel that extends from the top surface 3793 of the chin support block to the bottom surface of the apparatus 3799 through which a chin block mounting toggle 3706, as detailed below, can be passed.

In particular, with reference to FIGS. 18E and 18F, an adjustable chin support 3701' according to an embodiment of the present teachings can further include a chin block mounting toggle 3706 that can releasably couple a chin support blocks 3703, 3704, 3705 to a corresponding raised chin support structure 3702'. More specifically, the mounting toggle 3706 can include a stretchable and/or pliable cord 3711 that is configured to connect at its top and bottom ends to a top handle 3713 (herein also referred to as the top tab 3713) and a bottom handle 3712 (herein also referred to as the bottom tab 3712), respectively.

For coupling the mounting toggle 3706 to the chin support structure 3702', the top handle 3713 can be turned so as to be substantially parallel to the stretchable cord and can be passed through the hole 3701 at the bottom of the apparatus through the hole 3709 provided in the chin support structure to exit through the top opening of the hole 3709. The top handle 3713 can then be pulled and passed, together with a portion of the cord pulled out of the opening in the chin support structure, through the hole 3711 provided in any of the chin support blocks 3703, 3704, and 3705 and be secured within the slot 3781 provided on the top surface of that chin support block. In this manner, adjustable chin support blocks 3703, 3704, and 3705 with different sizes can be releasably coupled to the chin support structures with the top handle 3713 of the mounting toggle disposed in a slot 3781 provided on a top surface 3793 of the chin support block and the bottom handle 3712 of the mounting toggle disposed on a slot 3701 provided on the bottom surface of the apparatus. Once a chin support block is mounted on a chin support structure via the mounting toggle, the tension of the stretchable/pliable cord 3711 on the bottom handle (tab) 3712 and the top handle (tab) 3713, which rest in their respective slots, acts to maintain the engagement of the chin support blocks 3703, 3704, and 3705 with the mounting surface of the chin support structure.

FIG. 18E depicts a more detailed illustration of the mounting surface 3702 of the raised chin block structure onto which a replaceable chin support blocks 3703, 3704, 3705 can be mounted. In this embodiment, the top surface 3793 of each replaceable chin support blocks 3703, 3704, 3705 is substantially perpendicular to the side surface 3710, inner surface 3791 and the front surface 3708 (shown in FIG. 18D) of the replaceable chin support blocks 3703, 3704, 3705. The angle β between the side surface 3710 and top surface 3793 can vary between 80° and 100°. Additionally, the angle α between the top surface 3793 and inner support surface can vary between 80° and 100°. Inner surface 3791 can exhibit a compound curvature with angle grades varying between 20° and 60°. The compound slope of the inner surface 3791 can help support a user's neck and associated platysmal surface helping hold the head in a sniff position. FIG. 18E illustrates the chin block 3703, 3704, 3705 mounted on an inner mounting surface 3791 of a chin support structure with the handles of the mounting toggle seated in the top and bottom slots associated with the top and bottom openings of the hole extending through the chin support structure. It can be seen that the inner surface of the chin support block 3701 fits snuggly onto the mounting surface 3702 of the raised chin block structure.

Referring to FIG. 18C, in some embodiments, the shortest distance (L) between the center of an ear hole and an inner lateral surface of a chin support can be, e.g., in a range of about 3 inches to about 6 inches, e.g., in a range of about 3 inches to about 4 inches, or in a range of about 4 inches to about 5 inches, or in a range of about 5 inches to about 6 inches.

Figure 19A:
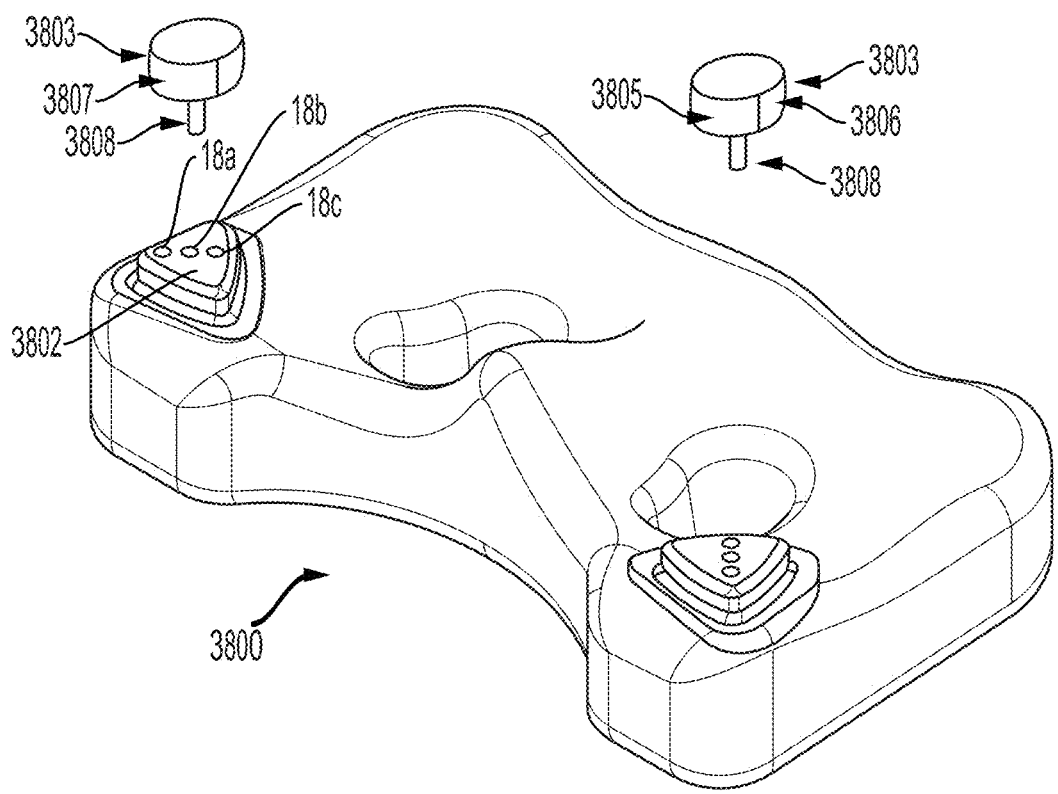
FIG. 19A is a schematic perspective view of an apparatus according to an embodiment having a chin support structure, which includes three holes for receiving a chin support block having a post configured for being received by the holes.
Figure 19B:
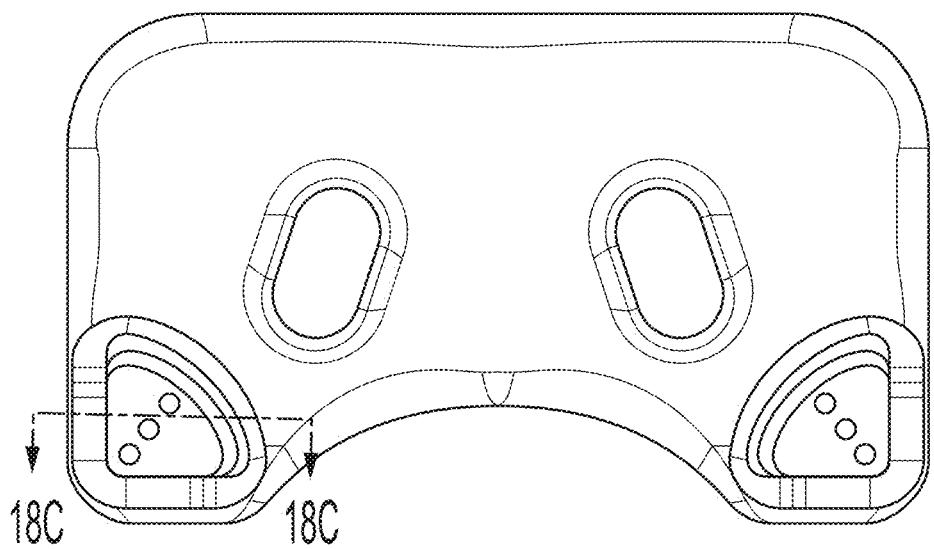
FIG. 19B is another perspective view of the apparatus of FIG. 19A.
Figure 19C:
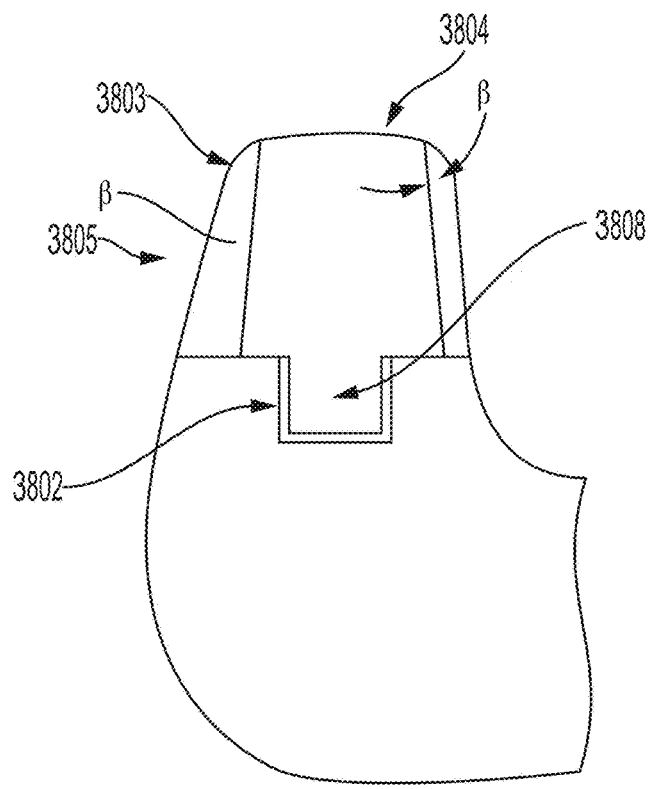
FIG. 19C is a cut-away view of Section A-A in FIG. 19B.

FIG. 19A illustrates a perspective of an embodiment of an apparatus 3800 according to the present teachings, which includes two or more chin block mount holes 3801a, 3801b or 3801c cut or molded into chin clock support surface 3802. In this embodiment, chin block 3803 can comprise a mount post (herein also referred to as a mounting post) 3808 attached onto the bottom of the chin block allowing the position of chin block 3803 to be moved or adjusted relative to the chin block support surface 3802. The top surface 3804 of chin clock 3803 in this embodiment can be substantially perpendicular to the side surface 3805, inner surface 3806 and the front surface 3807 of chin block 3803, and the angle β between side surface 3805 and top surface 3804 can vary between 80° and 100° while angle α between front surface 3807 and top surface 3804 can also vary by these amounts as well.

Additionally, the angle β between top surface 3804 and the inner support surface 3806 can vary between 80° and 100°. Further, the inner surface (3806) can exhibit a compound curvature with angle grades varying between 20° and 60°. The compound curvature of inner surface (3806) can support the user's neck and associated platsymal surface and help hold the user's head in the sniff position. The mount post 3808 can be shaped and sized to fit snuggly into the mounting holes 3801a, 3801b, 3801c and 3801d, thus securing the chin block 3803 onto the mounting surface 3802 of the chin support structure.

The chin block (3803) can be removed from one of the mounting holes from one position, via removing the mounting post from a respective mount hole, and can be placed in another position, via insertion of the mount post into another mount hole. In this manner, the position of the chin support blocks relative to the chin support structure can be adjusted so as to accommodate different users morphologies. Although in this embodiment three mount holes (3801a, 3801b, and 3801c) and one chin support block are illustrated, other embodiments can have other numbers of mount holes and chin support blocks, including different sizes of the chin support blocks, so as to accommodate different users morphologies.

Figure 20A:
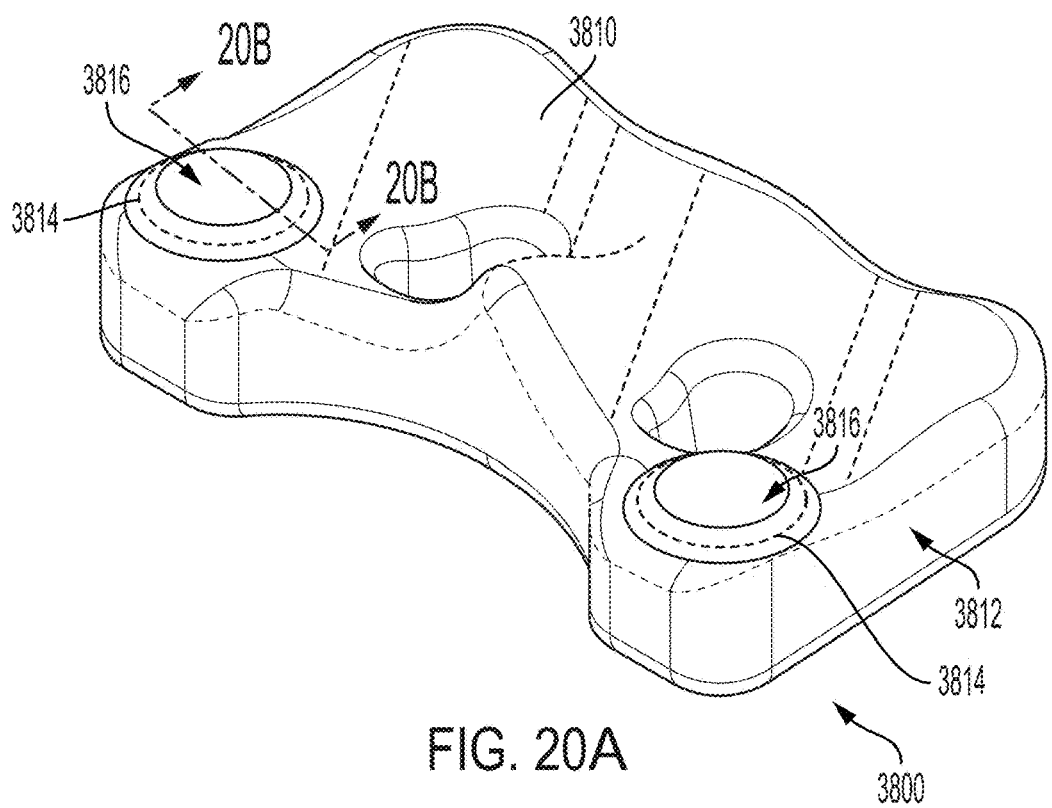
FIG. 20A schematically depicts an embodiment according to the present teachings that is encased in a cover.
Figure 20B:
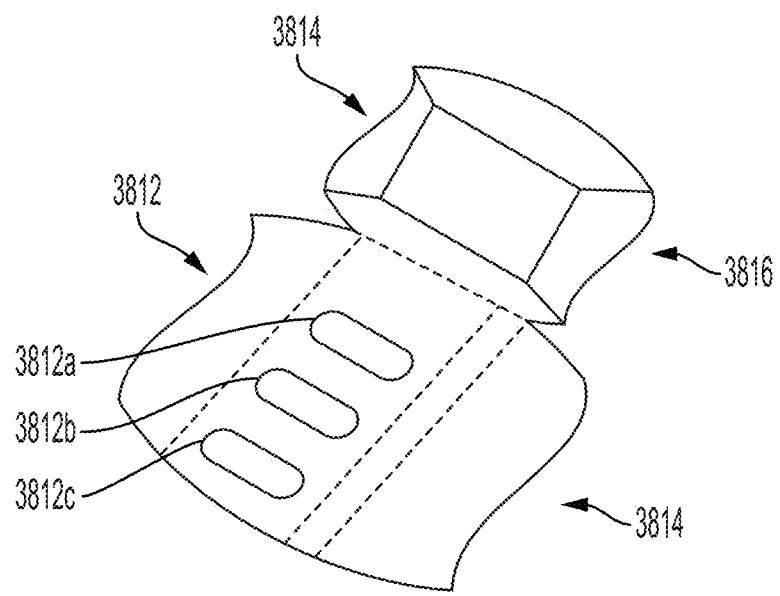
FIG. 20B schematically depicts that the separable sections of FIG. 19A are coupled to one another view a plurality of serrated indentations.

FIG. 20A illustrates the apparatus 3800 encased in a cover 3810 that includes three holes 3810a, 3810b, and 3810c, which are substantially aligned with the mount holes 3801a, 3801b and 3801c such that access to the mount holes can be provided with the apparatus encased in the cover with the zippered opening 3812. FIG. 20B illustrates that the cover can include a chin support pocket 3816, which can have a zippered closure 3814 that allows the pocket to be opened to receive one or more removable chin support blocks of various sizes (not shown in this figure). The three holes 3810a, 3810b, and 3810c allow positioning the chin support block in any of the holes, thereby adjusting the position of the chin support block.

Figure 21A:
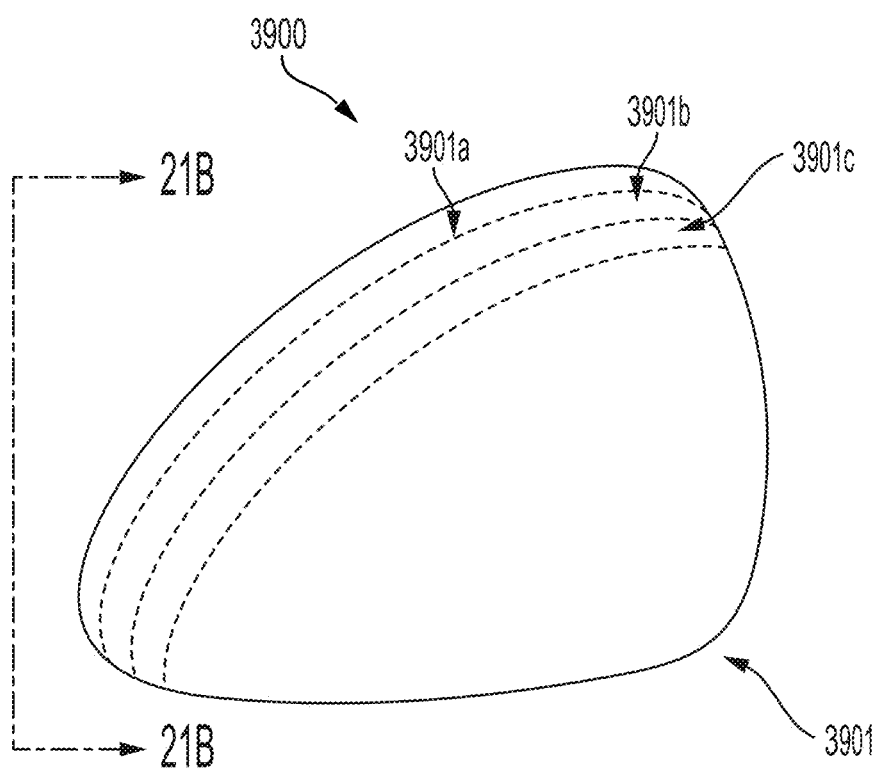
FIG. 21A schematically depicts an embodiment of an apparatus according to the present teachings.
Figure 21B:
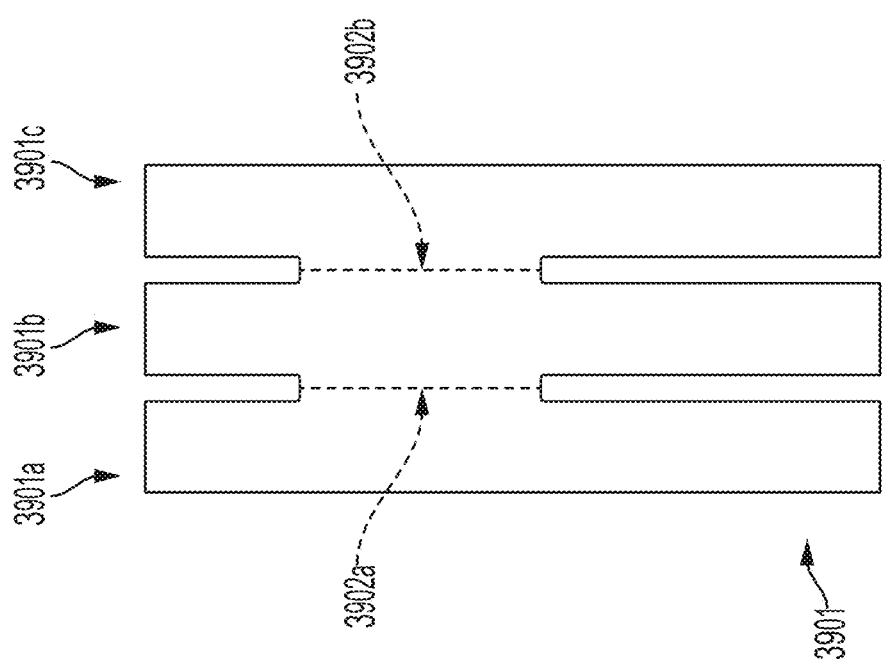
FIG. 21B illustrates another schematic embodiment of an apparatus according to the present teachings.

FIGS. 21A and 21B depict schematically an embodiment of an apparatus 3900 according to the present teachings, which includes a chin support block 3901. Chin support block 3901 includes a plurality of removable sections 3901a, 3901b, 3901c that can be removed in succession to vary the width of the chin block between ¼ and ½ inches. More specifically, the removable sections 3901a, 3901b, 3901c are coupled to one another via serrated indentions 3902a, 3902b which allow chin block sections 3901a, 3901b, 3901c to be peeled away. These chin block sections may have a width varying between ¼ and ½ inches. Although the chin block 3901 in this example is shown as having three chin block sections, it is understood that other embodiments can have two chin block sections, while still other embodiments can have three or more such chin block sections that can be removed, e.g., in succession, to adjust the width of the chin support block to ensure that it would fit the morphology of a user. The chin support block shown in this example can be attached or formed into the apparatus or can be attached using other components described herein, such as those shown in FIGS. 18A-19C.

Figure 22:
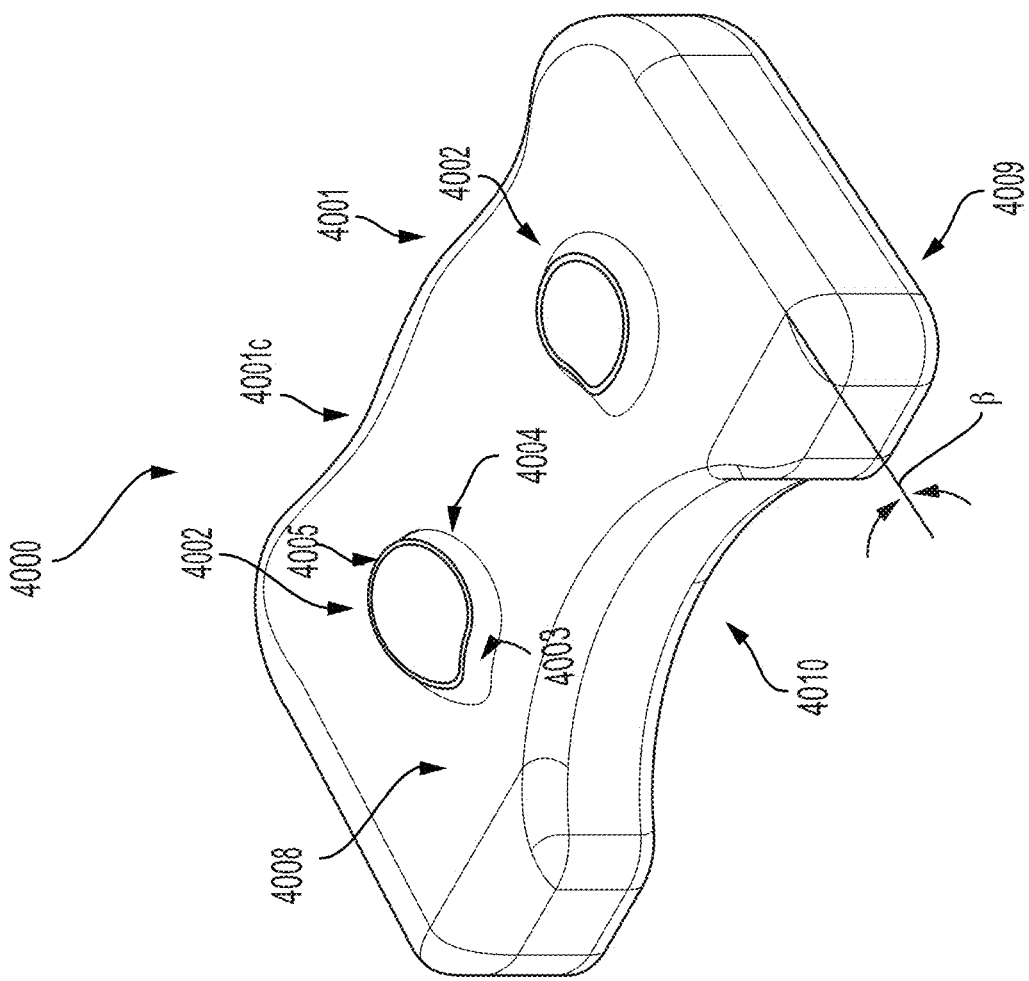
FIG. 22 depicts embodiments of a covers according to the present teachings.

FIG. 22 illustrates a front perspective view of an embodiment of a height-adjusting insert 4001 including flanged recessed ear holes 4002 having a front side 4003, lateral sides (4004), and a back side 4005. The front 4003, lateral 4004, and back 4005 sides of the flanges recessed ear holes 4002 can be configured such that they correspond to the sides of the apparatus 4000 (e.g., the front side 4003 can correspond to the front side 4010 of the apparatus).

The height adjusting insert 4001 can also include a top surface 4008 and a bottom surface 4009. The flanged recessed ear holes 4002 can be configured to fit snugly and matingly into the recessed ear holes of the apparatus (not shown). The top surface 4008 of the height adjusting insert 4001 can also be configured to fit snugly and matingly into the bottom surface of the apparatus (not shown), for example, in a manner described herein for other inserts. The angle β formed between the top surface 4008 and bottom surface 4009 can be within any suitable range, for example some embodiments, the angle β can range between 15° and 45°.

Those having ordinary skill in the art will appreciate that various changes can be made to the above embodiments without departing from the scope of the invention.

What is claimed is:

1. An apparatus for airway management of a user, the apparatus comprising:
    an upper surface comprising:
        at least one head-receiving portion configured to receive at least a portion of head of the user; and
        at least one neck-receiving portion configured to receive at least a portion of neck of the user when the head is in a head-receiving portion; and
    at least one chin support protruding over the upper surface and configured to facilitate placing the user in a sniff position when the head in the head-receiving portion, the at least one chin support comprising:
        a top surface;
        a lateral surface comprising at least one portion that extends from the top surface to the at least one neck-receiving portion; and
        at least one of: an adjustable chin positioner and two or more removable chin supports;
        wherein the two or more removable chin supports comprise differing shapes and sizes and are configured such that each removable chin support is attached onto and detached from the apparatus by mechanical means;
    wherein the at least one head-receiving portion, the at least one neck-receiving portion, and the at least one chin support are positioned relative to one another and dimensioned such that when the user is in a lateral decubitus position with the head in the at least one head-receiving portion, oropharyngeal, laryngeal and tracheal axes of the user are substantially aligned.

2. The apparatus of claim 1, wherein the at least a portion of the lateral surface exhibits a downward slope toward the head-receiving portion, and the downward slope varies in a range of about 90 degrees to about 20 degrees.

3. The apparatus of claim 1, wherein the at least a portion of the lateral surface comprises a compound slope.

4. The apparatus of claim 1, wherein the neck-receiving portion comprises at least one segment having a concave surface, and the concave surface comprises a radius of curvature in a range of about 1 inch to about 4 inches.

5. The apparatus of claim 1, wherein the at least one head-receiving portion comprises a left side and a right side separated by a ridge, the at least one neck-receiving portion comprises a left side and a right side separated by the ridge, and the at least one chin support comprises a left chin support and a right chin support, each configured to facilitate placing the user in the sniff position where the head is received in the left or the right head-receiving portions, respectively.

6. The apparatus of claim 1, wherein the at least a portion of the lateral surface comprises a compound curvature, the compound curvature having at least one of: one or more gradient angles between 20° and 60°, at least two gradient angles varying between 20° and 60°, different slopes along two orthogonal directions.

7. The apparatus of claim 1, wherein the at least one chin support comprises one or more segments configured to be at least one of: peeled away and removed from the chin support.

8. The apparatus of claim 1, further comprising a cover configured to encase the apparatus.

9. The apparatus of claim 1, wherein the at least one head-receiving portion comprises a left head-receiving portion and a right head-receiving portion separated by a ridge, the ridge comprising at least one of: a maximum height in a range of about 1 inch to about 5 inches, a non-uniform height, a greater height proximate a front side of the upper surface relative to a back side of the upper surface, a height non-uniformity in a range of about 10% to about 300%, and a maximum width in a range of about 4 inches to about 6 inches.

10. The apparatus of claim 1, wherein the at least one head-receiving portions comprises at least one of:
    a downward-sloping surface extending from a top edge to a bottom end thereof;
    a downward-sloping surface extending from a top edge to a bottom end thereof and comprising a plurality of surface segments exhibiting different slopes;

a compound slope comprising variations in a range of about 20 degrees to about 90 degrees;

a first segment positioned proximate a left side of the upper surface, a second segment positioned proximate a front side of the upper surface, a third segment positioned proximate the ridge, and a fourth segment proximate a front side of the upper surface;

the third surface segment comprises a steeper slope relative to the second surface segment and the second surface segment comprises a steeper slope relative to the first segment;

the at least one head-receiving portion comprises a surface exhibiting a compound slope;

the compound slope comprises slope variations in a range of about 20 degrees to about 90 degrees; and a lower surface positioned opposed to the upper surface.

11. The apparatus of claim 1, wherein the at least one head-receiving portion comprises at least one recessed ear hole.

12. The apparatus of claim 11, wherein the at least one recessed ear hole comprises at least one of:

a maximum dimension in a range of about 1 inch to about 5 inches;

a circular cross-sectional profile and a diameter in a range of about 1 inch to about 5 inches;

a configuration extending from the upper surface to a lower surface of the apparatus;

a configuration configured to at least partially muffle noise experienced by the user while the head of the user is in the at least one head-receiving portion; and a configuration at least partially reducing noise experienced by the user while the head is in the at least one head-receiving portion.

13. An apparatus for airway management of a user, comprising:

at least two portions separated by a ridge, each of the at least two portions comprising:

a head-receiving portion configured to receive head of the user;

a neck-receiving portion configured to support neck of the user when the head is received in the head-receiving portion;

at least one chin support configured to facilitate placing the user in a sniff position when the head is received in the head-receiving portion in a lateral decubitus position, the at least one chin support comprising an adjustable chin positioner;

wherein the head-receiving portion, the neck-receiving portion, and the chin support are positioned relative to one another and dimensioned such that when the user is in the lateral decubitus position with the head received by the head-receiving portion, oropharyngeal, laryngeal and tracheal axes of the user are substantially aligned.

14. The apparatus of claim 13, wherein at least one head-receiving cavity comprises a recessed ear hole, the recessed ear hole being configured to extend through the apparatus, from an upper surface of the apparatus to a lower surface thereof.

15. The apparatus of claim 13, wherein the apparatus comprises a recess for receiving a shoulder of the user, the recess extending between chin supports of the at least two portions.

16. An apparatus for airway management of a user, comprising:

a polymeric block comprising an upper surface, the upper surface comprising:

at least one head-receiving portion configured to receive head of the user;

at least one neck-receiving portion configured to support neck of the user when the head is received in the head-receiving portion; and at least one chin support protruding above the upper surface at a height ranging from about 1 inch to about 5 inches, the at least one chin support comprising at least one of: an adjustable chin positioner and two or more removable chin supports, wherein the two or more removable chin supports comprise differing shapes and sizes and are configured such that each removable chin support is attached onto and detached from the apparatus by mechanical means; and wherein the chin support is configured to at least partially place the user in a sniff position when the head is received in the head-receiving portion.

17. The apparatus of claim 16, wherein the head-receiving cavity exhibits a compound slope.

18. The apparatus of claim 16, further comprising at least one shoulder-receiving recess configured to receive a shoulder of the user, wherein the shoulder-receiving recess comprises a width in a range of about 6 inches to about 18 inches.

19. The apparatus of claim 16, further comprising at least one ear hole extending from the upper surface to a lower surface opposed to the upper surface.

20. The apparatus of claim 19, further comprising a first cover for at least partially enclosing the apparatus such that at least an extension portion of the first cover extends through the at least one ear hole to be fastened to a bottom portion thereof.

* * * * *